US012491368B2

(12) United States Patent

Greenhut et al.

(10) Patent No.: US 12,491,368 B2

(45) Date of Patent: Dec. 9, 2025

(54) MEDICAL DEVICE AND METHOD FOR CARDIAC PACING AND SENSING

(71) Applicant: Medtronic, Inc., Minneapolis, MN (US)

(72) Inventors: Saul E. Greenhut, Denver, CO (US); Alfonso Aranda Hernandez, Maastricht (NL); Timothy A. Ebeling, Circle Pines, MN (US); Michael W. Heinks, New Brighton, MN (US); Jean E. Hudson, Blaine, MN (US); Troy E. Jackson, Rogers, MN (US); Yuanzhen Liu, Minneapolis, MN (US); Irving J. Sanchez, Blaine, MN (US); James A. Vander Heyden, Delano, MN (US); Xusheng Zhang, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 444 days.

(21) Appl. No.: 17/822,681

(22) Filed: Aug. 26, 2022

(65) Prior Publication Data

US 2023/0107061 A1 Apr. 6, 2023

Related U.S. Application Data

(60) Provisional application No. 63/251,820, filed on Oct. 4, 2021, provisional application No. 63/251,803, filed on Oct. 4, 2021.

(51) Int. Cl.
*A61N 1/365* (2006.01)

(52) U.S. Cl.
CPC .................................... *A61N 1/365* (2013.01)

(58) Field of Classification Search
CPC .. A61N 1/365; A61N 1/36507; A61N 1/3702; A61N 1/39622; A61N 1/3621; A61B 5/363; A61B 5/4836
See application file for complete search history.

(56) References Cited

U.S. PATENT DOCUMENTS

| | | | |
|---|---|---|---|
| 6,141,588 | A | 10/2000 | Cox |
| 7,248,921 | B2 | 7/2007 | Palreddy |
| 7,496,409 | B2 | 2/2009 | Greenhut |
| 7,650,182 | B2 | 1/2010 | Kim |
| 7,761,142 | B2 | 7/2010 | Ghanem |

(Continued)

FOREIGN PATENT DOCUMENTS

WO 2008137536 A1 11/2008

OTHER PUBLICATIONS

Heinks, et al., U.S. Appl. No. 63/310,558, filed Feb. 15, 2022, 167 pages.

(Continued)

*Primary Examiner* — Carl H Layno
*Assistant Examiner* — Dhrasti Snehal Dalal

(57) ABSTRACT

A medical device is configured to receive cardiac electrical signals and sense ventricular event signals from the cardiac electrical signals. The medical device may start a validation window in response to sensing a ventricular event signal and determine if the ventricular event signal is a valid event signal or an invalid event signal based on processing of a different cardiac electrical signal than the cardiac electrical signal from which the ventricular event signal was sensed.

26 Claims, 24 Drawing Sheets

(56) References Cited

U.S. PATENT DOCUMENTS

| | | | |
|---|---|---|---|
| 7,774,049 B2 | 8/2010 | Ghanem | |
| 7,904,153 B2 | 3/2011 | Greenhut | |
| 7,907,993 B2 | 3/2011 | Ghanem | |
| 7,991,471 B2 | 8/2011 | Ghanem | |
| 8,068,901 B2 | 11/2011 | Ghanem | |
| 8,577,455 B2 | 11/2013 | Mitrani | |
| 8,750,976 B2 | 6/2014 | Stadler | |
| 8,781,585 B2 | 7/2014 | Gunderson | |
| 8,825,157 B2 | 9/2014 | Warren | |
| 9,956,423 B2 | 5/2018 | Zhang | |
| 10,252,071 B2 | 4/2019 | Cao | |
| 10,328,274 B2 | 6/2019 | Zhang | |
| 10,362,948 B2 | 7/2019 | Brisben | |
| 10,507,332 B2 | 12/2019 | Zhang | |
| 10,561,332 B2 | 2/2020 | Zhang | |
| 10,576,288 B2 | 3/2020 | Cao | |
| 10,675,478 B2 | 6/2020 | Marshall | |
| 10,709,379 B2 | 7/2020 | Warren | |
| 10,750,970 B2 | 8/2020 | Stadler | |
| 2016/0106989 A1 | 4/2016 | Stadler et al. | |
| 2016/0114168 A1* | 4/2016 | Demmer | A61B 5/353 607/18 |
| 2017/0312532 A1 | 11/2017 | Zhang et al. | |
| 2017/0354827 A1* | 12/2017 | Zhang | A61B 5/353 |
| 2021/0170170 A1 | 6/2021 | Mischler et al. | |

OTHER PUBLICATIONS

Aranda-Hernandez, et al., U.S. Appl. No. 63/278,955, filed Nov. 12, 2021, 123 pages.

PCT/IB2022/058659) PCT Notification of Transmittal of the International Search Report and the Written Opinion of the International Searching Authority, Mailed Nov. 24, 2022, 11 pages.

* cited by examiner

MEDICAL DEVICE AND METHOD FOR CARDIAC PACING AND SENSING

REFERENCE TO RELATED APPLICATIONS

This application claims the benefit of provisional U.S. Patent Application No. 63/251,803, filed on Oct. 4, 2021, and the benefit of provisional U.S. Patent Application No. 63/251,820, filed on Oct. 4, 2021, the entire contents of each of which is incorporated by reference herein.

TECHNICAL FIELD

The disclosure relates generally to a medical device and method for sensing cardiac signals and delivering cardiac pacing.

BACKGROUND

Medical devices may sense electrophysiological signals from the heart, brain, nerve, muscle or other tissue. Such devices may be implantable, wearable or external devices using implantable and/or surface (skin) electrodes for sensing the electrophysiological signals. In some cases, such devices may be configured to deliver a therapy based on the sensed electrophysiological signals. For example, implantable or external cardiac pacemakers, cardioverter defibrillators, cardiac monitors and the like sense cardiac electrical signals from a patient's heart. The medical device may sense cardiac electrical signals from a heart chamber and deliver electrical stimulation therapies to the heart chamber using electrodes carried by a transvenous medical electrical lead that positions electrodes within the patient's heart.

A cardiac pacemaker or cardioverter defibrillator may deliver therapeutic electrical stimulation to the heart via electrodes carried by one or more medical electrical leads coupled to the medical device. The electrical stimulation may include signals such as pacing pulses and/or cardioversion or defibrillation shocks. In some cases, a medical device may sense cardiac electrical signals attendant to the intrinsic depolarizations of the myocardium and control delivery of stimulation signals to the heart based on sensed cardiac electrical signals. Cardiac signals sensed within a heart chamber using endocardial electrodes carried by transvenous leads, for example, generally have a high signal strength and quality for reliably sensing near-field cardiac electrical events, such as ventricular R-waves sensed from within a ventricle. Upon detection of an abnormal rhythm, such as bradycardia, tachycardia or fibrillation, an appropriate electrical stimulation signal or signals may be delivered to restore or maintain a more normal rhythm of the heart. For example, an implantable cardioverter defibrillator (ICD) may deliver pacing pulses to the heart of the patient upon detecting bradycardia or tachycardia or deliver cardioversion or defibrillation (CV/DF) shocks to the heart upon detecting tachycardia or fibrillation.

SUMMARY

In general, this disclosure is directed to a medical device and techniques for sensing cardiac electrical signals from electrodes implanted in an extracardiac location and controlling pacing pulses delivered in response to the sensed cardiac electrical signals. The medical device is configured to sense a ventricular event signal attendant to ventricular myocardial depolarization from a cardiac electrical signal and determine if the ventricular event signal is a valid event signal corresponding to a true intrinsic R-wave with a high probability or an invalid event signal likely due to oversensing. The medical device may determine whether the ventricular sensed event signal is valid or invalid based on sensing a second ventricular event signal from a second cardiac electrical signal within a validation window from the first ventricular event signal and/or determining that one or more morphology features determined from a cardiac electrical signal segment meets R-wave morphology criteria.

In response to a valid ventricular event signal, a pacing escape interval set to schedule a pending cardiac pacing pulse may be restarted. In response to an invalid ventricular event signal, a running pacing escape interval is allowed to continue running. When the running pacing escape interval expires after a ventricular event signal is sensed but before it is determined to be valid or invalid, the pending cardiac pacing pulse scheduled for delivery upon expiration of the pacing escape interval may be withheld until after the validation window expires in some examples.

In one example, the disclosure provides a medical device including a therapy delivery circuit configured to generate cardiac pacing pulses and a sensing circuit configured to receive multiple cardiac electrical signals and sense ventricular event signals from the cardiac electrical signals. The medical device further includes a control circuit configured to start a validation window in response to each ventricular event signal sensed by the sensing circuit that is an earliest ventricular event signal sensed outside a previously started validation window. For each of the earliest ventricular event signals, the control circuit may determine that the earliest ventricular event signal is one of a valid event signal or an invalid event signal based on processing of at least a second cardiac electrical signal of the cardiac electrical signals that is received during the validation window. The second cardiac electrical signal may be different than a first cardiac electrical signal from which the earliest ventricular event signal was sensed. In some examples, for each of the earliest ventricular event signals that is determined to be a valid event signal, the control circuit may determine a sensed event interval and detect alternating intervals from the determined sensed event intervals. The alternating intervals may include at least a long interval and a short interval. In response to detecting the alternating intervals, the control circuit may determine a morphology feature from at least one of the sensed cardiac electrical signals corresponding to a time of a valid event signal and determine that the morphology feature meets R-wave criteria. In response to the R-wave criteria being met, the control circuit may start a pacing escape interval to schedule a pending cardiac pacing pulse for delivery by the therapy delivery circuit.

In another example, the disclosure provides a method that includes receiving a multiple cardiac electrical signals, sensing ventricular event signals from the cardiac electrical signals and starting a validation window in response to each ventricular event signal that is an earliest ventricular event signal sensed outside a previously started validation window. For each of the earliest ventricular event signals, the method may further include determining that the earliest ventricular event signal is either a valid event signal or an invalid event signal based on processing of at least a second cardiac electrical signal of the sensed cardiac electrical signals received during the validation window. The second cardiac electrical signal may be different than a first cardiac electrical signal from which the earliest ventricular event signal was sensed. In some examples, for each of the earliest ventricular event signals that is determined to be a valid event signal, the method may further include, determining a sensed event interval, detecting alternating intervals from the determined sensed event intervals including at least a long interval and a short interval and, in response to detecting the alternating intervals, determining a morphology feature from at least one of the sensed cardiac electrical signals corresponding to a time of a valid event signal. The method may further include determining that the morphology feature meets R-wave criteria and, in response to the R-wave criteria being met, starting a pacing escape interval to schedule a pending cardiac pacing pulse.

In another example, the disclosure provides a non-transitory computer-readable medium storing a set of instructions which, when executed by a control circuit of a medical device, cause the medical device to receive multiple cardiac electrical signals and sense ventricular event signals from the cardiac electrical signals. The instructions further cause the medical device to start a validation window in response to each ventricular event signal that is an earliest ventricular event signal sensed outside a previously started validation window. For each of the earliest ventricular event signals, the instructions may further cause the medical device to determine that the earliest ventricular event signal is either a valid event signal or an invalid event signal based on processing of at least a second cardiac electrical signal of the cardiac electrical signals received during the validation window. The second cardiac electrical signal may be different than a first cardiac electrical signal from which the earliest ventricular event signal was sensed. In some examples, for each of the earliest ventricular event signals that is determined to be a valid event signal, the instructions may further cause the device to determine a sensed event interval, detect alternating intervals from the determined sensed event intervals comprising at least a long interval and a short interval, and, in response to detecting the alternating intervals, determine a morphology feature from at least one of the plurality of cardiac electrical signals corresponding to a time of a valid event signal. The instructions may further cause the medical device to determine that the morphology feature meets R-wave criteria and, in response to the R-wave criteria being met, start a pacing escape interval to schedule a pending cardiac pacing pulse.

Further disclosed herein is the subject matter of the following examples:

Example 1. A medical device including a therapy delivery circuit configured to generate pacing pulses and a sensing circuit configured to receive a plurality of cardiac electrical signals and sense a first ventricular event signal from a first cardiac electrical signal of the plurality of cardiac electrical signals. The medical device further including a control circuit configured to start a pacing escape interval to schedule a pending cardiac pacing pulse and start a predetermined time interval in response to the sensing circuit sensing the first ventricular event signal. The predetermined time interval is also be referred to herein as a "validation window." The control circuit may be further configured to determine that the first ventricular event signal is one of a valid event signal or an invalid event signal based on processing of at least a second cardiac electrical signal of the plurality of cardiac electrical signals received during the predetermined time interval, and cancel the pending cardiac pacing pulse by restarting the pacing escape interval in response to determining that the first ventricular event signal is a valid event signal.

Example 2. The medical device of example 1 wherein the control circuit is further configured to determine that the pacing escape interval expires during the predetermined time interval and control the therapy delivery circuit to withhold the pending cardiac pacing pulse that is scheduled at the expiration of the pacing escape interval in response to the pacing escape interval expiring during the predetermined time interval.

Example 3. The medical device of any of examples 1-2 wherein the therapy delivery circuit is further configured to deliver the pending cardiac pacing pulse after the predetermined time interval in response to the control circuit determining that the first ventricular event signal is an invalid event signal.

Example 4. The medical device of any of examples 1-3 wherein the sensing circuit is further configured to sense a second ventricular event signal from the second cardiac electrical signal. The control circuit is further configured to determine that the first ventricular event signal is a valid event signal by determining that the second ventricular event signal is sensed by the sensing circuit during the predetermined time interval.

Example 5. The medical device of any of examples 1-4, further comprising a memory configured to store a cardiac electrical signal segment from at least one of the plurality of cardiac electrical signals in response to the first ventricular event signal being sensed by the sensing circuit. The control circuit is further configured to determine that the first ventricular event signal is a valid event signal by determining at least one morphology feature from the cardiac electrical signal segment, determining that the at least one morphology feature from the cardiac electrical signal segment meets R-wave criteria and determining that the first ventricular event signal is a valid event signal in response to the at least one morphology feature meeting the R-wave criteria.

Example 6. The medical device of any of examples 1-5 wherein the control circuit is further configured to determine that the first ventricular event signal is one of a valid event signal or an invalid event signal based on the processing of at least the second cardiac electrical signal of the plurality of cardiac electrical signals by: determining that a second ventricular event signal is not sensed from the second cardiac electrical signal during the predetermined time interval; determining at least one morphology feature from a cardiac electrical signal segment of the plurality of cardiac electrical signals received during the predetermined time interval; determining that the at least one morphology feature does not meet R-wave criteria; and determining that the first ventricular event signal is an invalid event signal in response to determining that a second ventricular event signal is not sensed from the second cardiac electrical signal during the predetermined time interval and that the at least one morphology feature does not meet the R-wave criteria.

Example 7. The medical device of any of examples 5-6 wherein the control circuit is further configured to determine that a second ventricular event signal is sensed from the second cardiac electrical signal of the plurality of cardiac signals during the predetermined time interval. The control circuit can be further configured to abort determining that the at least one morphology feature from the cardiac electrical signal segment meets R-wave criteria in response to the second ventricular event signal being sensed during the predetermined time interval.

Example 8. The medical device of any of examples 5-7 wherein the memory is further configured to store an R-wave morphology template. The control circuit is further configured to determine the at least one morphology feature by determining a morphology matching score between the cardiac electrical signal segment and the R-wave morphology template and determine that the at least one morphology feature meets the R-wave criteria in response to the morphology matching score being greater than a matching score threshold.

Example 9. The medical device of any of examples 5-8 wherein the control circuit is further configured to determine the at least one morphology feature by: determining a peak amplitude of the cardiac electrical signal segment; determining a difference signal from the cardiac electrical signal segment; and determining a peak-to-peak amplitude of the difference signal. The control circuit is further configured to determine that the at least one morphology feature meets the R-wave morphology criteria in response to the peak amplitude being greater than an amplitude threshold and the peak-to-peak amplitude of the difference signal being greater than a slope threshold.

Example 10. The medical device of example 9 wherein the control circuit is further configured to determine the peak-to-peak amplitude difference of the difference signal from a portion of the cardiac electrical signal segment that occurs later than the first ventricular event signal.

Example 11. The medical device of any of examples 1-10 wherein the control circuit is further configured to determine a plurality of features from a cardiac electrical signal segment of the plurality of cardiac electrical signals in response to the sensing circuit sensing the first ventricular event signal. The control circuit can be further configured to determine that the plurality of features meet ectopic beat criteria and determine that the first ventricular event signal is a valid event signal in response to the ectopic beat criteria being met.

Example 12. The medical device of any of examples 1-11 wherein the sensing circuit is further configured to set a sensing threshold to a minimum sensing threshold amplitude; sense the first ventricular event signal in response to the first cardiac electrical signal crossing the sensing threshold set to the minimum sensing threshold amplitude. The control circuit is further configured to determine at least one morphology feature from a cardiac electrical signal segment of the plurality of cardiac electrical signals in response to the first ventricular event signal being sensed when the sensing threshold is set to the minimum sensing threshold amplitude. The control circuit can be further configured to determine that the at least one morphology feature meets R-wave criteria and determine that the first ventricular event signal is a valid event signal in response to the at least one morphology feature meeting the R-wave criteria.

Example 13. The medical device of any of examples 1-12 wherein the control circuit is further configured to determine that a maximum peak amplitude of the first ventricular event signal is less than a threshold amplitude and determine at least one morphology feature from a cardiac electrical signal segment of the plurality of cardiac electrical signals in response to maximum peak amplitude of the first ventricular event signal being less than the threshold amplitude. The control circuit is further configured to determine that the at least one morphology feature meets R-wave criteria and determine that the first ventricular event signal is a valid event signal in response to the at least one morphology feature meeting the R-wave criteria.

Example 14. The medical device of any of examples 1-13 wherein the control circuit is further configured to determine that a second ventricular event signal is sensed by the sensing circuit from a second cardiac electrical signal of the plurality of cardiac electrical signals during a first portion of the predetermined time interval and determine that the first ventricular event signal is a valid event signal in response to the second ventricular event signal being sensed during the first portion of the predetermined time interval.

Example 15. The medical device of any of examples 1-14 wherein the control circuit is further configured to determine that a second ventricular event signal is sensed by the sensing circuit during a second portion of the predetermined time interval that is later than a first portion of the predetermined time interval and determine at least one morphology feature of a cardiac electrical signal segment of the plurality of cardiac electrical signals in response to the second ventricular event signal being sensed during the second portion of the predetermined time interval. The control circuit is further configured to determine that the at least one morphology feature meets R-wave criteria and determine that the first ventricular sensed event signal is a valid event signal in response to the second ventricular event signal being sensed during the second portion of the predetermined time interval and the at least one morphology feature of the cardiac electrical signal segment meeting R-wave criteria.

Example 16. The medical device of any of examples 1-15 wherein the sensing circuit is further configured to set a sensing threshold according to at least one sensing threshold control parameter and sense the first ventricular event signal in response to the first cardiac electrical signal crossing the sensing threshold. The control circuit is further configured to, in response to determining that the first ventricular event signal is an invalid event signal, adjust the at least one sensing threshold control parameter.

Example 17. The medical device of any of examples 1-16 wherein the sensing circuit is further configured to set a sensing threshold according to at least one sensing threshold control parameter and sense the first ventricular event signal in response to the first cardiac electrical signal crossing the sensing threshold. The control circuit is further configured to, in response to determining that the first ventricular event signal is a valid event signal, adjust the at least one sensing threshold control parameter.

Example 18. The medical device of any of examples 1-17 wherein the control circuit is further configured to set a pace delay interval in response to the first ventricular event signal being determined to be an invalid event signal and determine that the pacing escape interval expires after the first ventricular event signal and prior to an expiration of the pace delay interval. The therapy delivery circuit is further configured to deliver the pending cardiac pacing pulse after the expiration of the pace delay interval in response to the control circuit determining that the pacing escape interval expires prior to the expiration of the pace delay interval.

Example 19. The medical device of any of examples 1-18 wherein the control circuit is further configured to determine that the first ventricular event signal is one of a valid event signal or an invalid event signal by: determining a noise metric from one of the plurality of cardiac electrical signals during a noise analysis window corresponding to a time of the sensed first ventricular event signal; determining that the noise metric does not meet noisy cycle criteria; and determining that the first ventricular event signal is a valid event signal in response to the noise metric not meeting the noisy cycle criteria.

Example 20. A method including starting a pacing escape interval to schedule a pending cardiac pacing pulse, receiving a plurality of cardiac electrical signals, sensing a first ventricular event signal from a first cardiac electrical signal of the plurality of cardiac electrical signals and starting a predetermined time interval in response to sensing the first ventricular event signal. The method further includes determining that the first ventricular event signal is one of a valid event signal or an invalid event signal based on processing of at least a second cardiac electrical signal of the plurality of cardiac electrical signals received during the predetermined time interval and cancelling the pending cardiac pacing pulse by restarting the pacing escape interval in response to determining that the first ventricular event signal is a valid event signal.

Example 21. The method of example 20 further comprising determining that the pacing escape interval expires during the predetermined time interval and withholding the pending cardiac pacing pulse that is scheduled at the expiration of the pacing escape interval in response to the pacing escape interval expiring during the predetermined time interval.

Example 22. The method of any of examples 20-21 further comprising delivering the pending cardiac pacing pulse after the first predetermined time interval in response to determining that the first ventricular event signal is an invalid event signal.

Example 23. The method of any of examples 20-22 further comprising sensing a second ventricular event signal from the second cardiac electrical signal and determining that the first ventricular event signal is a valid event signal by determining that the second ventricular event signal is sensed during the predetermined time interval.

Example 24. The method of any of examples 20-23 further comprising storing a cardiac electrical signal segment from at least one of the plurality of cardiac electrical signals in response to sensing the first ventricular event signal, determining at least one morphology feature from the cardiac electrical signal segment, determining that the at least one morphology feature from the cardiac electrical signal segment meets R-wave criteria, and determining that the first ventricular event signal is a valid event signal in response to the at least one morphology feature meeting the R-wave criteria.

Example 25. The method of any of examples 20-24 wherein determining that the first ventricular event signal is one of a valid event signal or an invalid event signal based on the processing of at least the second cardiac electrical signal of the plurality of cardiac electrical signals comprises: determining that a second ventricular event signal is not sensed from the second cardiac electrical signal during the predetermined time interval; determining at least one morphology feature from a cardiac electrical signal segment of the plurality of cardiac electrical signals received during the predetermined time interval; determining that the at least one morphology feature does not meet R-wave criteria; and determining that the first ventricular event signal is an invalid event signal in response to determining that a second ventricular event signal is not sensed from the second cardiac electrical signal during the predetermined time interval and that the at least one morphology feature does not meet the R-wave criteria.

Example 26. The method of any of examples 24-25 further comprising determining that a second ventricular event signal is sensed from the second cardiac electrical signal of the plurality of cardiac signals during the predetermined time interval and aborting determining that the at least one morphology feature from the cardiac electrical signal segment meets R-wave criteria in response to the second ventricular event signal being sensed during the predetermined time interval.

Example 27. The method of any of examples 24-26 further comprising storing an R-wave morphology template, determining the at least one morphology feature by determining a morphology matching score between the cardiac electrical signal segment and the R-wave morphology template, and determining that the at least one morphology feature meets the R-wave morphology criteria in response to the morphology matching score being greater than a matching score threshold.

Example 28. The method of any of examples 24-27 further comprising determining the at least one morphology feature by: determining a peak amplitude of the cardiac electrical signal segment; determining a difference signal from the cardiac electrical signal segment; and determining a peak-to-peak amplitude of the difference signal. The method further comprising determining that the at least one morphology feature meets the R-wave criteria in response to the peak amplitude being greater than an amplitude threshold and the peak-to-peak amplitude of the difference signal being greater than a slope threshold.

Example 29. The method of example 28 further comprising determining the peak-to-peak amplitude difference of the difference signal from a portion of the cardiac electrical signal segment that occurs later than the first ventricular event signal.

Example 30. The method of any of examples 20-29 further comprising determining a plurality of features from a cardiac electrical signal segment of the plurality of cardiac electrical signals in response to sensing the first ventricular event signal, determining that the plurality of features meets ectopic beat criteria and determining that the first ventricular event signal is a valid event signal in response to the ectopic beat criteria being met.

Example 31. The method of any of examples 20-30 further comprising setting a sensing threshold to a minimum sensing threshold amplitude and sensing the first ventricular event signal in response to the first cardiac electrical signal crossing the sensing threshold set to the minimum sensing threshold amplitude. The method further including determining at least one morphology feature from a cardiac electrical signal segment of the plurality of cardiac electrical signals in response to the first ventricular event signal being sensed when the sensing threshold is set to the minimum sensing threshold amplitude, determining that the at least one morphology feature meets R-wave criteria and determining that the first ventricular event signal is a valid event signal in response to the at least one morphology feature meeting the R-wave criteria.

Example 32. The method of any of examples 20-31 further comprising determining that a maximum peak amplitude of the first ventricular event signal is less than a threshold amplitude, determining at least one morphology feature from a cardiac electrical signal segment of the plurality of cardiac electrical signals in response to maximum peak amplitude of the first ventricular event signal being less than the threshold amplitude, determining that the at least one morphology feature meets R-wave criteria, and determining that the first ventricular event signal is a valid event signal in response to the at least one morphology feature meeting the R-wave criteria.

Example 33. The method of any of examples 20-32 further comprising sensing a second ventricular event signal from a second cardiac electrical signal of the plurality of cardiac electrical signals during a first portion of the predetermined time interval and determining that the first ventricular event signal is a valid event signal in response to the second ventricular event signal being sensed during the first portion of the predetermined time interval.

Example 34. The method of any of examples 20-33 further comprising sensing a second ventricular event signal from a second cardiac electrical signal of the plurality of cardiac electrical signals during a second portion of the predetermined time interval that is later than a first portion of the predetermined time interval and determining at least one morphology feature of a cardiac electrical signal segment of the plurality of cardiac electrical signals in response to the second ventricular event signal being sensed during the second portion of the predetermined time interval. The method further including determining that the at least one morphology feature meets R-wave criteria and determining that the first ventricular sensed event signal is a valid event signal in response to the second ventricular event signal being sensed during the second portion of the predetermined time interval and the at least one morphology feature of the cardiac electrical signal segment meeting R-wave criteria.

Example 35. The method of any of examples 20-34, further comprising setting a sensing threshold according to at least one sensing threshold control parameter, sensing the first ventricular event signal in response to the first cardiac electrical signal crossing the sensing threshold and, in response to determining that the first ventricular event signal is an invalid event signal, adjusting the at least one sensing threshold control parameter.

Example 36. The method of any of examples 20-35, further comprising setting a sensing threshold according to at least one sensing threshold control parameter, sensing the first ventricular event signal in response to the first cardiac electrical signal crossing the sensing threshold. The method further including, in response to determining that the first ventricular event signal is a valid event signal, adjusting the at least one sensing threshold control parameter.

Example 37. The method of any of examples 20-36 further comprising setting a pace delay interval in response to the first ventricular event signal being determined to be an invalid event signal, determining that the pacing escape interval expires after the first ventricular event signal and prior to an expiration of the pace delay interval, and delivering the pending cardiac pacing pulse after the expiration of the pace delay interval in response to the pacing escape interval expiring prior to the expiration of the pace delay interval.

Example 38. The method of any of examples 20-37 wherein determining that the first ventricular event signal is one of a valid event signal or an invalid event signal comprises: determining a noise metric from one of the plurality of cardiac electrical signals during a noise analysis window corresponding to a time of the sensed first ventricular event signal; determining that the noise metric does not meet noisy cycle criteria; and determining that the first ventricular event signal is a valid event signal in response to the noise metric not meeting the noisy cycle criteria.

Example 39. A non-transitory computer-readable medium storing a set of instructions which, when executed by a control circuit of a medical device, cause the medical device to start a pacing escape interval to schedule a pending cardiac pacing pulse, receive a plurality of cardiac electrical signals and sense a ventricular event signal from a first cardiac electrical signal of the plurality of cardiac electrical signals. The instructions further cause the medical device to start a predetermined time interval in response to sensing the ventricular event signal, determine that the ventricular event signal is one of a valid event signal or an invalid event signal based on processing of at least a second cardiac electrical signal of the plurality of cardiac electrical signals received during the predetermined time interval, and cancel the pending cardiac pacing pulse by restarting the pacing escape interval in response to determining that the ventricular event signal is a valid event signal.

Example 40. The non-transitory computer-readable medium of example 39 wherein the instructions further cause the medical device to determine that the pacing escape interval expires during the predetermined time interval and withhold the pending cardiac pacing pulse that is scheduled at the expiration of the pacing escape interval in response to the pacing escape interval expiring during the predetermined time interval.

Example 41. A medical device including a therapy delivery circuit configured to generate cardiac pacing pulses and a sensing circuit configured to receive a plurality of cardiac electrical signals and sense ventricular event signals from the plurality of cardiac electrical signals. The medical device further includes a control circuit configured to start a validation window in response to each ventricular event signal of the plurality of ventricular event signals that is an earliest ventricular event signal sensed outside a previously started validation window. For each of the earliest ventricular event signals the control circuit is further configured to determine that the earliest ventricular event signal is one of a valid event signal or an invalid event signal based on processing of at least a second cardiac electrical signal of the plurality of cardiac electrical signals received during the validation window, the second cardiac electrical signal being different than a first cardiac electrical signal from which the earliest ventricular event signal was sensed. For each of the earliest ventricular event signals that is determined to be a valid event signal, the control circuit is further configured to determine a sensed event interval. The control circuit is further configured to detect from the determined sensed event intervals alternating intervals comprising at least a long interval and a short interval. In response to detecting the alternating intervals, the control circuit is further configured to determine a first morphology feature from at least one of the plurality of cardiac electrical signals corresponding to a time of a valid event signal, determine that the first morphology feature meets R-wave criteria, and, in response to the R-wave criteria being met, start a pacing escape interval to schedule a pending cardiac pacing pulse for delivery by the therapy delivery circuit.

Example 42. The medical device of example 41 wherein the control circuit is further configured to determine that the pacing escape interval expires without a valid event signal being determined during the pacing escape interval. The therapy delivery circuit is further configured to deliver the pending cardiac pacing pulse in response to the expiration of the pacing escape interval.

Example 43. The medical device of any of examples 41-42 wherein the control circuit is further configured to determine that the pacing escape interval expires during a validation window and control the therapy delivery circuit to withhold the pending cardiac pacing pulse that is scheduled at the expiration of the pacing escape interval in response to the pacing escape interval expiring during the validation window.

Example 44. The medical device of example 43 wherein the control circuit is further configured to determine that an earliest ventricular event signal starting the validation window is an invalid event signal and determine that the validation window expires. The therapy delivery circuit is further configured to deliver the withheld pending cardiac pacing pulse after the expiration of the validation window in response to the control circuit determining that the earliest ventricular event signal starting the validation window is an invalid event signal.

Example 45. The medical device of any of examples 41-44 wherein the control circuit is further configured to determine that each earliest ventricular event signal is one of a valid event signal or an invalid event signal by determining that a later ventricular event signal is sensed during the validation window from the second cardiac electrical signal by the sensing circuit and determining that the earliest ventricular event signal is a valid event signal in response to the later ventricular event signal being sensed during the validation window.

Example 46. The medical device of any of examples 41-45 wherein the control circuit is further configured to determine a corrected sensed event interval by adding the long interval and the short interval, determine that the corrected sensed event interval is greater than the pacing escape interval and determine the first morphology feature in response to the corrected sensed event interval being greater than the pacing escape interval.

Example 47. The medical device of any of examples 41-46 wherein the control circuit is further configured to determine a corrected sensed event interval by adding the long interval and the short interval, determine that the corrected sensed event interval is less than the pacing escape interval. In response to the corrected sensed event interval being less than the pacing escape interval, the control circuit is further configured to determine a second morphology feature from at least one of the plurality of cardiac electrical signals corresponding to a time of a valid event signal ending the long interval and establish P-wave oversensing criteria based on the second morphology feature.

Example 48. The medical device of example 47 wherein the control circuit is further configured to detect non-alternating intervals from a portion of the determined sensed event intervals that occur after the detected alternating intervals. In response to detecting the non-alternating intervals, the control circuit is further configured to determine the second morphology feature from at least one of the plurality of cardiac electrical signals corresponding to a time of a ventricular event signal sensed during the pacing escape interval. The control circuit is further configured to determine that the second morphology feature corresponding to the time of the ventricular event signal sensed during the pacing escape interval meets the established P-wave oversensing criteria, determine that the ventricular event signal sensed during the pacing escape interval is invalid based on the P-wave oversensing criteria being met, and determine that the pacing escape interval expires. The therapy delivery circuit is further configured to deliver the pending cardiac pacing pulse in response to the expiration of the pacing escape interval and the ventricular event signal sensed during the pacing escape interval being invalid.

Example 49. The medical device of any of examples 41-48 wherein the control circuit is further configured to determine a corrected sensed event interval by adding the long interval and the short interval, determine that the corrected sensed event interval is less than the pacing escape interval. In response to the corrected sensed event interval being less than the pacing escape interval, the control circuit is further configured to determine a third morphology feature from at least one of the plurality of cardiac electrical signals corresponding to a time of a valid event signal ending the short interval and establish T-wave oversensing criteria based on the third morphology feature.

Example 50. The medical device of example 49 wherein the control circuit is further configured to determine the third morphology feature from at least one of the plurality of cardiac electrical signals corresponding to a time of a ventricular event signal sensed during the pacing escape interval; determine that the third morphology feature corresponding to the time of the ventricular event signal sensed during the pacing escape interval meets the established T-wave oversensing criteria; and determine that the ventricular event signal sensed during the pacing escape interval is invalid based on the T-wave oversensing criteria being met; and determine that the pacing escape interval expires. The therapy delivery circuit is further configured to deliver the pending cardiac pacing pulse in response to the expiration of the pacing escape interval and the ventricular event signal sensed during the pacing escape interval being invalid.

Example 51. The medical device of any of examples 41-50 wherein the sensing circuit is further configured to sense a ventricular event signal during the pacing escape interval. The control circuit is further configured to determine a fourth morphology feature from at least one of the plurality of cardiac electrical signals corresponding to the time of the ventricular event signal sensed during the pacing escape interval, determine that the fourth morphology feature meets ectopic beat criteria and restart the pacing escape interval in response to the ectopic beat criteria being met.

Example 52. The medical device of example 51 wherein the control circuit is further configured to determine a corrected sensed event interval by adding the long interval and the short interval and determine that the corrected sensed event interval is less than the pacing escape interval. In response to the corrected sensed event interval being less than the pacing escape interval, the control circuit is further configured to determine the fourth morphology feature from at least one of the plurality of cardiac electrical signals corresponding to a time of a valid event signal ending the short interval. The control circuit is further configured to establish the ectopic beat criteria based on the fourth morphology feature determined from at least one of the plurality of cardiac electrical signals corresponding to the time of the valid event signal ending the short interval.

Example 53. The medical device of any of examples 41-52 further comprising a memory configured to store an R-wave morphology template. The control circuit is further configured to determine the first morphology feature by determining a morphology matching score between the at least one of the plurality of cardiac electrical signals and the R-wave morphology template and determine that the first morphology feature meets the R-wave criteria in response to the morphology matching score being greater than a matching score threshold.

Example 54. The medical device of any of examples 41-53 wherein the control circuit is further configured to set a pace delay interval in response to an earliest ventricular event signal being determined to be an invalid event signal, determine that a previously started pacing escape interval expires during the pace delay interval and determine that the pace delay interval expires. The therapy delivery circuit is further configured to withhold a pending cardiac pacing pulse scheduled at the expiration of the previously started pacing escape interval determined to expire during the pace delay interval and deliver the pending cardiac pacing pulse scheduled at the expiration of the previously started pacing escape interval after the expiration of the pace delay interval.

Example 55. The medical device of any of examples 41-54 wherein the control circuit is further configured to inhibit sensing of a ventricular event signal by the sensing circuit during an early sensing time interval following an earliest ventricular event signal determined to be a valid event signal.

Example 56. A method including receiving a plurality of cardiac electrical signals, sensing a plurality of ventricular event signals from the plurality of cardiac electrical signals, and starting a validation window in response to each ventricular event signal that is an earliest ventricular event signal sensed outside a previously started validation window. The method further includes, for each of the earliest ventricular event signals, determining that the earliest ventricular event signal is one of a valid event signal or an invalid event signal based on processing of at least a second cardiac electrical signal of the plurality of cardiac electrical signals received during the validation window, the second cardiac electrical signal being different than a first cardiac electrical signal from which the earliest ventricular event signal was sensed. For each of the earliest ventricular event signals that is determined to be a valid event signal, the method includes determining a sensed event interval. The method further includes detecting from the determined sensed event intervals alternating intervals comprising at least a long interval and a short interval. The method further includes, in response to detecting the alternating intervals, determining a first morphology feature from at least one of the plurality of cardiac electrical signals corresponding to a time of a valid event signal, determining that the first morphology feature meets R-wave criteria and, in response to the R-wave criteria being met, starting a pacing escape interval to schedule a pending cardiac pacing pulse.

Example 57. The method of example 56 further comprising determining that the pacing escape interval expires without a valid event signal being determined during the pacing escape interval and delivering the pending cardiac pacing pulse in response to the expiration of the pacing escape interval.

Example 58. The method of any of examples 56-57 further comprising determining that the pacing escape interval expires during a validation window and withholding the pending cardiac pacing pulse that is scheduled at the expiration of the pacing escape interval in response to the pacing escape interval expiring during the validation window.

Example 59. The method of example 58 further comprising determining that an earliest ventricular event signal starting the validation window is an invalid event signal, determining that the validation window expires and delivering the withheld pending cardiac pacing pulse after the expiration of the validation window in response to determining that the earliest ventricular event signal starting the validation window is an invalid event signal.

Example 60. The method of any of examples 56-59 wherein determining that each earliest ventricular event signal is one of a valid event signal or an invalid event signal comprises determining that a later ventricular event signal is sensed during the validation window from the second cardiac electrical signal by the sensing circuit and determining that the earliest ventricular event signal is a valid event signal in response to the later ventricular event signal being sensed during the validation window.

Example 61. The method of any of examples 56-60 further comprising determining a corrected sensed event interval by adding the long interval and the short interval, determining that the corrected sensed event interval is greater than the pacing escape interval and determining the first morphology feature in response to the corrected sensed event interval being greater than the pacing escape interval.

Example 62. The method of any of examples 56-61 further comprising determining a corrected sensed event interval by adding the long interval and the short interval and determining that the corrected sensed event interval is less than the pacing escape interval. The method further includes, in response to the corrected sensed event interval being less than the pacing escape interval, determining a second morphology feature from at least one of the plurality of cardiac electrical signals corresponding to a time of a valid event signal ending the long interval. The method further includes establishing P-wave oversensing criteria based on the second morphology feature.

Example 63. The method of example 62 further including detecting non-alternating intervals from a portion of the determined sensed event intervals that occur after the detected alternating intervals and, in response to detecting the non-alternating intervals, determining the second morphology feature from at least one of the plurality of cardiac electrical signals corresponding to a time of a ventricular event signal sensed during the pacing escape interval. The method further including determining that the second morphology feature corresponding to the time of the ventricular event signal sensed during the pacing escape interval meets the established P-wave oversensing criteria, determining that the ventricular event signal sensed during the pacing escape interval is invalid based on the P-wave oversensing criteria being met, determining that the pacing escape interval expires, and delivering the pending cardiac pacing pulse in response to the expiration of the pacing escape interval and the ventricular event signal sensed during the pacing escape interval being invalid.

Example 64. The method of any of examples 56-63 further comprising determining a corrected sensed event interval by adding the long interval and the short interval and determining that the corrected sensed event interval is less than the pacing escape interval. In response to the corrected sensed event interval being less than the pacing escape interval, the method further includes determining a third morphology feature from at least one of the plurality of cardiac electrical signals corresponding to a time of a valid event signal ending the short interval and establishing T-wave oversensing criteria based on the third morphology feature.

Example 65. The method of example 64 further comprising determining the third morphology feature from at least one of the plurality of cardiac electrical signals corresponding to a time of a ventricular event signal sensed during the pacing escape interval, determining that the third morphology feature corresponding to the time of the ventricular event signal sensed during the pacing escape interval meets the established T-wave oversensing criteria and determining that the ventricular event signal sensed during the pacing escape interval is invalid based on the T-wave oversensing criteria being met. The method further can further include determining that the pacing escape interval expires and delivering the pending cardiac pacing pulse in response to the expiration of the pacing escape interval and the ventricular event signal sensed during the pacing escape interval being invalid.

Example 66. The method of any of examples 56-65 further comprising sensing a ventricular event signal during the pacing escape interval, determining a fourth morphology feature from at least one of the plurality of cardiac electrical signals corresponding to the time of the ventricular event signal sensed during the pacing escape interval, determining that the fourth morphology feature meets ectopic beat criteria and restarting the pacing escape interval in response to the ectopic beat criteria being met.

Example 67. The method of example 66 further comprising determining a corrected sensed event interval by adding the long interval and the short interval and determining that the corrected sensed event interval is less than the pacing escape interval. In response to the corrected sensed event interval being less than the pacing escape interval, the method can further include determining the fourth morphology feature from at least one of the plurality of cardiac electrical signals corresponding to a time of a valid event signal ending the short interval and establishing the ectopic beat criteria based on the fourth morphology feature determined from at least one of the plurality of cardiac electrical signals corresponding to the time of the valid event signal ending the short interval.

Example 68. The method of any of examples 56-67 further comprising storing an R-wave morphology template, determining the first morphology feature by determining a morphology matching score between the at least one of the plurality of cardiac electrical signals and the R-wave morphology template and determining that the first morphology feature meets the R-wave criteria in response to the morphology matching score being greater than a matching score threshold.

Example 69. The method of any of examples 56-68 further comprising setting a pace delay interval in response to an earliest ventricular event signal being determined to be an invalid event signal and determining that a previously started pacing escape interval expires during the pace delay interval. The method may further include determining that the pace delay interval expires and withholding a pending cardiac pacing pulse scheduled at the expiration of the previously started pacing escape interval determined to expire during the pace delay interval. The method may further include delivering the pending cardiac pacing pulse scheduled at an expiration of the previously started pacing escape interval after the expiration of the pace delay interval.

Example 70. The method of any of examples 56-69 further comprising inhibiting sensing of a ventricular event signal during an early sensing time interval following an earliest ventricular event signal determined to be a valid event signal.

Example 71. A non-transitory computer-readable medium storing a set of instructions which, when executed by a control circuit of a medical device, cause the medical device to receive a plurality of cardiac electrical signals, sense a plurality of ventricular event signals from the plurality of cardiac electrical signals and start a validation window in response to each ventricular event signal of the plurality of ventricular event signals that is an earliest ventricular event signal sensed outside a previously started validation window. The instructions further cause the medical device to, for each of the earliest ventricular event signals, determine that the earliest ventricular event signal is one of a valid event signal or an invalid event signal based on processing of at least a second cardiac electrical signal of the plurality of cardiac electrical signals received during the validation window, the second cardiac electrical signal being different than a first cardiac electrical signal from which the earliest ventricular event signal was sensed. For each of the earliest ventricular event signals that is determined to be a valid event signal, the instructions further cause the medical device to determine a sensed event interval. The instructions further cause the medical device to detect from the determined sensed event intervals alternating intervals comprising at least a long interval and a short interval. In response to detecting the alternating intervals, the instructions further cause the medical device to determine a morphology feature from at least one of the plurality of cardiac electrical signals corresponding to a time of a valid event signal and determine that the morphology feature meets R-wave criteria. In response to the R-wave criteria being met, the instructions may further cause the medical device to start a pacing escape interval to schedule a pending cardiac pacing pulse.

Example 72. A medical device including a therapy delivery circuit configured to generate pacing pulses and a sensing circuit configured to receive a plurality of cardiac electrical signals and sense a first ventricular event signal from a first cardiac electrical signal of the plurality of cardiac electrical signals. The medical device further includes a control circuit configured to start a pacing escape interval to schedule a pending cardiac pacing pulse, start a validation window in response to the sensing circuit sensing the first ventricular event signal and determine that the first ventricular event signal is one of a valid event signal or an invalid event signal based on at least a second cardiac electrical signal of the plurality of cardiac electrical signals received during the validation window. The control circuit may be further configured to cancel the pending cardiac pacing pulse in response to determining that the first ventricular event signal is a valid event signal and schedule a subsequent pending pacing pulse by restarting the pacing escape interval in response to determining that the first ventricular event signal is a valid event signal.

Example 73. The medical device of example 72 wherein the control circuit is further configured to determine that the pacing escape interval expires during the validation window and control the therapy delivery circuit to withhold the pending cardiac pacing pulse that is scheduled at the expiration of the pacing escape interval in response to the pacing escape interval expiring during the validation window.

Example 74. The medical device of any of examples 72-73 wherein the therapy delivery circuit is further configured to deliver the pending cardiac pacing pulse after the validation window in response to the control circuit determining that the first ventricular event signal is an invalid event signal.

Example 75. The medical device of any of examples 72-74 wherein the control circuit is further configured to, in response to determining that the first ventricular event signal is a valid event signal, determine a sensed event time. The control circuit can be further configured to determine an adjusted pacing escape interval having an effective starting time at the sensed event time and restart the pacing escape interval set to the adjusted pacing escape interval having the effective starting time at the sensed event time.

Example 76. The medical device of any of examples 72-75 wherein the sensing circuit is further configured to sense a second ventricular event signal from the second cardiac electrical signal. The control circuit is further configured to determine that the first ventricular event signal is one of a valid event signal or an invalid event signal based on at least a second cardiac electrical signal of the plurality of cardiac electrical signals received during the validation window by: determining that the second ventricular event signal is sensed during the validation window and determining that the second ventricular event signal is sensed by the sensing circuit during the validation window.

Example 77. The medical device of any of examples 72-76 further comprising a memory. The control circuit is further configured to determine that the first ventricular event signal is a valid event signal based on at least the second cardiac electrical signal of the plurality of cardiac electrical signals received during the validation window by: storing a cardiac electrical signal segment from the second cardiac electrical signal in response to the first ventricular event signal being sensed by the sensing circuit, wherein at least a portion of the cardiac electrical signal segment is received during at least a portion of the validation window; determining at least one morphology feature from the cardiac electrical signal segment; determining that the at least one morphology feature from the cardiac electrical signal segment meets R-wave criteria; and determining that the first ventricular event signal is a valid event signal in response to the at least one morphology feature meeting the R-wave criteria.

Example 78. The medical device of example 77 wherein the control circuit is further configured to determine the at least one morphology feature by determining a peak amplitude of the cardiac electrical signal segment, determining a difference signal from the cardiac electrical signal segment and determining a peak-to-peak amplitude of the difference signal. The control circuit can be further configured to determine that the at least one morphology feature meets the R-wave morphology criteria in response to the peak amplitude being greater than an amplitude threshold and the peak-to-peak amplitude of the difference signal being greater than a slope threshold.

Example 79. The medical device of example 78 wherein the control circuit is further configured to determine the peak-to-peak amplitude difference of the difference signal from a portion of the cardiac electrical signal segment that occurs later than the first ventricular event signal.

Example 80. The medical device of any of examples 72-79 wherein the control circuit is further configured to determine that the first ventricular event signal is one of a valid event signal or an invalid event signal based on at least the second cardiac electrical signal of the plurality of cardiac electrical signals by: determining that a second ventricular event signal is not sensed from the second cardiac electrical signal during the validation window; determining at least one morphology feature from a cardiac electrical signal segment of the plurality of cardiac electrical signals, wherein at least a portion of the cardiac electrical signal segment is received during at least a portion of the validation window; determining that the at least one morphology feature does not meet R-wave criteria; and determining that the first ventricular event signal is an invalid event signal in response to determining that a second ventricular event signal is not sensed from the second cardiac electrical signal during the validation window and that the at least one morphology feature does not meet the R-wave criteria.

Example 81. The medical device of any of examples 72-80 wherein the control circuit is further configured to start a hysteresis interval and identify a valid event signal sensed by the sensing circuit during the hysteresis interval based on a first analysis of a first portion of the plurality of cardiac electrical signals. The control circuit can be further configured to restart the hysteresis interval in response to identifying the valid event signal, detect an expiration of the restarted hysteresis interval without identifying a valid event signal during the restarted hysteresis interval, and start the pacing escape interval to schedule the pending cardiac pacing pulse in response to detecting the expiration of the restarted hysteresis interval. The sensing circuit is configured to sense the first ventricular event signal from the first cardiac electrical signal of the plurality of cardiac electrical signals during the pacing escape interval. The control circuit can be further configured to determine that the first ventricular event signal is one of a valid event signal or an invalid event signal based on a second analysis of a second portion of the plurality of cardiac electrical signals including the second cardiac electrical signal, the second analysis different than the first analysis and the first portion of the plurality of cardiac electrical signals different than the second portion of the plurality of cardiac electrical signals.

Example 82. The medical device of example 81 wherein the control circuit is further configured to identify the valid event signal sensed by the sensing circuit during the hysteresis interval based on the first analysis of the first portion of the plurality of cardiac electrical signals by determining a first long-term average maximum amplitude of the first cardiac electrical signal and determining a second long-term average maximum amplitude of the second cardiac electrical signal of the plurality of cardiac electrical signals. The control circuit may further determine if a first peak amplitude of the first cardiac electrical signal is greater than a first threshold amplitude that is based on the first long-term average maximum amplitude and determine if a second peak amplitude of the second cardiac electrical signal is greater than a second threshold amplitude that is based on the second long-term average maximum amplitude. The control circuit may identify the valid event signal sensed by the sensing circuit during the hysteresis interval in response to the first peak amplitude being greater than the first threshold amplitude and the second peak amplitude being greater than the second threshold amplitude.

Example 83. The medical device of any of examples 72-82 wherein the control circuit is further configured to start a hysteresis interval, detect an expiration of the hysteresis interval without identifying a valid event signal during the hysteresis interval and start a tachyarrhythmia analysis interval in response to detecting the expiration of the restarted hysteresis interval before starting the pacing escape interval. The control circuit may be further configured to perform a morphology analysis of at least one of the plurality of cardiac electrical signals received by the sensing circuit during the tachyarrhythmia analysis interval and detect a tachyarrhythmia segment of the at least one of the plurality of cardiac electrical signals based on the morphology analysis. The control circuit may be configured to start a next hysteresis interval in response to detecting the tachyarrhythmia segment without scheduling a pacing pulse.

Example 84. The medical device of any of examples 72-83 wherein the control circuit is further configured to start a hysteresis interval greater than the pacing escape interval, detect an expiration of the hysteresis interval without identifying a valid event signal during the hysteresis interval, and start a pacing duration time interval in response to detecting the expiration of the hysteresis interval. The control circuit can be further configured to start the pacing escape interval to schedule the pending cardiac pacing pulse during the pacing duration time interval, detect an expiration of the pacing duration time interval, and start a next hysteresis interval in response to detecting the expiration of the pacing duration time interval.

Example 85. The medical device of any of examples 72-84 further comprising a housing having a connector block configured to receive a medical lead carrying plurality of extra-cardiac electrodes. The sensing circuit is configured to receive the plurality of cardiac electrical signals via the plurality of the extra-cardiac electrodes. The therapy delivery circuit is configured to deliver the generated pacing pulses via the plurality of extra-cardiac electrodes.

Example 86. A method including starting a pacing escape interval to schedule a pending cardiac pacing pulse, receiving a plurality of cardiac electrical signals and sensing a first ventricular event signal from a first cardiac electrical signal of the plurality of cardiac electrical signals. The method further including starting a validation window in response to sensing the first ventricular event signal, determining that the first ventricular event signal is one of a valid event signal or an invalid event signal based on at least a second cardiac electrical signal of the plurality of cardiac electrical signals received during the validation window, and cancelling the pending cardiac pacing pulse in response to determining that the first ventricular event signal is a valid event signal. The method may further include scheduling a subsequent pending pacing pulse by restarting the pacing escape interval in response to determining that the first ventricular event signal is a valid event signal.

Example 87. The method of example 86 further comprising determining that the pacing escape interval expires during the validation window and withholding the pending cardiac pacing pulse that is scheduled at the expiration of the pacing escape interval in response to the pacing escape interval expiring during the validation window.

Example 88. The method of any of examples 86-87 further comprising delivering the pending cardiac pacing pulse after the validation window in response to determining that the first ventricular event signal is an invalid event signal.

Example 89. The method of any of examples 86-88 further comprising, in response to determining that the first ventricular event signal is a valid event signal, determining a sensed event time. The method further comprising determining an adjusted pacing escape interval having an effective starting time at the sensed event time and restarting the pacing escape interval set to the adjusted pacing escape interval having the effective starting time at the sensed event time.

Example 90. The method of any of examples 86-89 wherein determining that the first ventricular event signal is one of a valid event signal or an invalid event signal based on at least the second cardiac electrical signal of the plurality of cardiac electrical signals received during the validation window comprises sensing a second ventricular event signal from the second cardiac electrical signal, determining that the second ventricular event signal is sensed during the validation window, and determining that the first ventricular event signal is a valid event signal in response to determining that the second ventricular event signal is sensed during the validation window.

Example 91. The method of any of examples 86-90 wherein determining that the first ventricular event signal is a valid event signal based on at least the second cardiac electrical signal of the plurality of cardiac electrical signals received during the validation window comprises storing a cardiac electrical signal segment from the second cardiac electrical signal in response to sensing the first ventricular event signal, wherein at least a portion of the cardiac electrical signal segment is received during at least a portion of the validation window, and determining at least one morphology feature from the cardiac electrical signal segment. The method further comprising determining that the at least one morphology feature from the cardiac electrical signal segment meets R-wave criteria and determining that the first ventricular event signal is a valid event signal in response to the at least one morphology feature meeting the R-wave criteria.

Example 92. The method of example 91 further comprising determining the at least one morphology feature by determining a peak amplitude of the cardiac electrical signal segment, determining a difference signal from the cardiac electrical signal segment, and determining a peak-to-peak amplitude of the difference signal. The method further including determining that the at least one morphology feature meets the R-wave criteria in response to the peak amplitude being greater than an amplitude threshold and the peak-to-peak amplitude of the difference signal being greater than a slope threshold.

Example 93. The method of example 92 further comprising determining the peak-to-peak amplitude difference of the difference signal from a portion of the cardiac electrical signal segment that occurs later than the first ventricular event signal.

Example 94. The method of any of examples 86-93 wherein determining that the first ventricular event signal is one of a valid event signal or an invalid event signal based on at least the second cardiac electrical signal of the plurality of cardiac electrical signals comprises determining that a second ventricular event signal is not sensed from the second cardiac electrical signal during the validation window, and determining at least one morphology feature from a cardiac electrical signal segment of the plurality of cardiac electrical signals, wherein at least a portion of the cardiac electrical signal segment is received during at least a portion of the validation window. The method can further include determining that the at least one morphology feature does not meet R-wave criteria and determining that the first ventricular event signal is an invalid event signal in response to determining that a second ventricular event signal is not sensed from the second cardiac electrical signal during the validation window and that the at least one morphology feature does not meet the R-wave criteria.

Example 95. The method of any of examples 86-94 further comprising starting a hysteresis interval and identifying a valid event signal sensed by the sensing circuit during the hysteresis interval based on a first analysis of a first portion of the plurality of cardiac electrical signals. The method further comprising restarting the hysteresis interval in response to identifying the valid event signal, detecting an expiration of the restarted hysteresis interval without identifying a valid event signal during the restarted hysteresis interval, starting the pacing escape interval to schedule the pending cardiac pacing pulse in response to detecting the expiration of the restarted hysteresis interval and sensing the first ventricular event signal from the first cardiac electrical signal of the plurality of cardiac electrical signals during the pacing escape interval. The method may further include determining that the first ventricular event signal is one of a valid event signal or an invalid event signal based on a second analysis of a second portion of the plurality of cardiac electrical signals including the second cardiac electrical signal, the second analysis different than the first analysis and the first portion of the plurality of cardiac electrical signals different than the second portion of the plurality of cardiac electrical signals.

Example 96. The method of example 95 wherein the first analysis of the first portion of the plurality of cardiac electrical signals comprises determining a first long-term average maximum amplitude of the first cardiac electrical signal and determining a second long-term average maximum amplitude of the second cardiac electrical signal. The method can further include determining if a first peak amplitude of the first cardiac electrical signal is greater than a first threshold amplitude based on the first long-term average maximum amplitude and determining if a second peak amplitude of the second cardiac electrical signal is greater than a second threshold amplitude based on the second long-term average maximum amplitude. The method may include identifying the valid event signal sensed by the sensing circuit during the hysteresis interval based on the first peak amplitude being greater than the first threshold amplitude and the second peak amplitude being greater than the second threshold amplitude.

Example 97. The method of any of examples 86-95 further comprising starting a hysteresis interval, detecting an expiration of the hysteresis interval without identifying a valid event signal during the hysteresis interval and starting a tachyarrhythmia analysis interval in response to detecting the expiration of the hysteresis interval before starting the pacing escape interval. The method may further include performing a morphology analysis of at least one of the plurality of cardiac electrical signals received by the sensing circuit during the tachyarrhythmia analysis interval, detecting a tachyarrhythmia segment of the at least one of the plurality of cardiac electrical signals based on the morphology analysis, and starting a next hysteresis interval in response to detecting the tachyarrhythmia segment without scheduling a pacing pulse.

Example 98. The method of any of examples 86-96 further comprising starting a hysteresis interval greater than the pacing escape interval, detecting an expiration of the hysteresis interval without identifying a valid event signal during the hysteresis interval; and starting a pacing duration time interval in response to detecting the expiration of the hysteresis interval. The method can further include starting the pacing escape interval during the pacing duration time interval, detecting an expiration of the pacing duration time interval, and starting a next hysteresis interval in response to detecting the expiration of the pacing duration time interval.

Example 99. A non-transitory computer-readable medium storing a set of instructions which, when executed by a control circuit of a medical device, cause the medical device to start a pacing escape interval to schedule a pending cardiac pacing pulse, receive a plurality of cardiac electrical signals, sense a ventricular event signal from a first cardiac electrical signal of the plurality of cardiac electrical signals and start a validation window in response to sensing the ventricular event signal. The instructions may further cause the medical device to determine that the ventricular event signal is one of a valid event signal or an invalid event signal based on at least a second cardiac electrical signal of the plurality of cardiac electrical signals received during the validation window and cancel the pending cardiac pacing pulse in response to determining that the first ventricular event signal is a valid event signal. The instructions may further cause the medical device to schedule a subsequent pending pacing pulse by restarting the pacing escape interval in response to determining that the first ventricular event signal is a valid event signal.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

In general, this disclosure describes a medical device and techniques for sensing cardiac event signals and delivering cardiac pacing pulses. The cardiac event signals may be sensed and the cardiac pacing pulses may be delivered via sensing and pacing electrodes implanted at an extra-cardiac location, e.g., carried by an extra-cardiac lead implanted outside the heart and not in direct contact with the heart. The cardiac pacing pulses may be delivered to treat bradycardia, asystole or other cardiac rhythm abnormalities. In various examples, the medical device performing the techniques disclosed herein may be included in an extra-cardiovascular ICD system. As used herein, the term "extra-cardiovascular" refers to a position outside the blood vessels, heart, and pericardium surrounding the heart of a patient. Implantable electrodes carried by extra-cardiovascular leads may be positioned extra-thoracically (outside the ribcage and sternum) or intra-thoracically (beneath the ribcage or sternum) but generally not in intimate contact with myocardial tissue. In other examples, transvenous extra-cardiac leads may carry implantable electrodes that can be positioned intravenously but outside the heart in an extra-cardiac location, e.g., within the internal thoracic vein, jugular vein, or other vein, for sensing cardiac electrical signals and delivering cardiac pacing pulses.

Figure 1A:
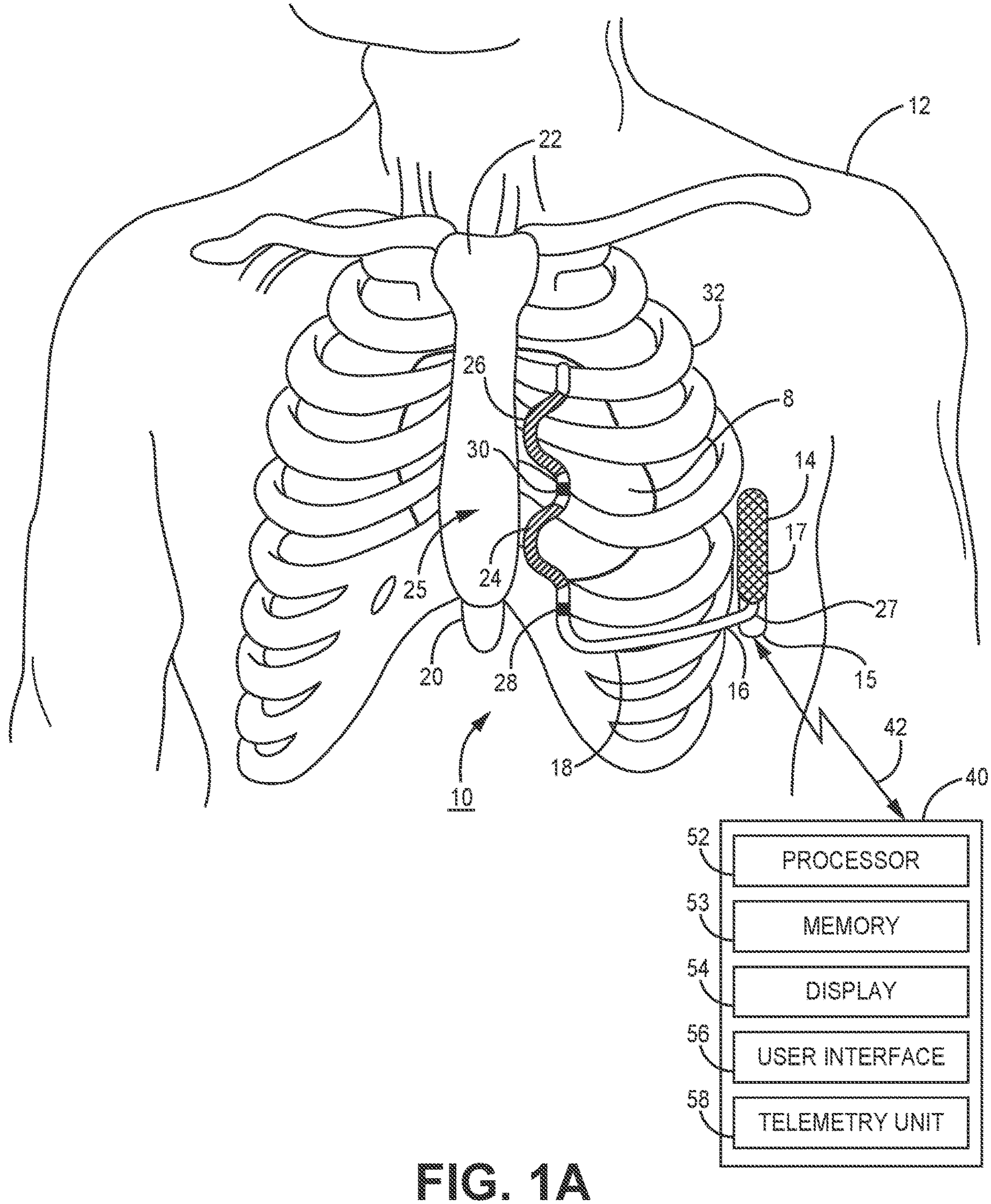
FIGS. 1A and 1B are conceptual diagrams of one example of an extra-cardiovascular ICD system that may be configured to sense cardiac electrical signals and deliver electrical stimulation pulses according to the techniques disclosed herein.
Figure 1B:
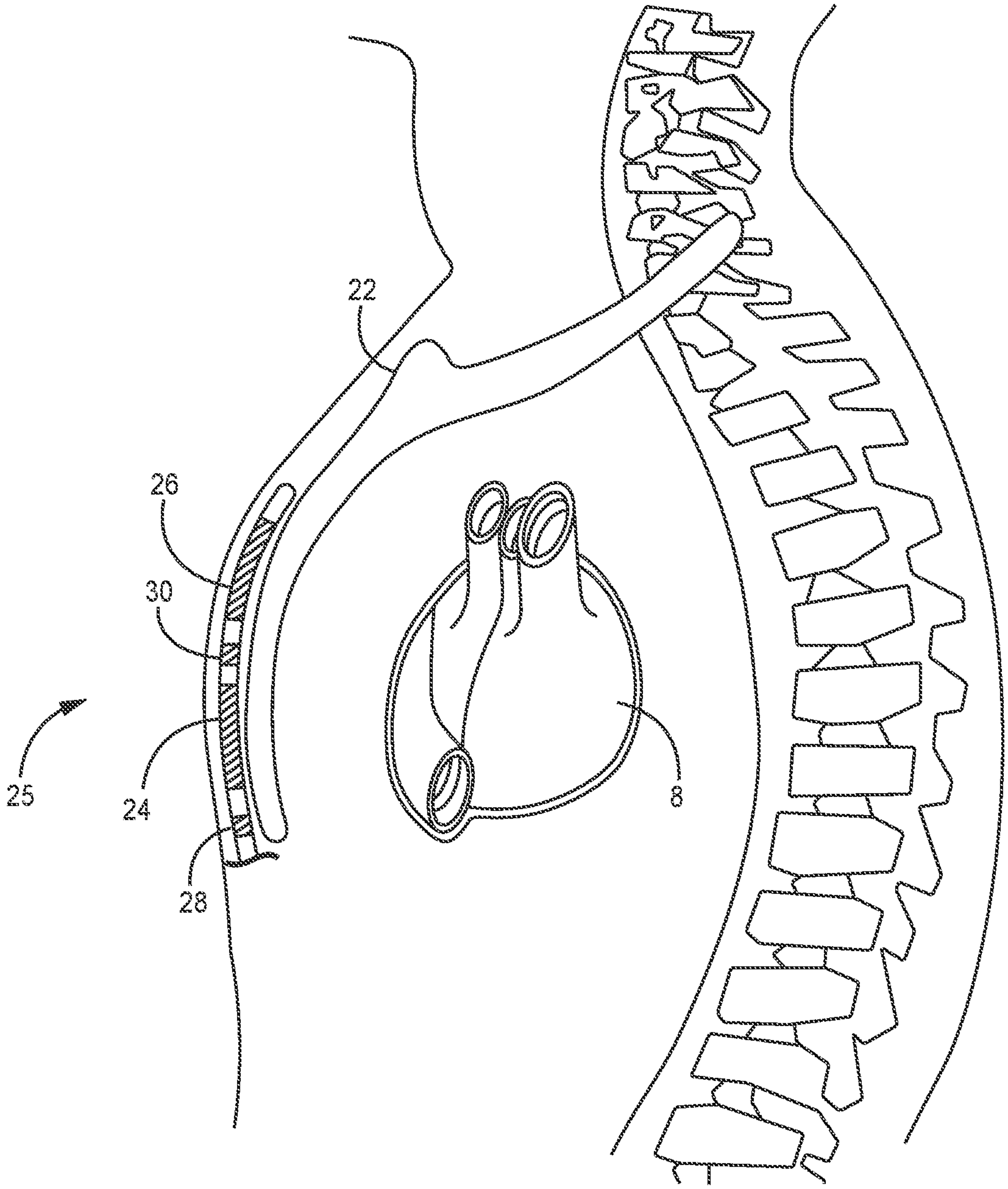

FIGS. 1A and 1B are conceptual diagrams of one example of an extra-cardiovascular ICD system 10 that may be configured to sense cardiac event signals and deliver cardiac electrical stimulation pulses according to the techniques disclosed herein. FIG. 1A is a front view of ICD system 10 implanted within patient 12. FIG. 1B is a side view of ICD system 10 implanted within patient 12. ICD system 10 includes an ICD 14 connected to an extra-cardiovascular electrical stimulation and sensing lead 16. FIGS. 1A and 1B are described in the context of an ICD system 10 capable of providing high voltage CV/DF shocks and cardiac pacing pulses in response to detecting a cardiac arrhythmia based on processing of sensed cardiac electrical signals. The techniques for controlling cardiac sensing and pacing as disclosed herein may be implemented in a device that does not include high voltage CV/DF shock capabilities in some examples. Furthermore, the techniques for controlling cardiac event signal sensing disclosed herein may be implemented in a variety of medical devices including external or implantable cardiac monitors, pacemakers, and ICDs.

ICD 14 includes a housing 15 that forms a hermetic seal that protects internal components of ICD 14. The housing 15 of ICD 14 may be formed of a conductive material, such as titanium or titanium alloy. The housing 15 may function as an electrode (sometimes referred to as a "can" electrode). Housing 15 may be used as an active can electrode for use in delivering CV/DF shocks or other high voltage pulses delivered using a high voltage therapy circuit. In other examples, housing 15 may be available for use in delivering unipolar, relatively lower voltage cardiac pacing pulses and/or for sensing cardiac electrical signals in combination with electrodes carried by lead 16. In other instances, the housing 15 of ICD 14 may include a plurality of electrodes on an outer portion of the housing. The outer portion(s) of the housing 15 functioning as an electrode(s) may be coated with a material, such as titanium nitride, e.g., for reducing post-stimulation polarization artifact.

ICD 14 includes a connector assembly 17 (also referred to as a connector block or header) that includes electrical feedthroughs crossing housing 15 to provide electrical connections between conductors extending within the lead body 18 of lead 16 and electronic components included within the housing 15 of ICD 14. As will be described in further detail herein, housing 15 may house one or more processors, memories, transceivers, cardiac electrical signal sensing circuitry, therapy delivery circuitry, power sources and other components for sensing cardiac electrical signals, detecting a heart rhythm, and controlling and delivering electrical stimulation pulses to treat an abnormal heart rhythm.

Elongated lead body 18 has a proximal end 27 that includes a lead connector (not shown) configured to be connected to ICD connector assembly 17 and a distal portion 25 that includes one or more electrodes. In the example illustrated in FIGS. 1A and 1B, the distal portion 25 of lead body 18 includes defibrillation electrodes 24 and 26 and pace/sense electrodes 28 and 30. In some cases, defibrillation electrodes 24 and 26 may together form a defibrillation electrode in that they may be configured to be activated concurrently. Alternatively, defibrillation electrodes 24 and 26 may form separate defibrillation electrodes in which case each of the electrodes 24 and 26 may be activated independently.

Electrodes 24 and 26 (and in some examples housing 15) are referred to herein as defibrillation electrodes because they are utilized, individually or collectively, for delivering high voltage stimulation therapy (e.g., CV/DF shocks). Electrodes 24 and 26 may be elongated coil electrodes and generally have a relatively high surface area for delivering high voltage electrical stimulation pulses compared to pacing and sensing electrodes 28 and 30. However, electrodes 24 and 26 and housing 15 may also be utilized to provide pacing functionality, sensing functionality or both pacing and sensing functionality in addition to or instead of high voltage stimulation therapy. In this sense, the use of the term "defibrillation electrode" herein should not be considered as limiting the electrodes 24 and 26 for use in only high voltage CV/DF shock therapy applications. For example, either of electrodes 24 and 26 may be used as a sensing electrode in a sensing electrode vector for sensing cardiac electrical signals and determining a need for an electrical stimulation therapy.

Electrodes 28 and 30 are relatively smaller surface area electrodes which are available for use in sensing electrode vectors for sensing cardiac electrical signals and may be used for delivering relatively low voltage pacing pulses in some configurations. Electrodes 28 and 30 are referred to as pace/sense electrodes because they are generally configured for use in low voltage applications, e.g., used as either a cathode or anode for delivery of pacing pulses and/or sensing of cardiac electrical signals, as opposed to delivering high voltage CV/DF shocks. In some instances, electrodes 28 and 30 may provide only pacing functionality, only sensing functionality or both.

ICD 14 may obtain cardiac electrical signals corresponding to electrical activity of heart 8 via a combination of sensing electrode vectors that include combinations of electrodes 24, 26, 28 and/or 30. In some examples, housing 15 of ICD 14 is used in combination with one or more of electrodes 24, 26, 28 and/or 30 in a sensing electrode vector. Various sensing electrode vectors utilizing combinations of electrodes 24, 26, 28, and 30 and housing 15 are described below for sensing cardiac electrical signals, which may include sensing two or more cardiac electrical signals each using a different sensing electrode vector that may be selected by sensing circuitry included in ICD 14. As described herein, the cardiac electrical signal(s) received via a selected sensing electrode vector may be used by ICD 14 for sensing cardiac event signals attendant to intrinsic depolarizations of the myocardium, e.g., R-waves attendant to ventricular depolarization or P-waves attendant to atrial depolarization. Sensed cardiac event signals may be used for determining the heart rate and determining a need for cardiac pacing, e.g., for treating bradycardia or asystole, or for determining a need for tachyarrhythmia therapies, e.g., anti-tachycardia pacing or CV/DF shocks. As described below, one or two sensing electrode vectors may be selected for receiving one or two cardiac electrical signals, respectively, and for sensing ventricular event signals from the cardiac electrical signals. A third sensing electrode vector may be selected for acquiring cardiac electrical signal segments that are analyzed by processing circuitry of ICD 14 for validating ventricular event signals sensed from one or both of the two cardiac electrical signals based on the morphology of the cardiac electrical signal segment.

In the example illustrated in FIGS. 1A and 1B, electrode 28 is located proximal to defibrillation electrode 24, and electrode 30 is located between defibrillation electrodes 24 and 26. One, two or more pace/sense electrodes may be carried by lead body 18. For instance, a third pace/sense electrode may be located distal to defibrillation electrode 26 in some examples. Electrodes 28 and 30 are illustrated as ring electrodes; however, electrodes 28 and 30 may comprise any of a number of different types of electrodes, including ring electrodes, short coil electrodes, hemispherical electrodes, directional electrodes, segmented electrodes, or the like. Electrodes 28 and 30 may be positioned at other locations along lead body 18 and are not limited to the positions shown. In other examples, lead 16 may include fewer or more pace/sense electrodes and/or defibrillation electrodes than the example shown here.

In the example shown, lead 16 extends subcutaneously or submuscularly over the ribcage 32 medially from the connector assembly 27 of ICD 14 toward a center of the torso of patient 12, e.g., toward xiphoid process 20 of patient 12. At a location near xiphoid process 20, lead 16 bends or turns and extends superiorly, subcutaneously or submuscularly, over the ribcage and/or sternum, substantially parallel to sternum 22. Although illustrated in FIG. 1A as being offset laterally from and extending substantially parallel to sternum 22, the distal portion 25 of lead 16 may be implanted at other locations, such as over sternum 22, offset to the right or left of sternum 22, angled laterally from sternum 22 toward the left or the right, or the like. Alternatively, lead 16 may be placed along other subcutaneous or submuscular paths. The path of extra-cardiovascular lead 16 may depend on the location of ICD 14, the arrangement and position of electrodes carried by the lead body 18, and/or other factors. The techniques disclosed herein are not limited to a particular path of lead 16 or final locations of electrodes 24, 26, 28 and 30.

Electrical conductors (not illustrated) extend through one or more lumens of the elongated lead body 18 of lead 16 from the lead connector at the proximal lead end 27 to electrodes 24, 26, 28, and 30 located along the distal portion 25 of the lead body 18. The elongated electrical conductors contained within the lead body 18, which may be separate respective insulated conductors within the lead body 18, are each electrically coupled with respective defibrillation electrodes 24 and 26 and pace/sense electrodes 28 and 30. The respective conductors electrically couple the electrodes 24, 26, 28, and 30 to circuitry, such as a therapy delivery circuit and/or a sensing circuit, of ICD 14 via connections in the connector assembly 17, including associated electrical feedthroughs crossing housing 15. The electrical conductors transmit electrical stimulation pulses from a therapy delivery circuit within ICD 14 to one or more of defibrillation electrodes 24 and 26 and/or pace/sense electrodes 28 and 30 and transmit electrical signals produced by the patient's heart 8 from one or more of defibrillation electrodes 24 and 26 and/or pace/sense electrodes 28 and 30 to the sensing circuitry within ICD 14, such as the sensing circuit 86 shown in FIG. 4.

The lead body 18 of lead 16 may be formed from a non-conductive material, including silicone, polyurethane, fluoropolymers, mixtures thereof, and/or other appropriate materials, and shaped to form one or more lumens within which the one or more conductors extend. Lead body 18 may be tubular or cylindrical in shape. In other examples, the distal portion 25 (or all of) the elongated lead body 18 may have a flat, ribbon or paddle shape. Lead body 18 may be formed having a preformed distal portion 25 that is generally straight, curving, bending, serpentine, undulating or zig-zagging.

In the example shown, lead body 18 includes a curving distal portion 25 having two "C" shaped curves, which together may resemble the Greek letter epsilon, "ε." Defibrillation electrodes 24 and 26 are each carried by one of the two respective C-shaped portions of the lead body distal portion 25. The two C-shaped curves are seen to extend or curve in the same direction away from a central axis of lead body 18, along which pace/sense electrodes 28 and 30 are positioned. Pace/sense electrodes 28 and 30 may, in some instances, be approximately aligned with the central axis of the straight, proximal portion of lead body 18 such that mid-points of defibrillation electrodes 24 and 26 are laterally offset from pace/sense electrodes 28 and 30.

Other examples of extra-cardiovascular leads including one or more defibrillation electrodes and one or more pacing and sensing electrodes carried by curving, serpentine, undulating or zig-zagging distal portion of the lead body 18 that may be implemented with the techniques described herein are generally disclosed in U.S. Pat. No. 10,675,478 (Marshall, et al.), incorporated herein by reference in its entirety. The techniques disclosed herein are not limited to any particular lead body design, however. In other examples, lead body 18 is a flexible elongated lead body without any pre-formed shape, bends or curves.

ICD 14 analyzes the cardiac electrical signals received from one or more sensing electrode vectors to monitor for abnormal rhythms, such as asystole, bradycardia, ventricular tachycardia (VT) or ventricular fibrillation (VF). ICD 14 may analyze the heart rate and morphology of the cardiac electrical signals to monitor for tachyarrhythmia in accordance with any of a number of tachyarrhythmia detection techniques. ICD 14 generates and delivers electrical stimulation therapy in response to detecting a tachyarrhythmia (e.g., VT or VF) using a therapy delivery electrode vector which may be selected from any of the available electrodes 24, 26, 28 30 and/or housing 15. ICD 14 may deliver anti-tachycardia pacing therapy (ATP) in response to VT detection and in some cases may deliver ATP prior to a CV/DF shock or during high voltage capacitor charging in an attempt to avert the need for delivering a CV/DF shock. If ATP does not successfully terminate VT or when VF is detected, ICD 14 may deliver one or more CV/DF shocks via one or both of defibrillation electrodes 24 and 26 and/or housing 15.

In the absence of a ventricular event signal, ICD 14 may generate and deliver a cardiac pacing pulse, such as a post-shock pacing pulse when asystole is detected or bradycardia pacing pulses when a pacing escape interval expires prior to sensing a ventricular event signal. The cardiac pacing pulses may be delivered using a pacing electrode vector that includes one or more of the electrodes 24, 26, 28, and 30 and the housing 15 of ICD 14. Cardiac pacing pulses may be delivered by ICD 14 based on the ventricular event sensing and pacing techniques disclosed herein.

ICD 14 is shown implanted subcutaneously on the left side of patient 12 along the ribcage 32. ICD 14 may, in some instances, be implanted between the left posterior axillary line and the left anterior axillary line of patient 12. ICD 14 may, however, be implanted at other subcutaneous or submuscular locations in patient 12. For example, ICD 14 may be implanted in a subcutaneous pocket in the pectoral region. In this case, lead 16 may extend subcutaneously or submuscularly from ICD 14 toward the manubrium of sternum 22 and bend or turn and extend inferiorly from the manubrium to the desired location subcutaneously or submuscularly. In yet another example, ICD 14 may be placed abdominally. Lead 16 may be implanted in other extra-cardiovascular locations as well. For instance, as described with respect to FIGS. 2A-2C, the distal portion 25 of lead 16 may be implanted underneath the sternum/ribcage in the substernal space. FIGS. 1A and 1B are illustrative in nature and should not be considered limiting in the practice of the techniques disclosed herein.

For example, the medical device performing the techniques disclosed herein may be coupled to an "extra-cardiovascular" lead as illustrated in the accompanying drawings, referring to a lead that positions electrodes outside the blood vessels, heart, and pericardium surrounding the heart of a patient. Implantable electrodes carried by extra-cardiovascular leads may be positioned extra-thoracically (outside the ribcage and sternum) subcutaneously or submuscularly or intra-thoracically (beneath the ribcage or sternum, sometimes referred to as a sub-sternal position) but may not necessarily be in intimate contact with myocardial tissue. An extra-cardiovascular lead may also be referred to as a "non-transvenous" lead.

In other examples, the medical device performing the techniques disclosed herein may be coupled to a transvenous lead that positions electrodes within a blood vessel, which may remain outside the heart in an "extra-cardiac" location or be advanced to position electrodes within a heart chamber. For instance, a transvenous medical lead may be advanced along a venous pathway to position electrodes in an extra-cardiac location within the internal thoracic vein (ITV), an intercostal vein, the superior epigastric vein, or the azygos, hemiazygos, or accessory hemiazygos veins, as examples. In still other examples, a transvenous lead may be advanced to position electrodes within the heart, e.g., within an atrial and/or ventricular heart chamber.

An external device 40 is shown in telemetric communication with ICD 14 by a wireless communication link 42. External device 40 may include a processor 52, memory 53, display 54, user interface 56 and telemetry unit 58. Processor 52 controls external device operations and processes data and signals received from ICD 14. Display unit 54, which may include a graphical user interface, displays data and other information to a user for reviewing ICD operation and programmed parameters as well as cardiac electrical signals retrieved from ICD 14.

User interface 56 may include a mouse, touch screen, keypad or the like to enable a user to interact with external device 40 to initiate a telemetry session with ICD 14 for retrieving data from and/or transmitting data to ICD 14, including programmable parameters for controlling cardiac event signal sensing, arrhythmia detection and therapy delivery. Telemetry unit 58 includes a transceiver and antenna configured for bidirectional communication with a telemetry circuit included in ICD 14 and is configured to operate in conjunction with processor 52 for sending and receiving data relating to ICD functions via communication link 42.

Communication link 42 may be established between ICD 14 and external device 40 using a radio frequency (RF) link such as BLUETOOTH®, Wi-Fi, or Medical Implant Communication Service (MICS) or other RF or communication frequency bandwidth or communication protocols. Data stored or acquired by ICD 14, including physiological signals or associated data derived therefrom, results of device diagnostics, and histories of detected rhythm episodes and delivered therapies, as examples, may be retrieved from ICD 14 by external device 40 following an interrogation command.

External device 40 may be embodied as a programmer used in a hospital, clinic or physician's office to retrieve data from ICD 14 and to program operating parameters and algorithms in ICD 14 for controlling ICD functions. External device 40 may alternatively be embodied as a home monitor or handheld device. External device 40 may be used to program cardiac signal sensing parameters, cardiac rhythm detection parameters and therapy control parameters used by ICD 14. At least some control parameters used in sensing cardiac event signals and controlling cardiac pacing according to the techniques disclosed herein as well as tachyarrhythmia detection and therapy delivery may be programmed into ICD 14 using external device 40 in some examples.

Figure 2A:
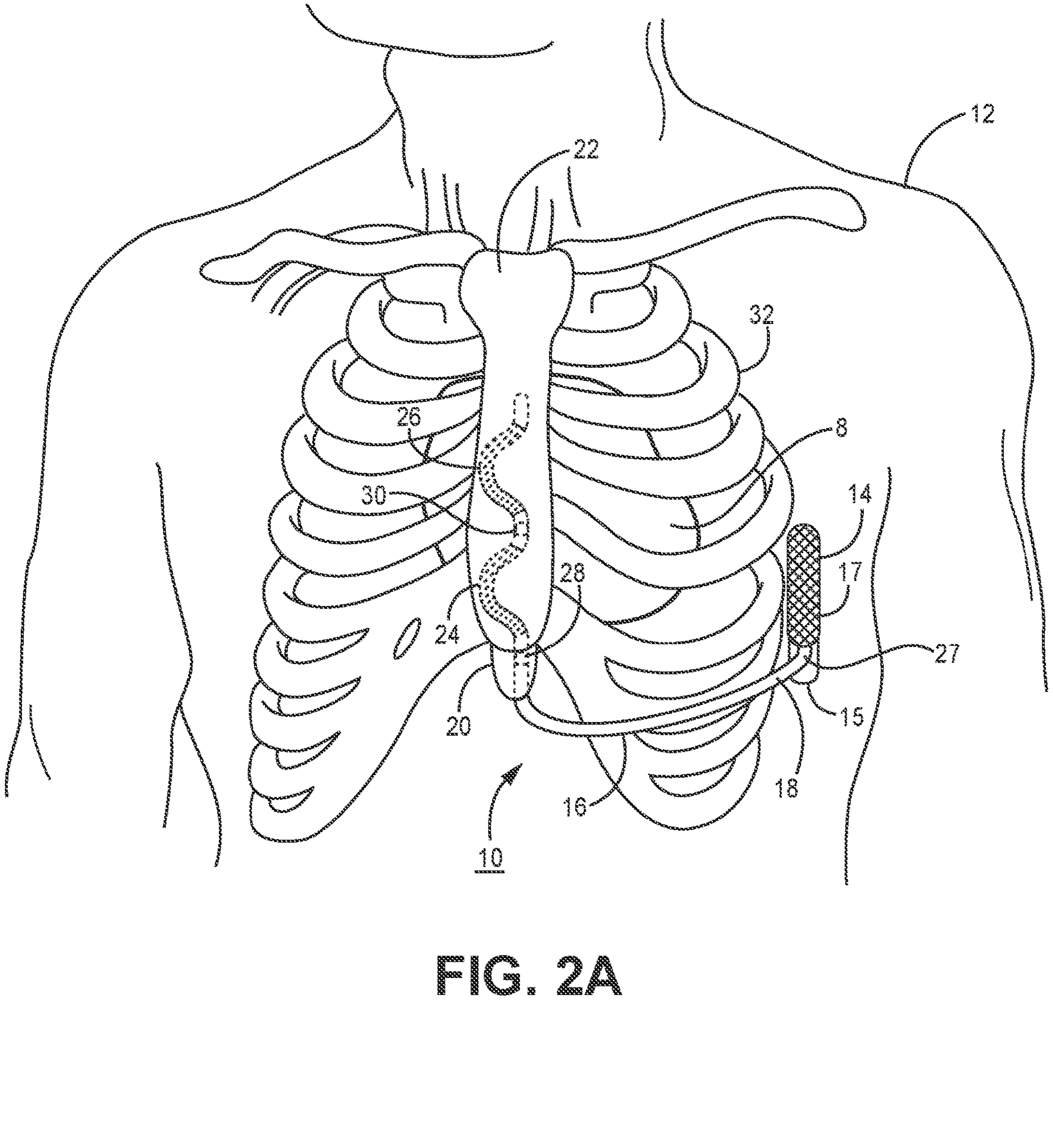
FIGS. 2A-2C are conceptual diagrams of a patient implanted with the extra-cardiovascular ICD system of FIGS. 1A-1B in a different implant configuration than the arrangement shown in FIGS. 1A-1B.
Figure 2B:
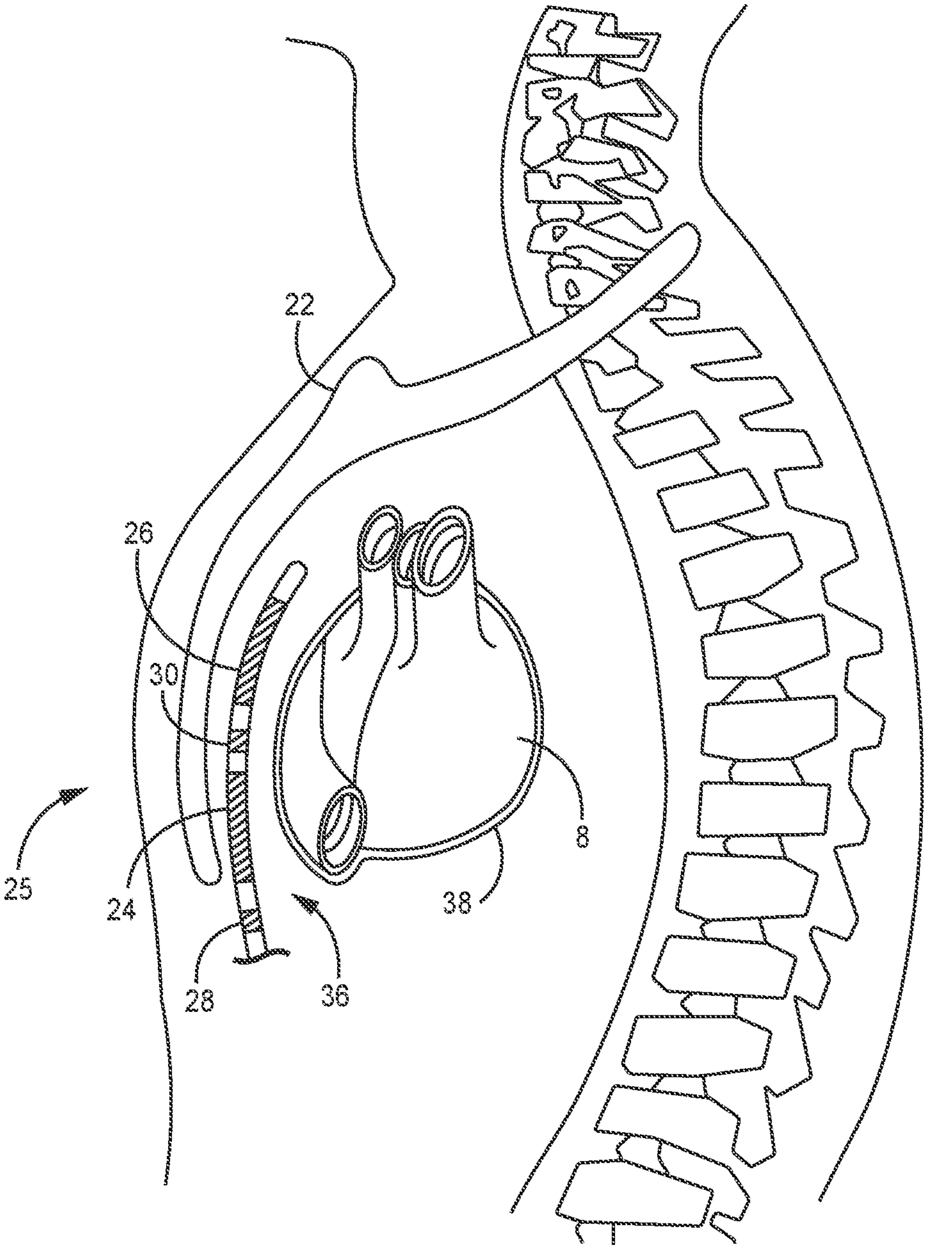
Figure 2C:
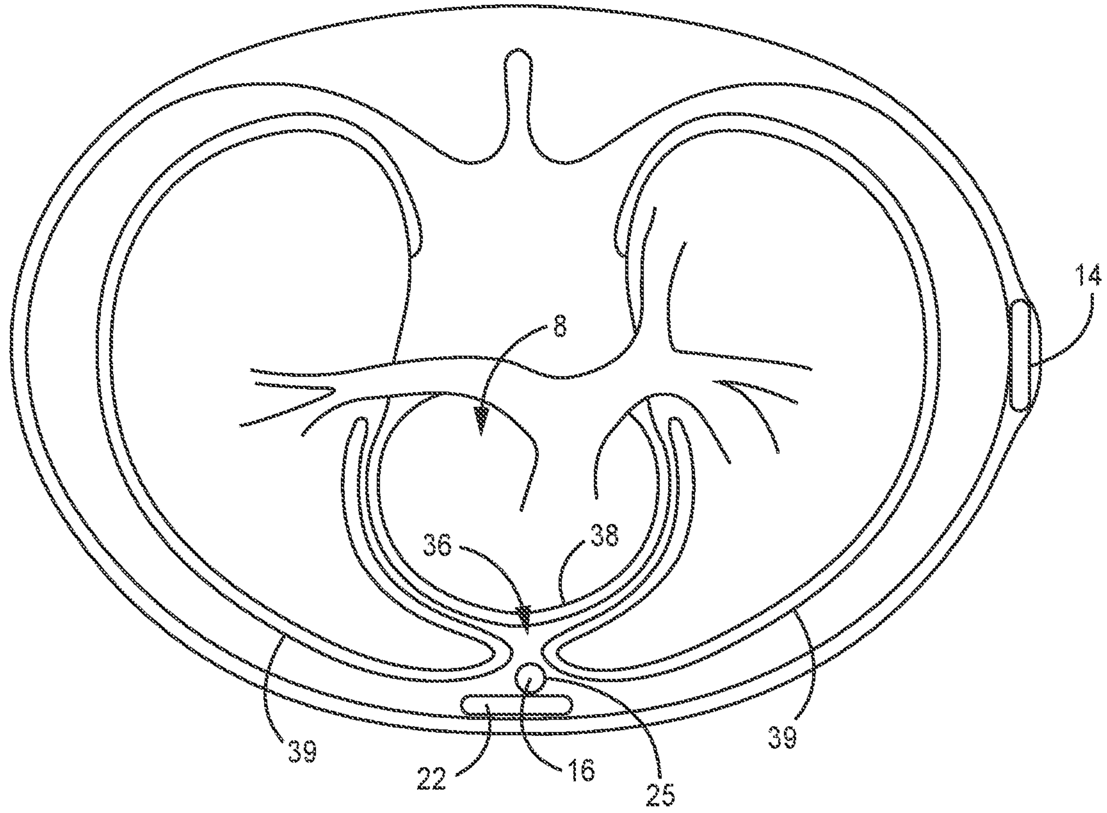

FIGS. 2A-2C are conceptual diagrams of patient 12 implanted with extra-cardiovascular ICD system 10 in a different implant configuration than the arrangement shown in FIGS. 1A-1B. FIG. 2A is a front view of patient 12 implanted with ICD system 10. FIG. 2B is a side view of patient 12 implanted with ICD system 10. FIG. 2C is a transverse view of patient 12 implanted with ICD system 10. In this arrangement, extra-cardiovascular lead 16 of system 10 is implanted at least partially underneath sternum 22 of patient 12. Lead 16 extends subcutaneously or submuscularly from ICD 14 toward xiphoid process 20 and at a location near xiphoid process 20 bends or turns and extends superiorly within anterior mediastinum 36 (see FIG. 2C) in a substernal position.

Anterior mediastinum 36 may be viewed as being bounded laterally by pleurae 39, posteriorly by pericardium 38, and anteriorly by sternum 22 (see FIG. 2C). The distal portion 25 of lead 16 may extend along the posterior side of sternum 22 substantially within the loose connective tissue and/or substernal musculature of anterior mediastinum 36. A lead implanted such that the distal portion 25 is substantially within anterior mediastinum 36, may be referred to as a "substernal lead."

In the example illustrated in FIGS. 2A-2C, lead 16 is located substantially centered under sternum 22. In other instances, however, lead 16 may be implanted such that it is offset laterally from the center of sternum 22. In some instances, lead 16 may extend laterally such that distal portion 25 of lead 16 is underneath/below the ribcage 32 in addition to or instead of sternum 22. In other examples, the distal portion 25 of lead 16 may be implanted in other extra-cardiac, intra-thoracic locations, including in the pleural cavity or around the perimeter of and adjacent to the pericardium 38 of heart 8.

In the various example implant locations of lead 16 and electrodes 24, 26, 28 and 30 shown and described herein, cardiac signals sensed by ICD 14 may have a relatively low and/or variable signal strength, e.g., caused by postural changes, respiration or other body movement, and/or may be contaminated by skeletal muscle myopotentials and/or environmental electromagnetic interference (EMI). Undersensing of R-waves may result in cardiac pacing pulses being delivered when pacing is not needed. Undersensing of R-waves or fibrillation waves may result in an undetected tachyarrhythmia when ATP or CV/DF therapy may be needed. Oversensing of P-waves, T-waves, myopotentials or other noise as R-waves may lead to a false tachyarrhythmia detection or cardiac pacing may be withheld when it is actually needed. Techniques disclosed herein provide improvements in sensing cardiac event signals and control of cardiac pacing in order to avoid delivering unneeded cardiac pacing pulses and avoid withholding cardiac pacing when it is actually needed.

Figure 3:
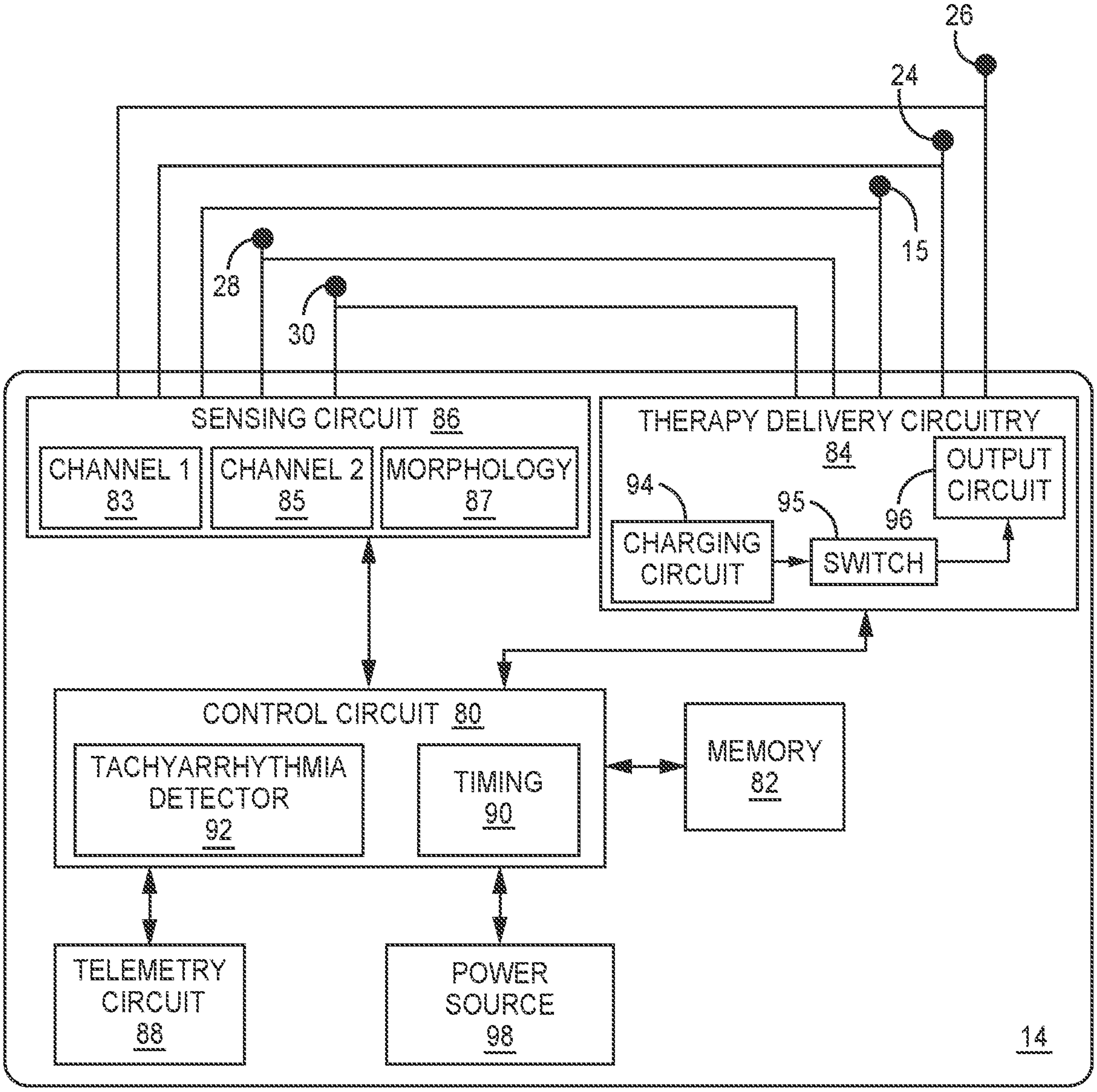
FIG. 3 is a conceptual diagram of an ICD according to one example.

FIG. 3 is a conceptual diagram of ICD 14 according to one example. The electronic circuitry enclosed within housing 15 (shown schematically as an electrode in FIG. 3) includes software, firmware and hardware that cooperatively monitor cardiac electrical signals, determine when an electrical stimulation therapy is necessary, and deliver therapy as needed according to programmed therapy delivery algorithms and control parameters. ICD 14 may be coupled to a lead, such as lead 16 carrying electrodes 24, 26, 28, and 30, for delivering electrical stimulation pulses to the patient's heart and for sensing cardiac electrical signals.

ICD 14 includes a control circuit 80, memory 82, therapy delivery circuit 84, cardiac electrical signal sensing circuit 86, and telemetry circuit 88. A power source 98 provides power to the circuitry of ICD 14, including each of the components 80, 82, 84, 86, and 88 as needed. Power source 98 may include one or more energy storage devices, such as one or more rechargeable or non-rechargeable batteries. The connections between power source 98 and each of the other components 80, 82, 84, 86 and 88 are to be understood from the general block diagram of FIG. 3 but are not shown for the sake of clarity. For example, power source 98 may be coupled to one or more charging circuits included in therapy delivery circuit 84 for charging holding capacitors included in therapy delivery circuit 84 that are discharged at appropriate times under the control of control circuit 80 for producing electrical pulses according to a therapy protocol. Power source 98 is also coupled to components of cardiac electrical signal sensing circuit 86, such as sense amplifiers, analog-to-digital converters, switching circuitry, etc. as needed.

The circuits shown in FIG. 3 represent functionality included in ICD 14 and may include any discrete and/or integrated electronic circuit components that implement analog and/or digital circuits capable of producing the functions attributed to ICD 14 herein. Functionality associated with one or more circuits may be performed by separate hardware, firmware or software components, or integrated within common hardware, firmware or software components. For example, cardiac electrical signal sensing and analysis for detecting bradycardia and tachyarrhythmia may be performed cooperatively by sensing circuit 86 and control circuit 80 and may include operations implemented in a processor or other signal processing circuitry included in control circuit 80 executing instructions stored in memory 82 and control signals such as blanking and timing intervals and sensing threshold amplitude signals sent from control circuit 80 to sensing circuit 86.

The various circuits of ICD 14 may include an application specific integrated circuit (ASIC), an electronic circuit, a processor (shared, dedicated, or group) and memory that execute one or more software or firmware programs, a combinational logic circuit, state machine, or other suitable components or combinations of components that provide the described functionality. The particular form of software, hardware and/or firmware employed to implement the functionality disclosed herein will be determined primarily by the particular system architecture employed in the ICD and by the particular sensing, detection and therapy delivery methodologies employed by the ICD. Providing software, hardware, and/or firmware to accomplish the described functionality in the context of any modern medical device system, given the disclosure herein, is within the abilities of one of skill in the art.

Memory 82 may include any volatile, non-volatile, magnetic, or electrical non-transitory computer readable storage media, such as random access memory (RAM), read-only memory (ROM), non-volatile RAM (NVRAM), electrically-erasable programmable ROM (EEPROM), flash memory, or any other memory device. Furthermore, memory 82 may include non-transitory computer readable media storing instructions that, when executed by one or more processing circuits, cause control circuit 80 and/or other ICD components to perform various functions attributed to ICD 14 or those ICD components. The non-transitory computer-readable media storing the instructions may include any of the media listed above.

Control circuit 80 communicates, e.g., via a data bus, with therapy delivery circuit 84 and sensing circuit 86 for sensing cardiac electrical event signals, detecting cardiac rhythms, and controlling delivery of cardiac electrical stimulation therapies in response to sensed cardiac signals. Therapy delivery circuit 84 and sensing circuit 86 can be electrically coupled to electrodes 24, 26, 28, 30 carried by lead 16 and/or the housing 15, which may function as a common or ground electrode or as an active can electrode for delivering CV/DF shock pulses or cardiac pacing pulses.

Cardiac electrical signal sensing circuit 86 (also referred to herein as "sensing circuit" 86) may be selectively coupled to electrodes 28, 30 and/or housing 15 in order to monitor electrical activity of the patient's heart. Sensing circuit 86 may additionally be selectively coupled to defibrillation electrodes 24 and/or 26 for use in a sensing electrode vector together or in combination with one or more of electrodes 28, 30 and/or housing 15. Sensing circuit 86 may be enabled to selectively receive cardiac electrical signals from at least two different sensing electrode vectors from the available electrodes 24, 26, 28, 30, and housing 15 in some examples. At least three (or more) cardiac electrical signals from three (or more) different sensing electrode vectors may be received simultaneously by sensing circuit 86 in some examples. Sensing circuit 86 may monitor at least one cardiac electrical signal for sensing cardiac event signals, e.g., R-waves attendant to intrinsic myocardial depolarizations. In some examples, sensing circuit 86 may be configured to monitor two cardiac electrical signals simultaneously for sensing cardiac event signals. A third cardiac electrical signal may be received by sensing circuit 86 and passed to control circuit 80 for processing and analysis for determining when a sensed cardiac event signal is a valid event signal or an invalid event signal based on the morphology of the third cardiac electrical signal. For example, sensing circuit 86 may include switching circuitry for selecting which of electrodes 24, 26, 28, 30, and housing 15 are coupled as a first sensing electrode vector to a first sensing channel 83, which electrodes are coupled as a second sensing electrode vector to a second sensing channel 85 of sensing circuit 86 and which electrodes are coupled as a third sensing electrode vector to a morphology signal channel 87.

Each sensing channel 83 and 85 may be configured to amplify, filter and digitize the cardiac electrical signal received from selected electrodes coupled to the respective sensing channel to improve the signal quality for sensing cardiac event signals, such as R-waves. The cardiac event detection circuitry within sensing circuit 86 may include one or more sense amplifiers, filters, rectifiers, threshold detectors, comparators, analog-to-digital converters (ADCs), timers or other analog and/or digital components as described further in conjunction with FIG. 4. A cardiac event sensing threshold may be automatically adjusted by each sensing channel 83 and 85, under the control of control circuit 80, based on sensing threshold control parameters such as timing intervals and sensing threshold amplitude values that may be determined by control circuit 80, stored in memory 82, and/or controlled by hardware, firmware and/or software of control circuit 80 and/or sensing circuit 86.

First sensing channel 83 and second sensing channel 85 may each control a cardiac event sensing threshold, e.g., an R-wave sensing threshold, that is applied to the incoming cardiac electrical signal for sensing cardiac event signals, e.g., R-waves attendant to ventricular depolarizations. Upon sensing a cardiac event signal based on a sensing threshold crossing, first sensing channel 83 may produce a sensed event signal that is passed to control circuit 80. For example, upon detecting an R-wave sensing threshold crossing by the cardiac electrical signal received via a first sensing electrode vector, the first sensing channel 83 may generate a ventricular sensed event signal that is passed to control circuit 80. Similarly, upon detecting an R-wave sensing threshold crossing by a second cardiac electrical signal received by second sensing channel 85, the second sensing channel 85 may generate a ventricular sensed event signal that is passed to control circuit 80. The first and second sensing channels 83 and 85 may be configured to automatically adjust the R-wave sensing threshold used by each channel separately. The ventricular sensed event signals and relative timing from each other may be used by control circuit 80 for validating the ventricular sensed event signals as being true R-waves. The valid ventricular sensed event signals are used by control circuit 80 in controlling cardiac pacing according to the techniques disclosed herein.

The sensed event signals received by control circuit 80 may trigger control circuit 80 to store a time segment of a cardiac electrical signal for processing and analysis for determining morphology features that may be used in validating ventricular sensed event signals as being true R-waves. A time segment of the cardiac electrical signal sensed by the morphology signal channel 87 may buffered in memory 82 in response to a ventricular sensed event signal received from sensing channel 83 or sensing channel 85. Illustrative techniques disclosed herein are described in conjunction with sensing circuit 86 configured to receive two different cardiac electrical signals by the two cardiac event sensing channels 83 and 85, respectively, for sensing R-waves from the two cardiac electrical signals and for receiving a third cardiac electrical signal by morphology signal channel 87 for passing a digitized electrocardiogram (ECG) signal to control circuit 80 for morphology analysis. The three cardiac electrical signals sensed by sensing circuit 86 may be received using three different sensing electrode vectors selected from the available electrodes 24, 26, 28 and 30 and housing 15. However, it is to be understood that cardiac event signal sensing and pacing control techniques disclosed herein may be implemented using more or fewer cardiac electrical signals. For example, two cardiac electrical signals may be received by sensing circuit 86 from two different sensing electrode vectors, with one signal passed to the first sensing channel 83 and the other signal passed to the second sensing channel 85, and either (or both) of the two signals may be passed to control circuit 80 as a multi-bit digital ECG signal used by control circuit 80 for morphology analysis for validating ventricular sensed event signals received from one or both of the first sensing channel 83 and the second sensing channel 85.

Memory 82 may be configured to store a predetermined number of cardiac electrical signal segments in a circulating buffer under the control of control circuit 80, e.g., at least one, two, three or other number of cardiac electrical signal segments. Each segment may be written to memory 82 over a time interval extending before and after a ventricular sensed event signal is generated by the first sensing channel 83 or the second sensing channel 85. Control circuit 80 may access stored cardiac electrical signal segments when validation of ventricular sensed event signals is required, e.g., based on the relative timing of ventricular sensed event signals produced by sensing channels 83 and 85. Validated ventricular sensed event signals are used by control circuit 80 for resetting a pacing escape interval that is used to control the timing and delivery of pacing pulses by therapy delivery circuit 84. Methods that may be performed by sensing circuit 86 and control circuit 80 for validating ventricular sensed event signals for use in controlling cardiac pacing are described below.

The ventricular sensed event signals received from sensing circuit 86 by control circuit 80 may also be used by control circuit 80 for determining sensed event intervals, which may be referred to as RR intervals (or RRIs). An in-channel sensed event interval is the time interval between two ventricular sensed event signals received by control circuit 80 from the same sensing channel 83 or 85. A valid sensed event interval, may be determined by control circuit 80 as the time interval between consecutive valid event signals, which may be associated with ventricular sensed event signals received from one or both sensing channels 83 and 85. Control circuit 80 may include a timing circuit 90 for determining sensed event intervals between consecutive valid event signals and for determining in-channel sensed event intervals between consecutive ventricular sensed event signals received from the same sensing channel. As described below, e.g., in conjunction with FIG. 15, control circuit 80 may be configured to detect alternating valid sensed event intervals and perform morphology analysis for discriminating between possible oversensed event signals and true R-waves when alternating valid event intervals are detected.

Timing circuit 90 may be configured to control various timers and/or counters used to control time intervals or windows used in sensing and validating ventricular event signals and for controlling the timing of cardiac pacing pulses generated by therapy delivery circuit 84. For example, timing circuit 90 may set a timer to apply a validation window during which control circuit 80 analyzes signals received from sensing circuit 86 for validating a ventricular sensed event signal. Timing circuit 90 may start a pacing escape interval in response to a validated ventricular sensed event signal for scheduling a pending cardiac pacing pulse. When the pacing escape interval expires without another ventricular sensed event signal that is determined to be a valid event signal, therapy delivery circuit 84 may generate and deliver a cardiac pacing pulse. Timing circuit 90 may be configured to perform other timing related functions of ICD 14.

Control circuit 80 is also shown to include a tachyarrhythmia detection circuit 92 configured to analyze signals received from sensing circuit 86 for detecting tachyarrhythmia. Tachyarrhythmia detection circuit 92 may detect tachyarrhythmia based on sensed cardiac electrical signals meeting tachyarrhythmia detection criteria. For example, when a threshold number of ventricular sensed event signals each occur at a sensed event interval that is less than a tachyarrhythmia interval, control circuit 80 may detect VT or VF. In some examples, a tachyarrhythmia detection based on the threshold number of ventricular sensed event signals each occurring at a tachyarrhythmia interval may be rejected based on morphology analysis of a cardiac electrical signal. Tachyarrhythmia detection circuit 92 may be implemented in control circuit 80 as hardware, software and/or firmware that processes and analyzes signals received from sensing circuit 86 for detecting VT and/or VF. In some examples, the timing of ventricular sensed event signals received from the first and second sensing channels 83 and 85 is used by timing circuit 90 to determine RRIs between ventricular sensed event signals. Tachyarrhythmia detection circuit 92 may include comparators and counters for counting RRIs determined by timing circuit 90 that fall into various rate detection zones for determining a ventricular rate or performing other rate- or interval-based assessment of ventricular sensed event signals for detecting and discriminating VT and VF.

Tachyarrhythmia detection circuit 92 may be configured to perform other signal analysis for determining if other detection criteria are satisfied before detecting VT or VF based on RRIs, such as R-wave morphology criteria, onset criteria, and noise and oversensing rejection criteria. To support these additional analyses, sensing circuit 86 may pass a digitized ECG signal to control circuit 80, e.g., from morphology signal channel 87, for morphology analysis performed by tachyarrhythmia detection circuit 92 for detecting and discriminating heart rhythms. A cardiac electrical signal received by the morphology signal channel 87 (and/or sensing channel 83 and/or sensing channel 85) may be passed through a filter and amplifier, provided to a multiplexer and thereafter converted to a multi-bit digital signal by an analog-to-digital converter, all included in sensing circuit 86, for storage in memory 82. Memory 82 may include one or more circulating buffers to temporarily store digital cardiac electrical signal segments for analysis performed by control circuit 80. Control circuit 80 may be a microprocessor-based controller that employs digital signal analysis techniques to characterize the digitized signals stored in memory 82 to recognize and classify the patient's heart rhythm employing any of numerous signal processing methodologies for analyzing cardiac signals and cardiac event waveforms, e.g., R-waves.

Therapy delivery circuit 84 includes at least one charging circuit 94, including one or more charge storage devices such as one or more high voltage capacitors and/or low voltage capacitors, and switching circuitry 95 that controls when the charge storage device(s) are discharged through an output circuit 96 across a selected pacing electrode vector or CV/DF shock vector. Charging of capacitors to a programmed pulse amplitude and discharging of the capacitors for a programmed pulse width may be performed by therapy delivery circuit 84 according to control signals received from control circuit 80 for delivering cardiac pacing pulses. As described above, timing circuit 90 may include various timers or counters that control when cardiac pacing pulses are delivered. The microprocessor of control circuit 80 may set the amplitude, pulse width, polarity or other characteristics of cardiac pacing pulses, which may be based on programmed values stored in memory 82.

In response to detecting VT or VF, control circuit 80 may schedule a therapy and control therapy delivery circuit 84 to generate and deliver the therapy, such as ATP and/or CV/DF shocks. Therapy can be generated by initiating charging of high voltage capacitors of charging circuit 94. Charging is controlled by control circuit 80 which monitors the voltage on the high voltage capacitors, which is passed to control circuit 80 via a charging control line. When the voltage reaches a predetermined value set by control circuit 80, a logic signal can be generated on a capacitor full line and passed to therapy delivery circuit 84, terminating charging. A CV/DF pulse is delivered to the heart under the control of the timing circuit 90 by an output circuit 96 of therapy delivery circuit 84 via a control bus. The output circuit 96 may include an output capacitor through which the charged high voltage capacitor is discharged via switching circuitry, e.g., an H-bridge, which determines the electrodes used for delivering the cardioversion or defibrillation pulse and the pulse wave shape.

In some examples, the high voltage therapy circuit configured to deliver CV/DF shock pulses can be controlled by control circuit 80 to deliver pacing pulses, e.g., for delivering ATP, post shock pacing pulses or bradycardia pacing pulses. In other examples, therapy delivery circuit 84 may include a separate low voltage therapy circuit including one or more separate charging circuits, switch circuits and output circuits for generating and delivering relatively lower voltage pacing pulses for a variety of pacing needs and a high voltage therapy circuit for generating and delivering relatively high voltage CV/DF shocks.

Control parameters utilized by control circuit 80 for sensing cardiac event signals, detecting arrhythmias, and controlling therapy delivery may be programmed into memory 82 via telemetry circuit 88. Telemetry circuit 88 includes a transceiver and antenna for communicating with external device 40 (shown in FIG. 1A) using RF communication or other communication protocols as described above. Under the control of control circuit 80, telemetry circuit 88 may receive downlink telemetry from and send uplink telemetry to external device 40.

Figure 4:
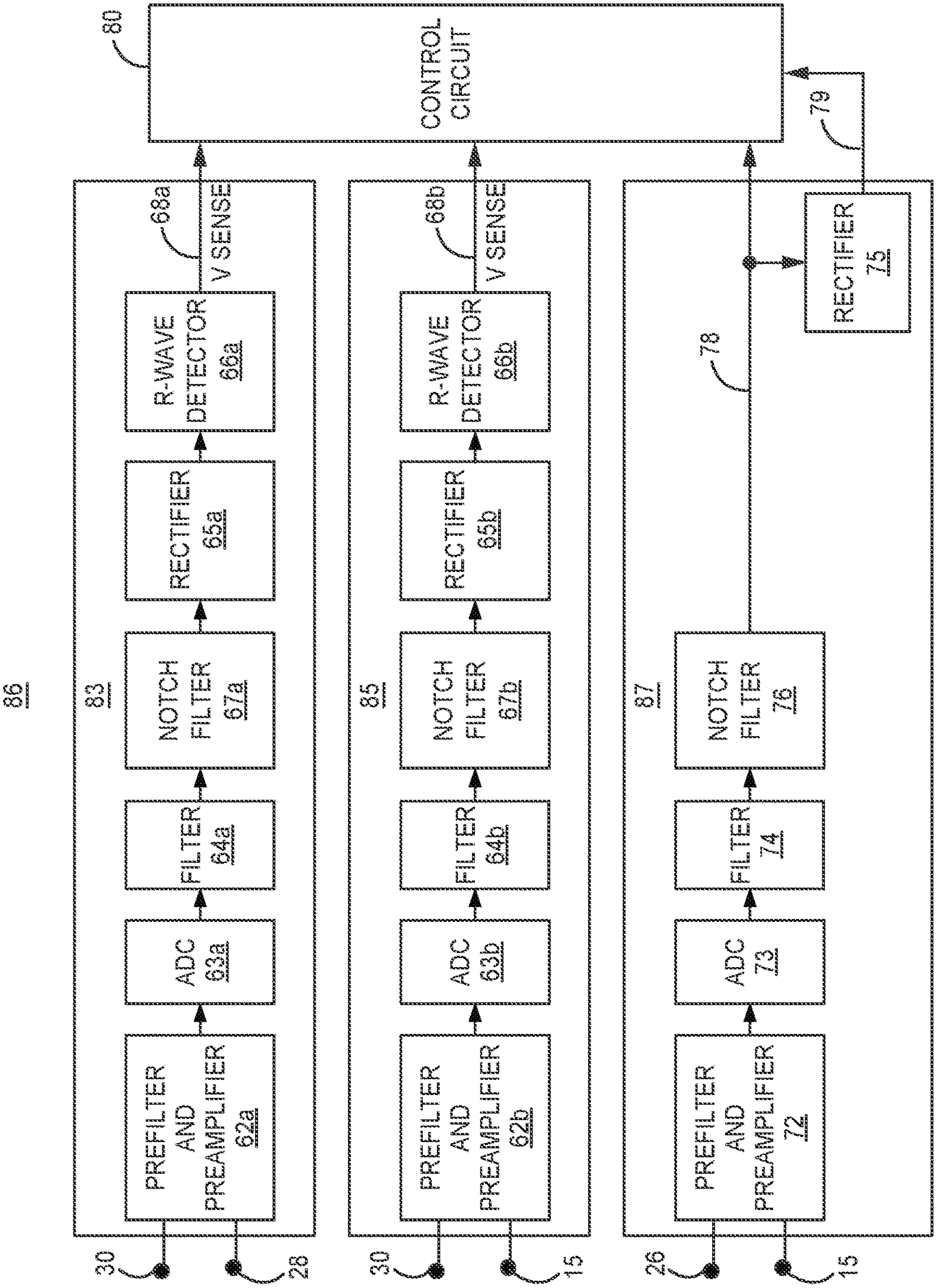
FIG. 4 is a diagram of circuitry that may be included in a sensing circuit of the ICD of FIG. 3.

FIG. 4 is a conceptual diagram of circuitry that may be included in sensing circuit 86 shown in FIG. 3 according to one example. Sensing circuit 86 may include a first sensing channel 83, second sensing channel 85 and morphology signal channel 87 according to one example. First sensing channel 83 and second sensing channel 85 may each be selectively coupled via switching circuitry included in sensing circuit 86 to a respective sensing electrode vector including at least one electrode carried by extra-cardiovascular lead 16. First sensing channel 83 may be coupled to a first sensing electrode vector for receiving a first cardiac electrical signal, and second sensing channel 85 may be coupled to a second sensing electrode vector, different than the first sensing electrode vector for receiving a second cardiac electrical signal, different than the first cardiac electrical signal. In some examples, first sensing channel 83 may be coupled to a sensing electrode vector that is a short bipole, having a relatively shorter inter-electrode distance than the sensing electrode vector coupled to the second sensing channel 85 or to morphology signal channel 87. In the example shown, the first sensing channel 83 is coupled to pace/sense electrodes 28 and 30 carried by lead 16. In some examples, first sensing channel 83 may be coupled to a sensing electrode vector that is approximately vertical (when the patient is in an upright position) or approximately aligned with the cardiac axis to increase the likelihood of a relatively high R-wave signal amplitude relative to P-wave signal amplitude.

The second sensing channel 85 may be coupled to a second sensing electrode vector that is a short bipole or a relatively longer bipole compared to the first sensing electrode vector. The second sensing electrode vector may also be generally vertical or aligned with the cardiac axis. However, the second sensing electrode vector may be orthogonal or transverse relative to the first sensing electrode vector in other examples. In the example shown, the second sensing channel 85 is coupled to pace/sense electrode 30 and housing 15. In other examples, the first or second sensing channels may be coupled to either of pace/sense electrodes 28 or 30 paired with housing 15, either of pace/sense electrodes 28 or 30 paired with coil electrode 24, or either of pace sense electrodes 28 or 30 paired with coil electrode 26, as long as at least one electrode is different between the two sensing electrode vectors. In further examples, either or both of first or second sensing channels 83 or 85 may be coupled to a sensing electrode vector that does not necessarily include one of pace/sense electrodes 28 or 30. For example, a sensing electrode vector may be coupled to sensing channel 83 or sensing channel 85 that includes one or both of coil electrodes 24 or 26 and/or housing 15.

Sensing circuit 86 may include a morphology signal channel 87 for sensing a third cardiac electrical signal in some examples. For instance, morphology signal channel 87 may receive a raw cardiac electrical signal from a third sensing electrode vector, e.g., from a vector that includes one electrode 24, 26, 28 or 30 carried by lead 16 paired with housing 15. Morphology signal channel 87 may be selectively coupled to a relatively long bipole having an inter-electrode distance or spacing that is greater than the sensing electrode vector coupled to first sensing channel 83 or second sensing channel 85 in some examples. The third sensing electrode vector may be, but not necessarily, approximately orthogonal to at least one of the first channel sensing electrode vector or the second channel sensing electrode vector. In the example shown, coil electrode 26 and housing 15 may be coupled to morphology signal channel 85 to provide the third sensed cardiac electrical signal. As described below, the third cardiac electrical signal received by morphology signal channel 87 may be used by control circuit 80 for morphology analysis for validation of a ventricular sensed event signal. In some examples, the sensing electrode vector coupled to morphology signal channel 87 may provide a relatively far-field or more global cardiac signal compared to a relatively shorter bipole that may be coupled to the first sensing channel 83 or the second sensing channel 85. In other examples, any vector selected from the available electrodes, e.g., electrodes 24, 26, 28, 30 and/or housing 15, may be included in a sensing electrode vector coupled to morphology signal channel 87. The sensing electrode vectors coupled to first sensing channel 83, second sensing channel 85 and morphology signal channel 87 may be different sensing electrode vectors, which may have no common electrodes or only one common electrode but not both. In other examples, however, the sensing electrode vector coupled to one of the first sensing channel 83 or the second sensing channel 85 may be the same sensing electrode vector coupled to the morphology signal channel 87. In this case, a sensing channel 83 or 85 and the morphology signal channel 87 may be combined or include shared components such that a morphology signal and ventricular sensed event signals may be output to control circuit 80 from one sensing channel.

The first sensing channel 83 and the second sensing channel 85 may each receive a cardiac electrical signal for sensing ventricular event signals in response to the cardiac electrical signal crossing an R-wave sensing threshold. The morphology signal channel 87 may receive a third cardiac electrical signal for passing a multi-bit digital ECG signal to control circuit 80 for morphology analysis for validating ventricular event signals sensed by the first and/or second sensing channels 83 and 85.

In the illustrative example shown in FIG. 4, the signals received by first sensing channel 83, second sensing channel 85 and morphology signal channel 87 are provided as differential input signals to a pre-filter and pre-amplifier 62*a*, 62*b*, and 72, respectively. Non-physiological high frequency and DC signals may be filtered by a low pass or bandpass filter included in each of pre-filter and pre-amplifiers 62*a*, 62*b* and 72, and high voltage signals may be removed by protection diodes included in pre-filter and pre-amplifiers 62*a*, 62*b* and 72. Pre-filter and pre-amplifiers 62*a*, 62*b* and 72 may amplify the pre-filtered signal by a gain of between 10 and 100, and in one example a gain of 17, though each channel may have a different gain and filter bandwidth. Pre-filter and pre-amplifiers 62*a*, 62*b* and 72 may convert the differential input signal to a single-ended output signal passed to an analog-to-digital converter (ADC) 63*a*, 63*b*, and 73, respectively. Pre-filter and pre-amplifiers 62*a*, 62*b* and 72 may provide anti-alias filtering and noise reduction prior to digitization.

ADC 63*a*, ADC 63*b* and ADC 73, respectively, convert the first cardiac electrical signal, second cardiac electrical signal and third cardiac electrical signal from an analog signal to a digital bit stream, which may be sampled at 128 or 256 Hz, as examples. ADC 63*a*, ADC 63*b* and ADC 73 may be sigma-delta converters (SDC), but other types of ADCs may be used. In some examples, the outputs of ADC 63*a*, ADC 63*b* and ADC 73 may be provided to decimators (not shown), which function as digital low-pass filters that increase the resolution and reduce the sampling rate of the respective cardiac electrical signals.

The digital outputs of ADC 63*a*, ADC 63*b* and ADC 73 are each passed to respective filters 64*a*, 64*b* and 74, which may be digital bandpass filters. The bandpass filters 64*a*, 64*b* and 74 may have the same or different bandpass frequencies. For example, filters 64*a* and 64*b* may have a bandpass of approximately 5 Hz to 60 Hz, 10 Hz to 50 Hz or about 13 Hz to 39 Hz, as examples, for passing cardiac electrical signals such as R-waves typically occurring in this frequency range. Filter 74 of the morphology signal channel 87 may have a relatively wider bandpass of approximately 2.5 to 100 Hz. In some examples, each of sensing channel 83, sensing channel 85 and morphology signal channel 87 may further include a notch filter 67*a*, 67*b*, and 76, respectively, to filter 50 Hz and 60 Hz noise signals.

The narrow bandpass and notch filtered signal in first sensing channel 83 and second sensing channel 85 can be passed to rectifier 65*a* and rectifier 65*b*, respectively, to produce a filtered, rectified signal output to respective R-wave detectors 66*a* and 66*b*. First sensing channel 83 includes an R-wave detector 66*a* for sensing ventricular event signals in response to the first cardiac electrical signal crossing an R-wave sensing threshold. Second sensing channel 85 includes an R-wave detector 66*b* for sensing ventricular event signals in response to the second cardiac electrical signal crossing an R-wave sensing threshold, which may be controlled separately from the R-wave sensing threshold controlled by R-wave detector 66*a*. R-wave detectors 66*a* and 66*b* may each include an auto-adjusting sense amplifier, comparator and/or other detection circuitry that compares the incoming filtered and rectified cardiac electrical signal to an R-wave sensing threshold and produces a ventricular sensed event signal (V Sense) 68*a* or 68*b* when the respective first or second cardiac electrical signal crosses the respective R-wave sensing threshold outside of a post-sense blanking period.

The R-wave sensing threshold may be a multi-level sensing threshold, e.g., as disclosed in commonly assigned U.S. Pat. No. 10,252,071 (Cao, et al.), incorporated herein by reference in its entirety. Example multi-level sensing thresholds are described in conjunction with FIG. 9 below. Briefly, the multi-level sensing threshold may have a starting sensing threshold value held for a time interval, which may be equal to a tachycardia detection interval or expected R-wave to T-wave interval, then drops to a second sensing threshold value held until a drop time interval expires, which may be 1 to 2.5 seconds long and can be 2.15 seconds (from the ventricular sensed event signal) in one example. The drop to the second sensing threshold may be a direct drop made in a one-step decrement or may be multiple steps or a decaying drop. After the drop time interval, the sensing threshold drops to a minimum sensing threshold, which may be equal to a programmed sensitivity and is also referred to herein as the "sensing floor" because it represents the minimum amplitude of the cardiac electrical signal that may be sensed as a ventricular event. The drop to the minimum sensing threshold may be a direct drop made in a one-step decrement or may be multiple steps or a decaying drop. The R-wave sensing thresholds used by R-wave detector 66*a* and 66*b* may each be set to a starting value based on a maximum peak amplitude of the respective first or second cardiac electrical signal determined by the R-wave detector 66*a* or 66*b* during the most recent post-sense blanking period, as described below in conjunction with FIG. 9. In some examples, an R-wave peak tracking period may be defined as a portion of the post-sense blanking period during which the maximum peak amplitude is determined. The starting R-wave sensing threshold of each sensing channel 83 and 85 may decrease over time according to one or more stepwise drops and/or linear or non-linear decay rates until reaching the minimum sensing threshold (or until an R-wave sensing threshold crossing by the cardiac electrical signal occurs).

The techniques described herein are not limited to a specific behavior of the sensing threshold or specific R-wave sensing techniques. Instead, other decaying, stepwise adjusted or other automatically adjusted sensing thresholds may be utilized for sensing ventricular event signals from the respective first and second cardiac electrical signals. R-wave detector 66*a* or 66*b* may produce a ventricular sensed event signal 68*a* or 68*b* in response to the respective first cardiac electrical signal or second cardiac electrical signal crossing the R-wave sensing threshold. The ventricular sensed event signal 68*a* or 68*b* is passed to control circuit 80. As described below, control circuit 80 may validate a ventricular sensed event signal received from sensing circuit 86 based on the relative timing of ventricular sensed signals 68*a* and/or 68*b* received from respective sensing channels 83 and/or 85 and, at least in some instances, based on morphology analysis performed on the ECG signal received from morphology signal channel 87.

Referring to morphology signal channel 87, the wide-band-filtered, digital cardiac electrical signal 78 output from morphology signal channel 87 may be passed to control circuit 80 for morphology analysis. In some examples, the digital cardiac electrical signal 78 is passed to rectifier 75 and a rectified wideband filtered signal 79 is passed to control circuit 80 for processing and analysis. In some cases, both the filtered, non-rectified signal 78 and the rectified signal 79 are passed to control circuit 80 from morphology signal channel 87 for use in determining morphology features of the ECG signal. As described below, an ECG signal segment may be buffered in memory 82 by control circuit 80 in response to a sensed event signal 68*a* or 68*b* received from sensing channel 83 or sensing channel 85. The ECG signal segment may extend over a time interval that encompasses the time point of a ventricular sensed event signal produced by the first sensing channel 83 and/or the second sensing channel 85 so that the ECG signal segment includes a signal corresponding in time to the signal that was sensed by one of the sensing channels 83 or 85. As described herein, control circuit 80 is configured to validate ventricular sensed event signals received from sensing channels 83 and 85 for use in controlling cardiac pacing pulses, e.g., for bradycardia and/or asystole pacing.

The configuration of sensing channels 83 and 85 and morphology signal channel 87 as shown in FIG. 4 is illustrative in nature and should not be considered limiting of the techniques described herein. Sensing circuit 86 may include more or fewer components than illustrated and described in conjunction with FIG. 4 and some components may be shared between sensing channels 83 and 85 and morphology signal channel 87. For example, a common cardiac electrical signal from a selected sensing electrode vector may be received by a prefilter and preamplifier circuit and ADC and subsequently be passed to a narrowband filter in one of sensing channels 83 or 85 and to a wideband filter in morphology signal channel 87. In other examples, sensing circuit 86 may include more than two sensing channels, each configured to produce ventricular sensed event signals, and/or more than one morphology signal channel. Furthermore, the components for filtering, amplifying, digitizing, rectifying, etc. may be arranged in a different order or combination than shown in FIG. 4.

Figure 5:
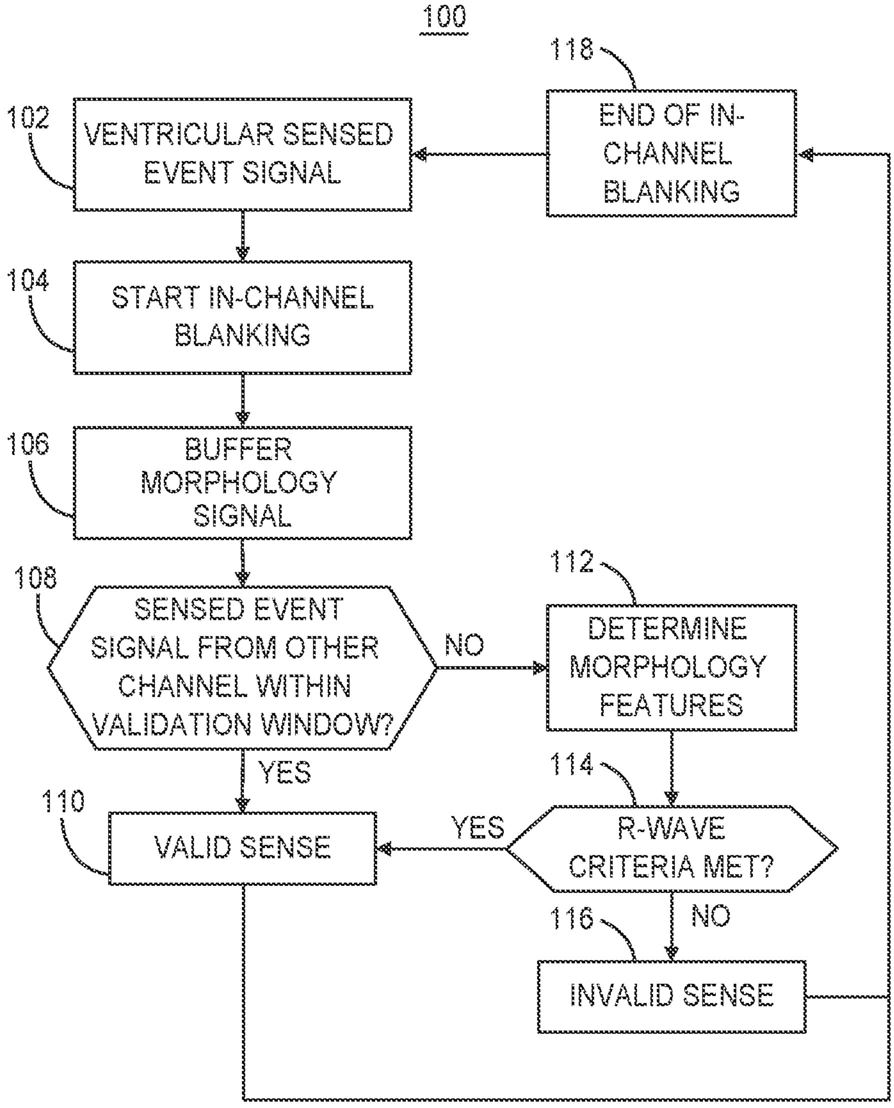
FIG. 5 is a flow chart of a method that may be performed by the ICD of FIG. 3 for validating a ventricular sensed event signal according to one example.

FIG. 5 is a flow chart 100 of a method that may be performed by sensing circuit 86 and control circuit 80 for validating a ventricular sensed event signal according to one example. At block 102, control circuit 80 receives a ventricular sensed event signal from either the first sensing channel 83 or the second sensing channel 85. The ventricular sensed event signal is received after a preceding post-sense or post-pace blanking period and is the first or earliest ventricular sensed event signal since a preceding pacing pulse or validated ventricular sensed event signal. At block 104, the sensing channel 83 or 85 starts a post-sense blanking period following the R-wave sensing threshold crossing that caused the R-wave detector (66*a* or 66*b* in FIG. 4) to produce the ventricular sensed event signal. The blanking period may be referred to as an "in-channel" blanking period because it is applied to the sensing channel 83 or 85 that produced the ventricular sensed event signal received at block 102. The other sensing channel (85 or 83) continues to apply the auto-adjusting R-wave sensing threshold to the other cardiac electrical signal until a sensing threshold crossing occurs (or a cardiac pacing pulse is delivered).

At block 106, control circuit 80 buffers the ECG signal received from the morphology signal channel 87 in response to receiving the ventricular sensed event signal from one of sensing channels 83 or 85. The ECG signal may be buffered to memory 82 continuously at a desired sampling rate prior to control circuit 80 receiving a ventricular sensed event signal at block 102. Memory 82 may include a first-in-first-out (FIFO) buffer allocated to store a predetermined time interval of the ECG signal, e.g., approximately 70 to 150 ms or about 100 ms as examples. In one example, the FIFO buffer can be configured to store the most recent 98 ms of the ECG signal, or 25 sample points at a sampling rate of 256 Hz. This FIFO buffer may operate continuously until a sensed event signal is received such that at any given time the most recent predetermined time interval (e.g., n-ms time interval of y sample points) of the ECG signal from the morphology signal channel 87 is stored in the buffer. The 25 sample points in the example given above can include 24 sample points prior to receiving the ventricular sensed event signal and the sample point at the time point of the ventricular sensed event signal.

Upon receiving the ventricular sensed event signal from one of the sensing channels 83 or 85, control circuit 80 may freeze the FIFO buffer to hold the most recent 98 ms (or other n ms time interval) of the ECG signal received from morphology signal channel 87. This time interval of the ECG signal is a first portion of an ECG signal segment that is buffered in memory 82 in response to receiving the ventricular sensed event signal. Control circuit 80 may store a next predetermined time interval of the ECG signal in memory 82 as a second portion of the ECG signal segment. The second portion of the ECG signal segment may be appended to the first portion of the ECG signal segment stored in the FIFO buffer. For example, an additional 50 to 150 ms of the ECG signal may be stored in memory 82 to provide an ECG signal segment that encompasses the time of the ventricular sensed event signal. The total ECG signal segment may be 120 to 300 ms long in some examples. For instance, an additional 90 ms of the ECG signal, or 23 samples at the sampling rate of 256 Hz, may be stored in memory 82 after receiving a ventricular sensed event signal. A first portion that is 98 ms and a second portion that is 90 ms provides a 188 ms ECG signal segment that is available for morphology analysis by control circuit 80 if needed to validate the ventricular sensed event signal that triggered the ECG signal segment storage.

In other examples, memory 82 may be configured to continuously store in a FIFO buffer a specified number of sample points, e.g., 100 to 1,000 sample points, 300 to 600 sample points, or 512 sample points in an example. When a ventricular sensed event signal is received, control circuit 80 and memory 82 may cooperatively operate to continue buffering sample points in the FIFO buffer to obtain the remaining sample points needed to complete the ECG signal segment having a desired length (e.g., desired number of sample points), including a first portion of sample points buffered before the ventricular sensed event signal is received and a second portion of sample points buffered after the ventricular sensed event signal is received. When the second portion of sample points have been accumulated in the FIFO buffer, the complete ECG signal segment, which may be only a portion of the total number of sample points stored in the FIFO buffer, may be moved to a temporary buffer for storing the ECG signal segment. In this way, at least a portion of the ECG signal segment is received during at least a portion of the validation window. Control circuit 80 may access the stored ECG signal segment for performing various calculations and morphology analysis as needed for validating the associated ventricular sensed event signal.

At block 108, control circuit 80 determines if a ventricular sensed event signal is received from the other sensing channel within a validation window of time after the first ventricular sensed event signal received at block 102. For the sake of illustration, if the first sensing channel 83 produces a ventricular sensed event signal at block 102, control circuit 80 may start a timer set to the validation window duration to determine if a second ventricular sensed event signal is received from the second sensing channel 85 within the validation window. The validation window may be set to 80 to 130 ms or about 105 ms as examples, though longer or shorter windows could be used. When a first one of sensing channels 83 or 85 produces a first, earliest ventricular sensed event signal (outside of a post-sense or post-pace blanking period and after the expiration of any previously started validation window) and the second one of the sensing channels 85 or 83 produces a second, later ventricular sensed event signal within the validation window started in response to the first, earliest ventricular sensed event signal, control circuit 80 determines that the first (and second) ventricular sensed event signals together represent a valid event signal at block 110. The second, later ventricular sensed event signal is produced by the second one of the sensing channels 85 or 83 outside of any in-channel blanking period.

In some examples, control circuit 80 does not perform morphology analysis of the buffered ECG signal for validating the two ventricular sensed event signals that are sensed within the validation window of each other. The ECG signal buffered (or in the process of being buffered) in response to the first, earliest ventricular sensed event signal may be discarded (or the process aborted) when the second ventricular sensed event signal is received within the validation window in some examples. The FIFO buffer may be unfrozen so that the ECG signal may be sampled and stored in the FIFO buffer until the next ventricular sensed event signal is received outside of a blanking period and previously started validation window.

When more than two sensing channels are included in sensing circuit 86, a ventricular sensed event signal may be required to be received from at least two, at least n−1 where n is the number of sensing channels, or all of the sensing channels within the validation window in order to validate the first, earliest ventricular sensed event signal in various examples. Two or more ventricular sensed event signals received from two or more sensing channels within a validation window may be collectively determined to be a valid event signal by control circuit 80. Morphology analysis for validating a ventricular sensed event signal may be performed by control circuit 80 when fewer than all of the sensing channels produce a ventricular sensed event signal within the validation window from each other. However, under some conditions as described below, control circuit 80 may perform morphology analysis on a buffered ECG signal segment corresponding to one or more ventricular sensed event signals even when at least one ventricular sensed event signal is received within the validation window following a first, earliest ventricular sensed event signal.

If the validation window expires at block 108 without a second, later ventricular sensed event signal received from the other sensing channel, control circuit 80 may determine one or more morphology features from the buffered ECG signal segment at block 112. Examples of morphology features that may be determined at block 112 from the ECG signal received from the morphology signal channel 87 are described below, e.g., in conjunction with FIG. 6. In some examples, a morphology matching score is determined by comparing the morphology of the buffered ECG signal segment to a previously established normal R-wave template, which may be stored in memory 82. Control circuit 80 may additionally or alternatively determine a peak amplitude, peak-to-peak amplitude, peak slope, difference between a maximum slope and a minimum slope, signal width, signal area, number of peaks, peak polarity(ies), number of zero crossings or any combination thereof as examples of other morphology features that may be determined at block 112.

At block 114, control circuit 80 compares the determined morphology features to R-wave criteria. The R-wave criteria includes a threshold, range or other defined value for a given ECG signal morphology feature that corresponds to a true R-wave. The R-wave criteria may include a threshold, range or other defined value for each of multiple ECG signal morphology features that may be required to be met by the morphology features determined at block 112. The R-wave criteria may require that the threshold, range or other defined value for each one of multiple morphology features be satisfied according to AND, OR, IF/THEN or other logical operations. When the R-wave criteria are met, the ECG signal segment includes a true R-wave signal with a high degree of probability. For example, the R-wave criteria may include a morphology matching score threshold. When the morphology matching score determined between the ECG signal segment and previously established R-wave template stored in memory 82 is greater than the matching score threshold, control circuit 80 may determine that a ventricular sensed event signal from a single sensing channel 83 or 85 is a valid event signal (valid sense) at block 110. Other R-wave criteria that may be applied at block 114 for validating a ventricular sensed event signal received from a single sensing channel 83 or 85 within the validation window are described below, e.g., in conjunction with FIG. 6. Control circuit 80 determines that the ventricular sensed event signal received from a single sensing channel 83 or 85 within the validation window is an invalid event signal (invalid sense) at block 116 when control circuit 80 determines that the R-wave criteria at block 114 are not met by the morphology features determined at block 112 (and a second, later ventricular sensed event signal is not received from the other sensing channel within the validation window).

After determining whether a ventricular sensed event signal is a valid event signal (block 110) or an invalid event signal (block 116), control circuit 80 returns to block 102 to wait for the next ventricular sensed event signal. Each sensing channel 83 and 85 applies a post-sense (in-channel) blanking period if an R-wave sensing threshold crossing is detected by the given channel resulting in a ventricular sensed event signal being generated by that channel. In some examples, if a ventricular sensed event signal is generated by one sensing channel 83 or 85, an in-channel post-sense blanking period is started by the R-wave detector of that channel but no blanking period is started in the other sensing channel that did not generate a ventricular sensed event signal. If a blanking period has been started in a sensing channel 83 or 85, the sensing channel 83 or 85 waits for the respective blanking period to end at block 118 before another R-wave sensing threshold crossing can be detected and a ventricular sensed event signal can be generated at block 102. Furthermore, a ventricular sensed event signal that occurs within a validation window that has already been started does not start a new validation window or restart a new validation window in some examples.

In other examples, a new validation window may be started in response to the second, later ventricular sensed event signal. In some instances, the first, earlier sensed event signal may be noise or oversensing and could be falsely validated by a second, later ventricular sensed event signal from the other sensing channel within the validation window. However, as described below, in some examples, depending on the relative timing of two ventricular sensed event signals that occur within a validation window, other criteria may be applied before validating the first, earlier sensed event signal. Other criteria may include morphology analysis that may indicate that the first, earliest ventricular sensed event signal is noise or otherwise unlikely to be a true R-wave. In this case, when a new validation window is started by control circuit 80 in response to the second, later ventricular sensed event signal, the second, later ventricular sensed event signal could still potentially be determined to be a valid event signal.

Figure 6:
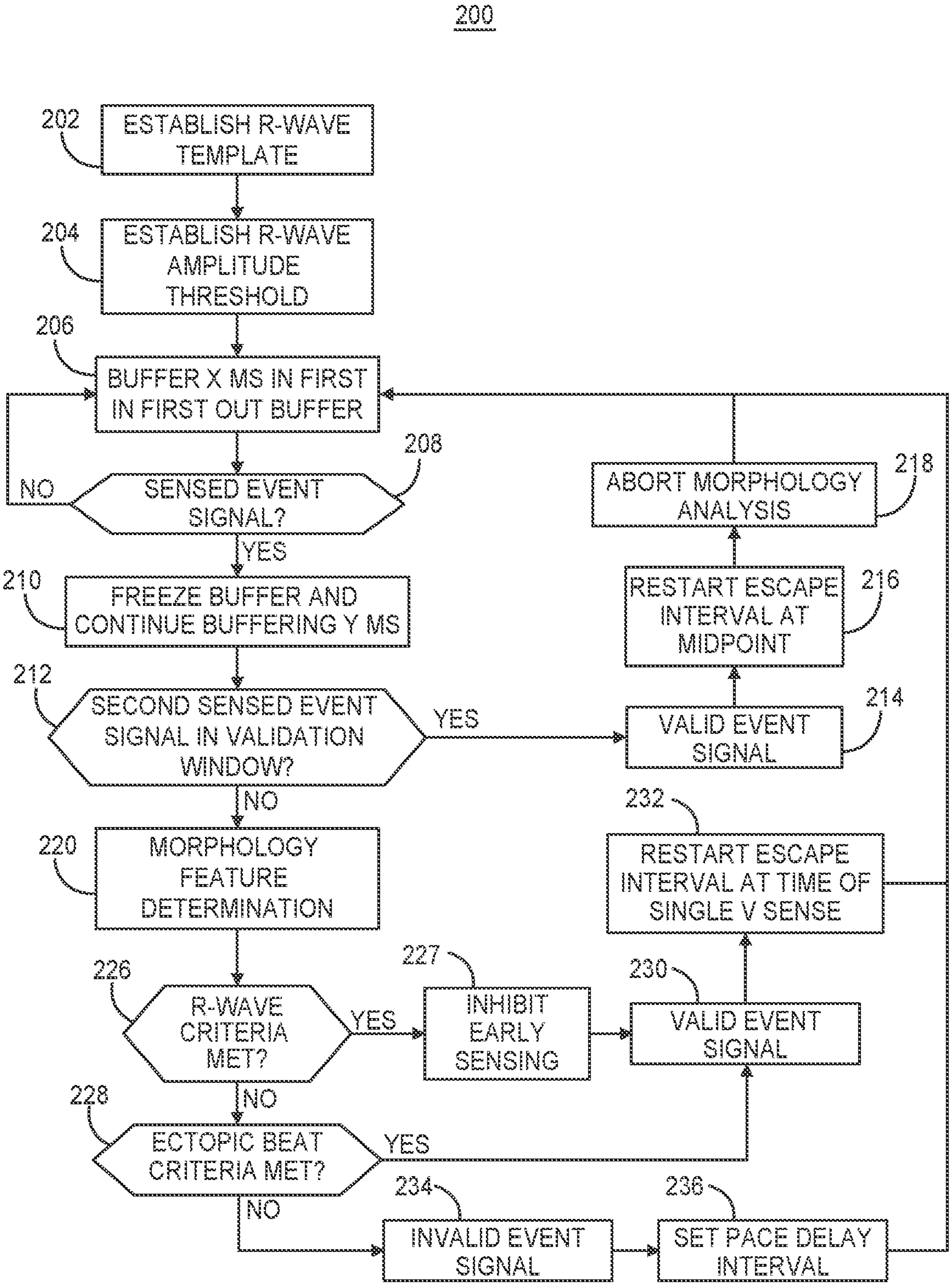
FIG. 6 is a flow chart of a method that may be performed by the ICD of FIG. 3 for validating ventricular sensed event signals and controlling a pacing escape interval according to some examples.

FIG. 6 is a flow chart 200 of a method for validating ventricular sensed event signals and controlling a pacing escape interval according to some examples. Initially, control circuit 80 may determine morphology feature reference values for known, valid R-waves determined from the ECG signal, received from the morphology signal channel 87. The morphology feature reference values may be used for comparison to analogous features determined from ECG signal segments for validating ventricular sensed event signals or establishing threshold, ranges or other values of the R-wave criteria. For example, control circuit 80 may establish an R-wave template at block 202 by performing a wavelet transform, e.g., a Haar transform or other transform method, on one or more ECG signal segments that are received from the morphology signal channel 87 when both sensing channels 83 and 85 pass a ventricular sensed event signal within the validation window and the heart rate is a resting heart rate. In other examples, a clinician or other user may confirm valid R-wave sensing using external device 40 during an R-wave morphology feature determination process. In one example, control circuit 80 may perform a wavelet transform on a series of ECG signal segments (e.g., 3 to 8 segments or 6 segments in one example) that are received from the morphology signal channel 87 when both sensing channels 83 and 85 pass a ventricular sensed event signal within the validation window. A cross-correlation analysis of these signal segments and/or a cross-correlation analysis of the wavelet coefficients determined from the signal segments may be performed to establish the similarity of the signal segments in the series. When the series of segments are determined to match each other based on the cross-correlation analysis, an R-wave template may be established based on a combination of the signal segments, e.g., by ensemble averaging of the signal segments and determining wavelet coefficients from the template and/or averaging the wavelet coefficients determined for the series of signal segments. The established R-wave template and/or corresponding wavelet coefficients may be stored in memory 82. The techniques disclosed herein are not necessarily limited to a particular waveform morphology matching technique and other waveform correlation analyses or morphology matching techniques may be used for establishing a template and for determining when an ECG signal segment matches the R-wave template.

At block 204, an R-wave criteria threshold, range or other value can be established based on another feature of the established R-wave template. In the example shown, an R-wave amplitude threshold is established, e.g., based on the maximum peak amplitude of the R-wave template established at block 202. In other examples, the mean or median or other metric of the maximum peak amplitudes of the series of ECG signal segments used to establish the template may be determined by control circuit 80 and used to establish an R-wave amplitude threshold at block 204. The maximum peak amplitude may be determined as the maximum peak amplitude of the rectified ECG signal segments (or absolute value of the largest positive or negative peak of the non-rectified ECG signal segment).

In other examples, one or more thresholds, ranges or other values may be established as R-wave criteria at block 204 based on a value of a corresponding R-wave morphology feature determined by control circuit 80 from the established R-wave template or from one or more ECG signal segments determined as valid R-wave segments. In another example, a first order difference signal may be determined from the established R-wave template for determining a peak-to-peak amplitude of the first order difference signal, which can represent the difference between a maximum slope and a minimum slope of the valid R-wave ECG signal segment(s), also referred to herein as the "slope difference." A threshold or range of the slope difference may be established as R-wave criteria for validating a ventricular sensed event signal in some examples.

At block 206, control circuit 80 receives the ECG signal from morphology signal channel 87 and stores the sampled, digital signal in memory 82 as described above, e.g., in a FIFO buffer. The most recent 80 to 120 ms of the ECG signal may be stored. The buffered ECG signal sample points are overwritten in a FIFO basis until control circuit 80 receives a ventricular sensed event signal at block 208. When control circuit 80 receives a ventricular sensed event signal from either one of sensing channels 83 or 85, control circuit 80 freezes the buffered ECG signal sample points in memory 82 at block 210 and continues to buffer the next Y ms of the ECG signal to obtain an ECG signal segment over a predetermined time interval that encompasses the ventricular sensed event signal. As described above, an additional 50 to 100 ms may be buffered to obtain a 120 to 200 ms ECG signal segment encompassing the time of the ventricular sensed event signal, as examples. In other examples, as described above, a specified number of sample points of the ECG signal may be continuously buffered in a FIFO buffer and when a ventricular sensed event signal is received, an ECG signal segment may be moved from the FIFO buffer to a temporary buffer after the second post-sense portion of the ECG signal sample points have been obtained to complete the desired length (total number of sample points) of the ECG signal segment. At least a portion of the ECG signal segment is received during at least a portion of a validation window that is started by control circuit 80 in response to the ventricular sensed event signal received at block 208.

In response to receiving the ventricular sensed event signal at block 208 from one sensing channel 83 or 85, control circuit 80 may start a timer or counter to determine if a second ventricular sensed event signal from the other one of the sensing channels 85 or 83 is received within a validation window of time. If a second ventricular sensed event signal is received before the validation window expires, control circuit 80 determines that the first ventricular sensed event signal (and the second ventricular sensed event signal) is a valid event signal corresponding to a true R-wave at block 214. Control circuit 80 restarts a pacing escape interval at block 216 in response to the valid event signal.

Based on the first and second ventricular sensed event signals, control circuit 80 may determine a sensed event time. The pacing escape interval may be restarted to have an effective starting time coincident with the determined sensed event time. For example, as shown in the non-limiting example of FIG. 6, control circuit 80 may determine the sensed event time to be a midpoint between the two ventricular sensed event signals received within the validation window from each other. The pacing escape interval may be restarted at block 216 to have an effective starting time corresponding to the midpoint between the first and second ventricular sensed event signals in some examples. For example, control circuit 80 may set the pacing escape interval to an adjusted value equal to the pacing escape interval less the time elapsed from a midpoint between the two ventricular sensed event signals to the second ventricular sensed event signal (the time at which control circuit 80 makes the valid event signal determination). To illustrate, if the programmed lower pacing rate is 60 beats per minute, the corresponding pacing escape interval is 1 second. If the second ventricular sensed event signal occurs 80 ms after the first ventricular sensed event signal, the midpoint is 40 ms earlier than the second ventricular sensed event signal. The pacing escape interval may be adjusted to 1 second less the time to the midpoint, e.g., 1 second less 40 ms or 960 ms, to have an effective starting time coinciding with the midpoint between the first and second ventricular sensed event signals. In this way, the pacing escape interval restarted by control circuit 80 after receiving the second, later ventricular sensed event signal has an earlier effective starting time coinciding with the determined sensed event time.

Alternatively, control circuit 80 may determine the sensed event time as the time of the first ventricular sensed event signal. In this case, control circuit 80 may restart the pacing escape interval set to an adjusted pacing escape interval set equal to the pacing escape interval less the time elapsed between the first, earliest ventricular sensed event signal and the second, later ventricular sensed event signal. In still other examples, control circuit 80 may determine the sensed event time to be the time of the second ventricular sensed event signal that occurs within the validation window. Control circuit 80 may then restart the pacing escape interval to have a starting time coinciding with the time of receiving the second, later ventricular sensed event signal without adjusting the pacing escape interval to have an earlier effective starting time. In still other examples, control circuit 80 may restart the pacing escape interval to have a starting time coinciding with the ending time of the validation window.

Because control circuit 80 validates the first, earliest ventricular sensed event signal upon receiving the second, later ventricular sensed event signal within the validation window, control circuit 80 may abort morphology analysis of the buffered ECG signal segment. In some examples, control circuit 80 may complete the process of buffering the ECG signal segment and start determining morphology features for comparing to the R-wave criteria during the validation window in order to reach a determination of a valid or invalid event signal by the end of the validation window (or shortly thereafter, e.g., within 5 to 20 ms of processing time) if a second ventricular sensed event signal is not received before expiration of the validation window. In this way, a decision to restart the pacing escape interval (or not) can be made at the end of the validation window or within a relatively short time interval, e.g., 10 ms or less, after the end of the validation window. Moreover, a decision to deliver a pending cardiac pacing pulse can be made upon expiration of the validation window when a ventricular sensed event signal is determined invalid.

Accordingly, control circuit 80 may be in the process of performing the morphology analysis when a second cardiac event signal is received within the validation window. In response to determining a valid event signal in response to a second ventricular sensed event signal at block 214, control circuit 80 may abort the morphology analysis process for the purposes of validating the first, earliest ventricular sensed event signal at block 218. The buffered ECG signal segment (or portion buffered so far) may be discarded. The process of determining morphology features and comparing to R-wave criteria may be aborted. The next X ms of the ECG signal may begin being buffered in memory in a FIFO manner at block 206. It is recognized that control circuit 80 may store and process ECG signal segments for other purposes, such as morphology analysis performed as part of a tachyarrhythmia detection algorithm. Aborting the morphology analysis at block 218 for the purpose of validating a ventricular sensed event signal for controlling cardiac pacing pulse timing may have no effect on other morphology analysis or ECG signal processing and analysis that may be performed by control circuit 80.

When a second ventricular sensed event signal is not sensed by the other sensing channel prior to expiration of the validation window ("no" branch of block 212), control circuit 80 completes determination of one or more morphology features at block 220. In one example, control circuit 80 determines a morphology matching score between the buffered ECG signal segment and the previously established R-wave template.

Additionally or alternatively, control circuit 80 determines the maximum peak amplitude of the buffered ECG signal segment. Additionally or alternatively, control circuit 80 determines a first order difference signal and determines the maximum and minimum of the first order difference signal for determining the slope difference as the difference between the maximum and the minimum of the first order difference signal.

Other examples of ECG signal features that may be determined at block 220 for validating a single ventricular sensed event signal that occurs within a validation window are listed herein. Such features may include one or more of: maximum signal width, maximum positive slope, maximum negative slope, number of zero crossings, or number of signal pulses in the rectified signal (e.g., between identified zero crossings or other designated threshold crossings), with no limitation intended. Threshold, ranges or other R-wave criteria values that are applied to the determined ECG signal features may be predetermined values stored in memory 82, established based on the R-wave template established at block 202, or may be programmable values stored in memory 82. While the ECG signal features are described herein as being determined from the signal received from the morphology signal channel 87, it is to be understood that one or more ECG signal features may be determined from a cardiac electrical signal received from first sensing channel 83, second sensing channel 85 and/or morphology signal channel 87. For example, a muscle noise pulse count may be determined as the number of signal pulses between identified zeros of a rectified ECG signal segment received by control circuit 80 from the sensing channel 83 or 85 that produced the first, earliest ventricular sensed event signal or from both sensing channels 83 and 85. An example method for determining a muscle noise pulse count is generally disclosed in U.S. Pat. No. 7,761,142 (Ghanem, et al.), incorporated herein by reference in its entirety.

At block 226, control circuit 80 may compare the determined morphology features to R-wave criteria. In some examples, the morphology matching score determined at block 220 is compared to an R-wave threshold matching score for validating the ventricular sensed event signal as corresponding to a true R-wave. The morphology matching score threshold may be set between 40 and 90 (out of a maximum matching score of 100) and may be set between 55 and 60 or 58 as examples. When the morphology matching score is greater than the threshold matching score at block 226, control circuit 80 may determine at block 230 that the single ventricular sensed event signal is a valid event signal with a high likelihood of being a true R-wave. Lower morphology matching scores may correspond to an oversensed P-wave, oversensed T-wave, myopotential noise (arising from skeletal muscle depolarizations) or EMI.

In other examples, R-wave criteria applied at block 226 may include comparing a noise metric to a noisy cycle threshold to verify that the signal sensed by the sensing channel 83 or 85 is not likely to be oversensed noise. Control circuit 80 may determine a noise metric as a characteristic or feature of the sensed cardiac electrical signal that is representative of the amplitude, width and/or number of signal pulses in the cardiac signal. The noise metric can be determined from a noise analysis time interval following and/or preceding a ventricular sensed event signal. The noise metric may be representative of the degree of noise contamination of the cardiac electrical signal and may be generally correlated to the likelihood of a noisy signal causing a false ventricular sensed event signal due to oversensing of a noise signal pulse.

As described below in conjunction with FIG. 7, one example of a noise metric that control circuit 80 may determine at block 220 is a signal pulse count. The signal pulse count may be determined during a post-sense blanking period applied to the cardiac electrical signal following a ventricular sensed event signal. When the signal pulse count, e.g., during an in-channel post-sense blanking period, is less than a noisy cycle threshold, the first, earliest ventricular sensed event signal may be identified as a valid event signal at block 230.

At block 227, for the purposes of controlling cardiac pacing pulse timing, control circuit 80 may optionally control the sensing circuit 86 to inhibit ventricular event sensing by the same sensing channel during an early sensing time period following the ventricular sensed event signal in response to determining that R-wave criteria are met at block 226. When R-wave criteria are met such that the ventricular sensed event signal corresponds to a true R-wave with a high degree of certainty, another true R-wave is not expected during normal sinus rhythm until at least a physiological myocardial refractory period has elapsed. The physiological refractory period for myocardium may be, for example, approximately 250 ms. The early sensing period during which sensing may be inhibited at block 227 can be set to extend up to 250 ms, 300 ms or 350 ms, as examples, after a ventricular sensed event signal. The early sensing period may be set to be less than a premature ventricular contraction (PVC) coupling interval known for a given patient to avoid inhibiting sensing of a true myocardial depolarization associated with a PVC (or other ectopic beat).

Control circuit 80 may inhibit early sensing for an early sensing time period after R-wave criteria are met by extending a post-sense blanking period or setting or extending a post-sense refractory period following the ventricular sensed event signal for the early sensing time period. The post-sense blanking period may typically be set to 140 to 200 ms or about 150 ms. For the purpose of sensing ventricular event signals for controlling cardiac pacing pulse timing, the post-sense blanking period may be extended to 200 to 300 ms. However, when the ventricular sensed event signals generated by the sensing channels 83 and 85 are also used by control circuit 80 for detecting ventricular tachyarrhythmia intervals that may be shorter than 200 ms or even shorter than 150 ms, extending the post-sense blanking period may not be performed. Instead, in some examples, the post-sense refractory period may be extended when R-wave criteria are met. During the post-sense refractory period, a sensing channel 83 or 85 may still sense ventricular event signals and pass a ventricular sensed event signal to control circuit 80 for use in detecting tachyarrhythmia intervals, but control circuit 80 may ignore refractory period sensed event signals for the purposes of restarting pacing escape intervals. For example, a post-sense refractory period may be set (or extended) to expire 200 to 400 ms, or 250 to 350 ms, following the ventricular sensed event signal. An R-wave sensing threshold crossing during the refractory period may be ignored by control circuit 80 for the purposes of restarting a pacing escape interval for controlling cardiac pacing pulse timing.

Additionally or alternatively, control circuit 80 may inhibit early sensing at block 227 by controlling sensing circuit 86 to increase the R-wave sensing threshold for an early sensing period after the ventricular sensed event signal. By increasing the R-wave sensing threshold to a maximum available setting or to an amplitude that is greater than the maximum peak amplitude of the cardiac electrical signal during the blanking period, for example, ventricular event sensing is inhibited during the early sensing period. By inhibiting sensing during an early sensing time period, e.g., up to 300 ms after a ventricular sensed event signal, oversensing of T-waves or noise that may occur early after the true R-wave may be avoided so that pacing inhibition due to oversensing may be avoided. It is to be understood, however, that block 227 is optional and may be omitted in some examples. For instance, when ventricular sensed event signals generated by sensing channels 83 and 85 are used by control circuit 80 for controlling bradycardia and asystole pacing delivery as well as determining ventricular sensed event intervals for tachyarrhythmia detection, block 227 may be omitted to enable sensing of R-waves or fibrillation waves that may be occurring at relatively short, tachyarrhythmia intervals. Alternatively, control circuit 80 may inhibit early sensing following R-wave criteria being met at block 226 only when the current ventricular rate, e.g., based on recent ventricular sensed event intervals, is less than a threshold rate, e.g., less than 90 beats per minute, that is well below a ventricular tachyarrhythmia or fibrillation rate.

In response to determining a valid event signal at block 230 based on R-wave criteria being met at block 226, control circuit 80 restarts the pacing escape interval at block 232. Control circuit 80 may determine the sensed event time as the time of the single ventricular sensed event signal determined as the valid event signal. Control circuit 80 may restart the pacing escape interval to have an effective starting time coinciding with the time of the received ventricular sensed event signal. For example, at the expiration of the validation window, control circuit 80 may restart the pacing escape interval set to an adjusted pacing escape interval equal to the pacing escape interval less the duration of the validation window. To illustrate, if the programmed lower pacing rate is 60 beats per minute, the corresponding pacing escape interval is 1 second. The pacing escape interval may be adjusted to 1 second less than validation window, e.g., 1 second less 105 ms or 895 ms, to have an effective starting time coinciding with the time of the single ventricular sensed event signal. In other examples, control circuit 80 may set the pacing escape interval to restart upon expiration of the validation window without adjusting the pacing escape interval to have an earlier effective starting time. Control circuit 80 returns to block 206 to begin buffering the ECG signal prior to the next ventricular sensed event signal, which may be received from either sensing channel 83 or 85.

When the R-wave criteria are not met at block 226, e.g., when the morphology matching score is not greater than the threshold matching score at block 226, control circuit 80 may apply additional R-wave criteria at block 228 that may identify ectopic depolarizations, such as premature ventricular contractions (PVCs) or aberrantly conducted ventricular depolarizations. The morphology of an ectopic depolarization may not match the valid R-wave morphology template with a matching score greater than the R-wave criteria threshold matching score. A PVC, aberrantly conducted ventricular depolarization, or other ectopic beat, however, can be a true ventricular myocardial depolarization that ought to be determined as a valid event signal for inhibiting a bradycardia pacing pulse. As such, control circuit 80 may be configured to determine a ventricular sensed event signal that is likely to be an ectopic beat as a valid event signal based on alternative morphology criteria at block 228, different than the R-wave criteria applied at block 226, to cause the timing circuit 90 to restart the pacing escape interval.

In this way, therapy delivery circuit 84 is controlled to withhold a pending cardiac pacing pulse that may be delivered into the vulnerable period that follows a PVC or other ectopic beat. The "vulnerable period" is a time period after a ventricular myocardial depolarization when a pacing pulse may capture the heart and induce a tachyarrhythmia in some patients. The vulnerable period generally occurs during the relative refractory period after a ventricular myocardial depolarization and may coincide with the latter portion of the T-wave. The T-wave is the cardiac electrical signal attendant to myocardial repolarization following depolarization. Absolute refractory generally occurs between the R-wave and the early portion of the T-wave when the state of refractoriness of the myocardium prevents a delivered pacing pulse from capturing the heart. During relative refractory, however, a pacing pulse of high enough energy could capture the myocardium and, in some instances, induce tachyarrhythmia.

Even when pacing during the vulnerable period is avoided, pacing at a relatively short time interval following a PVC or other ectopic beat that occurs at a relatively long coupling interval, resulting in a long-short ventricular interval sequence, may be proarrhythmic in some patients. As such, R-wave morphology criteria that is intended to identify ectopic beats may be applied at block 228 to properly validate the ventricular sensed event signal resulting from a ventricular depolarization due to an ectopic beat. The ectopic beat criteria defines one or more thresholds, ranges or other values of one or more ECG morphology features that correspond to a true R-wave. The ectopic beat criteria may be based on specific ECG signal features, such the maximum peak amplitude and the slope difference as an example. Other examples of specific R-wave features that may be determined for comparison to ectopic beat criteria for validating an associated ventricular sensed event signal are listed above.

In one example, control circuit 80 compares the maximum peak amplitude of the buffered ECG signal segment to the R-wave amplitude threshold established at block 204. The R-wave amplitude threshold may be set between 25% and 80% of the maximum peak amplitude of the previously established R-wave template as examples. In one example, the R-wave amplitude threshold is set to $7/16^{th}$ or between 40% and 50% of the R-wave template maximum peak amplitude.

Additionally or alternatively, control circuit 80 may compare the slope difference (e.g., determined between the maximum and minimum of the first order difference signal) to a threshold difference. In some examples, the slope difference is determined by determining a difference signal. Each sample point of a first order difference signal is determined as the difference between two consecutive sample points of the ECG signal segment. In other examples, a higher order difference signal may be determined, e.g., by determining the difference between every ith and the ith−n sample points to determine an nth order difference signal. Control circuit 80 may determine the difference signal using all of the sample points spanning the ECG signal segment or a predetermined portion of the ECG signal segment. For instance, the difference signal may be determined from the latest 30 sample points (or last 117 ms of the ECG signal segment sampled at a sampling rate of 256 Hz) or other predetermined subsegment of the ECG signal segment. A subsegment of the ECG signal segment used to determine the slope difference or other morphology feature (s) may begin later and/or end earlier than the ECG signal segment that includes the appended first and second portions as described above.

The threshold slope difference that is compared to the slope difference determined at block 220 may be 0.3 millivolts to 1.1 millivolt, as examples, and can be 0.7 millivolts (or a corresponding number of ADC units) in one example. The threshold slope difference may be programmable or based on a slope difference determined from the R-wave morphology template established at block 202. Relatively lower values of slope differences between the maximum and minimum peaks of the first order difference signal tend to occur when a P-wave, T-wave or myopotential interference is present in the ECG signal segment, such that the ventricular sensed event signal is an invalid event signal due to oversensing of a signal pulse that is not a true R-wave.

Control circuit 80 may determine that the single ventricular sensed event signal that triggers the start of the validation window is a valid event signal at block 230 when the maximum peak amplitude of the buffered ECG signal segment is greater than the R-wave threshold amplitude and the slope difference (the difference between the maximum and minimum peaks of the first order difference signal) is greater than the threshold slope difference. In some examples, control circuit 80 may additionally verify that noisy cycle criteria are not met at block 228 as described above in conjunction with block 226. Control circuit 80 restarts the pacing escape interval at block 232 in response to determining a valid event signal at block 230 based on the ectopic beat criteria being met at block 228. While not shown explicitly in the flow chart 200, in some examples, control circuit 80 may inhibit early sensing at block 227 as described above following the determination of an ectopic beat at block 228. As such in some examples, control circuit 80 may advance to block 227 after determining that the R-wave criteria are met at block 226 or after determining that the ectopic beat criteria are met at block 228.

As described above, the pacing escape interval may be set to have an effective starting time coinciding to the time of the single ventricular sensed event signal. In other examples, the pacing escape interval may be restarted at the expiration of the validation window, without adjusting the pacing escape interval to have an earlier effective starting time corresponding to the time of the single ventricular sensed event signal. Thus, the ectopic beat criteria applied at block 228 may include one or more R-wave criteria thresholds, ranges or other values that are applied to ECG signal segment features and indicate a true ventricular myocardial depolarization. Because the ventricular myocardial depolarization may be a non-sinus R-wave, the overall ECG signal segment morphology may not match the R-wave template with a matching score that meets the R-wave matching score threshold at block 226. Additional R-wave morphology criteria, defining ectopic beat criteria, may be applied to validate a ventricular sensed event signal associated with ectopic beats.

When the ectopic beat criteria are not met at block 228, e.g., when the maximum peak amplitude of the buffered ECG signal segment is less than or equal to the R-wave threshold amplitude and/or the slope difference is less than or equal to the R-wave slope difference threshold and/or noisy cycle criteria are met by a noise metric, control circuit 80 may determine that the single ventricular sensed event signal is an invalid event signal at block 234. The pacing escape interval is not restarted, and, if the pacing escape interval expires, therapy delivery circuit 84 may deliver a pending cardiac pacing pulse scheduled to occur at the expiration of the pacing escape interval. Control circuit 80 may return to block 206 from block 234 to begin buffering the next ECG signal segment while waiting for the next ventricular sensed event signal, from either one of the sensing channels 83 or 85, that occurs outside a blanking period or a previously started validation window.

In some examples, control circuit 80 may optionally set a pace delay interval at block 236 in response to the invalid event signal determination at block 234 (as shown in FIG. 6). When control circuit 80 determines that a pacing escape interval expires prior to the expiration of the pace delay interval, control circuit 80 may control the therapy delivery circuit 84 to delay the pending cardiac pacing pulse that is scheduled at the expiration of the pacing escape interval until after the expiration of the pace delay interval.

In some instances, a ventricular sensed event signal may be falsely determined to be an invalid event signal when it is actually valid and corresponds to a true R-wave or ventricular depolarization. If a pacing escape interval expires soon after a false invalid sensed event signal, a ventricular pacing pulse could be delivered during the vulnerable period following the true ventricular depolarization. In order to avoid pacing into the vulnerable period following a false invalid event signal, control circuit 80 may set a pace delay interval at block 236 in response to the invalid event signal determination at block 234.

The pace delay interval may be set to 400 to 800 ms, as examples, to avoid pacing until after a vulnerable period when the invalid event signal actually corresponds to a true R-wave. If the pacing escape interval expires before the pace delay interval, control circuit 80 may control therapy delivery circuit 84 to withhold the scheduled pacing pulse until the pace delay interval expires. A pending pacing pulse scheduled to be delivered at the expiration of a pacing escape interval that occurs during the validation window or before the pace delay interval expires may be delivered upon expiration of the pace delay interval. A pending pacing pulse that is scheduled at the expiration of a pacing escape interval that is running at the time of the invalid event signal determination at block 234 and ultimately expires after the pace delay interval (and before a next valid sensed event signal) may be delivered by therapy delivery circuit 86 upon expiration of the pacing escape interval.

If a valid event signal is identified during the pace delay interval, the pacing escape interval may be restarted in response to the valid event signal and the pending, delayed cardiac pacing pulse may be cancelled. However, if another invalid event signal is identified during the pace delay interval, the pending pacing pulse may still be delivered upon expiration of the pace delay interval. Control circuit 80 may be configured to allow a previously started pace delay interval to continue running without restarting the pace delay interval in response to a second invalid event signal consecutively following a previous invalid event signal. Setting a pace delay interval in response to an invalid event signal at block 236 is optional and may be omitted in some examples.

Figure 7:
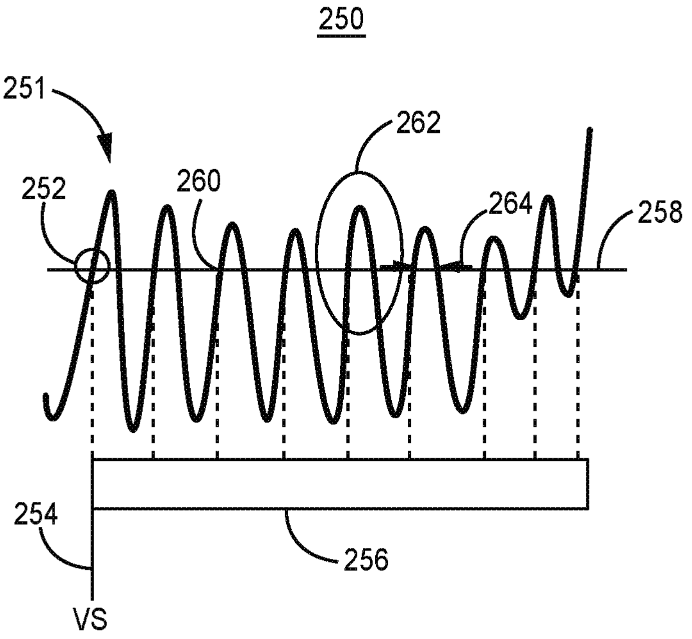
FIG. 7 is a diagram of a cardiac electrical signal during a post-sense blanking period illustrating a method for determining a noise metric for use in validating a ventricular sensed event signal by the ICD according to some examples.

FIG. 7 is a diagram 250 of a cardiac electrical signal 251 during a post-sense blanking period 256 illustrating a method for determining a noise metric by control circuit 80 according to some examples. Control circuit 80 may determine morphology features of the cardiac electrical signal following the first, earliest ventricular sensed event signal (and/or a second, later ventricular sensed event signal) that are indicative of noise contamination of the cardiac electrical signal. When the cardiac electrical signal meets noisy cycle criteria, a ventricular sensed event signal that started a validation window may be determined to be invalid by control circuit 80.

In FIG. 7, a ventricular sensed event signal 254 is generated by one of sensing channels 83 or 85 of sensing circuit 86 in response to an R-wave sensing threshold crossing 252 by the cardiac electrical signal 251. In this example, cardiac electrical signal 251 may be contaminated by noise pulses, e.g., skeletal muscle myopotential noise. At the time of the R-wave sensing threshold crossing 252, the R-wave sensing threshold 258 may be set at a starting threshold amplitude set to a first percentage of a maximum peak amplitude of a preceding sensed event signal, at an intermediate sensing threshold amplitude set to a second, lower percentage of the maximum peak amplitude of the preceding sensed event signal, or to a minimum sensing threshold amplitude corresponding to the programmed sensitivity for sensing R-waves. Methods for adjusting the R-wave sensing threshold during a ventricular cycle are described below in conjunction with FIG. 9. The ventricular sensed event signal 254 may be the first, earliest ventricular sensed event signal received outside of a validation window that causes control circuit 80 to start a new validation window. It is to be understood, however, that in some examples control circuit 80 may additionally or alternatively determine a noise metric from the cardiac electrical signal sensed by the sensing circuit 83 or 85 that produces a second, later ventricular sensed event signal during a validation window for verifying that the second ventricular sensed event signal is unlikely to be oversensed noise. As such, in some examples the methods described in conjunction with FIG. 7 may be performed on one cardiac electrical signal sensed by either sensing circuit 83 or 85 when a single ventricular sensed event signal is received without a second ventricular sensed event signal within the validation window. Additionally or alternatively, the methods described in conjunction with FIG. 7 may be performed on both cardiac electrical signals sensed by both of sensing circuits 83 and 85 when a second ventricular sensed event signal is received within the validation window.

In response to the ventricular sensed event signal 254, sensing circuit 86 starts a post-sense blanking period 256. The cardiac electrical signal 251, which may be a narrowband, notch filtered and rectified signal, received during the blanking period 256 may be analyzed by control circuit 80 for determining a noise metric. In other examples, sensing circuit 86 may be configured to determine the noise metric and pass a noise metric signal to control circuit 80. In one example, control circuit 80 (or sensing circuit 86) counts each positive going crossing 260 of sensing threshold 258 during the blanking period 256. Each positive going threshold crossing 260 is shown by dashed line in FIG. 7. Each positive going threshold crossing 260 marks a signal pulse having an amplitude that is greater than the R-wave sensing threshold 258 that occurs during the blanking period 256. For example, one signal pulse 262 is counted in response to one positive going R-wave sensing threshold crossing. In other examples, control circuit 80 may count one signal pulse in response to a positive going R-wave sensing threshold crossing followed by a negative going sensing threshold crossing or in response to a negative going R-wave sensing threshold crossing.

Control circuit 80 may determine the noise metric by determining the count of signal pulses, which may be a count of positive going (or negative going or pairs of positive followed by negative going) sensing threshold crossings that occur during the blanking period 256. In the example shown the noise metric is determined as a signal pulse count of 8, where each signal pulse has an amplitude equal to or greater than the R-wave sensing threshold 258. The R-wave sensing threshold crossing 252 that starts the blanking period 256 may be excluded from the signal pulse count in some examples. In other examples, the R-wave sensing threshold crossing 252 may be included.

In other examples, a different amplitude threshold than the R-wave sensing threshold amplitude 258 which resulted in a ventricular sensed event signal 254 may be used in identifying and counting signal pulses during the blanking period 256. In some examples, a signal pulse amplitude threshold may be less than or greater than the R-wave sensing threshold amplitude. In some examples, the signal pulse amplitude threshold may be set based on the R-wave sensing threshold 258, the programmed sensitivity, the maximum peak amplitude of the cardiac electrical signal 251 during the blanking period 256 (or during an R-wave peak tracking period) or the first peak amplitude following R-wave sensing threshold crossing 252.

Furthermore, it is to be understood that the time interval over which the noise metric is determined may be longer than or shorter than the blanking period 256 that is applied by the respective sensing channel 83 or 85 for sensing R-waves. The time interval over which the noise metric is determined may be set to include an expected QRS width. When a true R-wave is sensed, the number of positive R-wave sensing threshold crossings during the blanking period after the first positive going threshold crossing 252 is expected to be few or none. The time interval for determining the noise metric may be set to promote inclusion of a baseline portion of the cardiac electrical signal for determining the noise metric from a portion(s) of the cardiac electrical signal 251 when, for example, T-waves and/or P-waves are not expected to occur. In other examples, the time interval over which the noise metric is determined may extend from the start of the blanking period to the expiration of a predetermined time interval, which may be the first drop time interval described below in conjunction with FIG. 9 or a portion thereof or from the start of the blanking period to the expiration of the second drop time interval described below in conjunction with FIG. 9 or a portion thereof. As described below, the first and second drop time intervals refer to time intervals that are used in adjusting the R-wave sensing threshold. The time interval over which the cardiac electrical signal 251 is analyzed for determining the noise metric may be programmable by a user in some examples and may be adjustable by control circuit 80 based on the rate of ventricular sensed event signals, e.g., shortened when sensed event intervals are shorter and lengthened when sensed event intervals are longer.

In addition or alternatively to determining the signal pulse count, control circuit 80 may determine one or more other noise metrics during a noise analysis time interval. For example, control circuit 80 may determine the pulse width 264 of each signal pulse during the blanking period 256 (or other selected noise analysis time interval). The pulse width 264 may be determined as the time from a positive going threshold crossing to a negative going threshold crossing. The pulse width may alternatively be determined as the time between two maximum peaks, two minimum peaks (or zeros) or other time interval representative of the width of a signal pulse. The pulse widths determined over the blanking period 256 (or other selected time interval) may be summed for determining a noise metric in some examples. The pulse widths of signal pulses having at least a threshold amplitude, e.g., the R-wave sensing threshold or another selected signal pulse threshold amplitude, may be included in the summation with smaller amplitude signal pulses (having a peak that does not exceed the threshold amplitude) excluded or ignored. Additionally or alternatively, a count of signal pulses having a pulse width less than a threshold width may be determined as a noise metric by control circuit 80 in some examples. Additionally or alternatively, the maximum signal pulse width may be determined by control circuit 80 as a noise metric. The number of signal pulses, the cumulative signal width, and the number of "narrow" signal pulses having less than a threshold pulse width may each be positively correlated to the number of noise pulses in the cardiac electrical signal 251, which may lead to an invalid event signal determination when the noise metric is greater than a noisy cycle threshold. The maximum pulse width may be inversely correlated to noise contamination since a relatively wide signal pulse may be evidence of a true R-wave or fibrillation wave in the cardiac electrical signal. When the maximum pulse width is greater than a width threshold, the ventricular sensed event signal may be determined to be a valid event signal.

Figure 8:
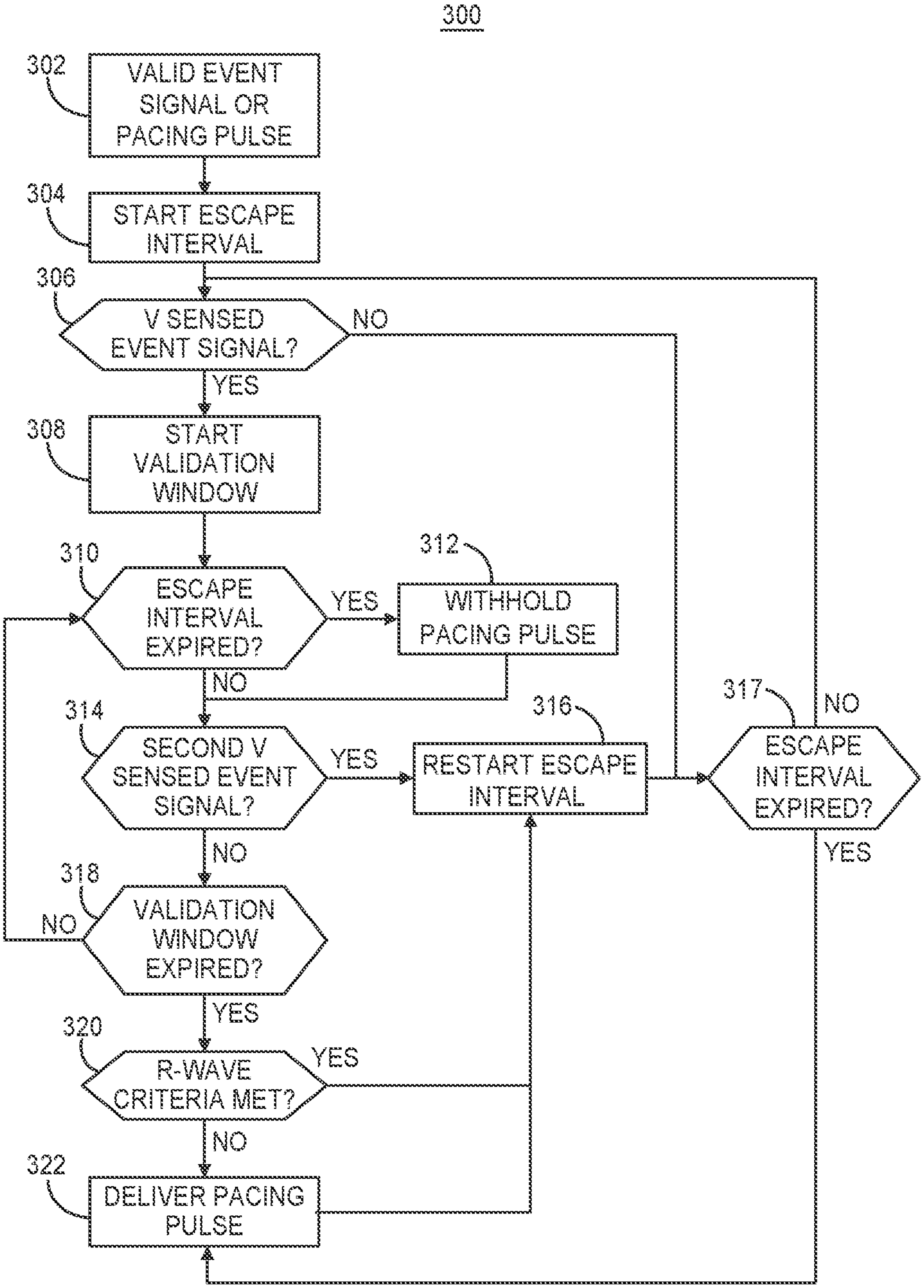
FIG. 8 is a flow chart of a method that may be performed by the ICD of FIG. 3 for controlling the timing of pacing pulses delivered by the ICD according to one example.

FIG. 8 is a flow chart 300 of a method for controlling the timing of pacing pulses delivered by ICD 14 according to one example. At block 302, control circuit 80 identifies a valid event signal that, as described above in conjunction with FIG. 6, causes control circuit 80 to restart a pacing escape interval at block 304. In some instances, the pacing escape interval is restarted in response to a delivered pacing pulse (as indicated in block 302). The pacing escape interval is started at block 304 to schedule a pending cardiac pacing pulse upon expiration of the pacing escape interval so that the pacing pulse is delivered at a desired pacing rate interval if a valid ventricular event signal is not received prior to expiration of the pacing escape interval. As described below the pacing rate interval that the pacing escape interval is set to may be a hysteresis interval or a lower rate interval corresponding to a programmed lower pacing rate.

During the pacing escape interval, control circuit 80 may receive a ventricular sensed event signal at block 306. As described above in conjunction with FIG. 6, control circuit 80 may freeze storage of ECG signal sample points being stored in a FIFO buffer in memory 82 and continue storing a second portion of an ECG signal segment in response to the ventricular sensed event signal. The ECG signal segment can be used by control circuit 80 for validating the sensed event signal if a second ventricular sensed event signal is not sensed within the validation window.

Control circuit 80 starts the validation window at block 308 in response to the ventricular sensed event signal received at block 306. In some instances, the pacing escape interval may expire as determined by control circuit 80 at block 310 during the validation window, after the first, earliest ventricular event signal but before a second ventricular sensed event signal is received to validate the first ventricular event signal. When control circuit 80 determines that the pacing escape interval expires before a second ventricular sensed event signal is received from sensing circuit 86, control circuit 80 controls the therapy delivery circuit 84 to withhold the pending cardiac pacing pulse scheduled to be generated and delivered at the expiration of the pacing escape interval. If the validation window has not expired but the pacing escape interval has expired after the first ventricular sensed event signal, control circuit 80 may withhold or delay the pending cardiac pacing pulse until a determination is made regarding the validity of the first ventricular sensed event signal. Delivery of the pending cardiac pacing pulse may or may not be appropriate at the time of the expired pacing escape interval since the validity of the first ventricular sensed event signal is unknown at the time of the pacing escape interval expiration. If the first, earliest ventricular sensed event signal is subsequently determined to be valid, the pacing escape interval can be restarted without delivering the pending cardiac pacing pulse. The pending pacing pulse may be cancelled. However, if the first, earliest ventricular sensed event signal is subsequently determined to be invalid, the pending cardiac pacing pulse scheduled at the expiration of the pacing escape interval can be delivered by therapy delivery circuit 84.

As such, at block 312 control circuit 80 may control the therapy delivery circuit 84 to withhold a pending cardiac pacing pulse scheduled at the expiration of a pacing escape interval that occurs during the validation window until a determination can be made regarding the validity of the first ventricular sensed event signal. Control circuit 80 waits for a second ventricular sensed event signal at block 314 while the validation window is running and may concurrently store and analyze the ECG signal segment for validating the first ventricular sensed event signal.

If control circuit 80 receives a second ventricular sensed event signal at block 314 before the validation window expires, control circuit 80 restarts the pacing escape interval at block 316. The first ventricular sensed event signal (collectively with the second ventricular sensed event signal) is determined to be a valid event signal. As described above in conjunction with FIG. 6, control circuit 80 may restart the pacing escape interval to have an effective starting time that coincides with the time of the first ventricular sensed event signal, the time second ventricular sensed event signal, or at a midpoint between the time of the first and the time of the second ventricular sensed event signals, in various examples. In other examples, the pacing escape interval may be restarted at the expiration of the validation window. The withheld pending cardiac pacing pulse is cancelled by control circuit 80. While the restarted pacing escape interval is running (at block 317), control circuit 80 monitors for the next first ventricular sensed event signal from either of sensing channels 83 or 85 outside of the post-sense blanking period for the respective sensing channel. If the pacing escape interval restarted at block 316 is determined to expire at block 317, before another ventricular sensed event signal is received from sensing circuit 86, therapy delivery circuit 84 generates and delivers the scheduled cardiac pacing pulse at block 322 in response to the pacing escape interval expiration.

Referring again to block 314, if control circuit 80 does not receive a second ventricular event signal from the other sensing channel before the validation window expires (as determined at block 318), control circuit 80 determines if R-wave criteria are met at block 320 for validating the single ventricular sensed event signal. As described above in conjunction with FIGS. 5 and 6, control circuit 80 may determine one or more features of the buffered ECG signal segment for determining if R-wave criteria are met, e.g., a morphology matching score being greater than a threshold matching score and/or other R-wave criteria, which may include criteria for identifying non-sinus R-waves such as an R-wave amplitude threshold and/or a slope difference threshold (e.g., according to ectopic beat criteria).

When control circuit 80 determines that the morphology criteria are met for validating the single ventricular sensed event signal, control circuit 80 determines that the single ventricular sensed event signal is valid and restarts the pacing escape interval at block 316. The pending pacing pulse scheduled to be delivered at the escape interval that expired during the validation window is cancelled in response to validating the single ventricular sensed event signal. Even though the pacing escape interval expired, a pending pacing pulse is not delivered during the validation window and is cancelled when the single ventricular sensed event signal is subsequently validated. The pacing escape interval may be restarted at block 316 as an adjusted pacing escape interval to have an effective starting time coinciding with the single ventricular sensed event signal. The pacing escape interval may be started upon expiration of the validation window but set to an adjusted (shortened interval) such that the pacing escape interval has an earlier effective starting time coinciding with the single ventricular sensed event signal. In other examples, the pacing escape interval can be restarted at the expiration of the validation window by control circuit 80 without any adjustments that would result in an earlier effective starting time. As described above, control circuit 80 monitors for another ventricular sensed event signal at block 306 from sensing circuit 86 while the restarted pacing escape interval is running at block 317. If no ventricular sensed event signal is received prior to expiration of the restarted pacing escape interval at block 317, therapy delivery circuit 84 generates and delivers a pacing pulse at block 322.

Referring again to block 320, if control circuit 80 determines that the R-wave morphology criteria for validating the single ventricular sensed event signal are not met and a pacing escape interval has expired during the validation window, the pending cardiac pacing pulse is delivered by therapy delivery circuit 86 at block 322 after the expiration of the validation window. In various examples, control circuit 80 is configured to complete the morphology analysis within the validation window while waiting for a possible second ventricular sensed event signal so that the latency of a pending pacing pulse is not substantially longer than the validation window. In this way, a pending pacing pulse that is withheld during the validation window may be delivered upon expiration of the validation window, or within a relatively short time interval after the validation window as required for therapy delivery circuit 84 to generate and deliver the pending pacing pulse, e.g., within 5 ms after the validation window, within 10 ms after the validation window, within 20 ms after the validation window or within 30 ms after the validation window. By performing the morphology analysis during the validation window, an unacceptable latency in delivering a pending pacing pulse is avoided if the single ventricular sensed event signal is determined to be invalid. For instance, control circuit 80 may be configured to complete the morphology signal analysis for determining if R-wave criteria are met by the expiration of validation window or earlier after the single ventricular sensed event signal. When the second portion of the ECG signal segment is 90 ms and the validation window is set to 105 ms, as an example, control circuit 80 may complete the morphology analysis for determining that R-wave criteria are met (or not) within the final 15 ms of the validation window. When a second ventricular pacing pulse is not received and the R-wave criteria are not met, therapy delivery circuit 80 may deliver the pending pacing pulse at block 322 upon expiration of the validation window without a processing delay. In response to delivery of the pacing pulse at block 322, control circuit 80 restarts the pacing escape interval at block 316 and, while the escape interval is running (block 317), monitors for the next ventricular sensed event signal (block 306).

Figure 9:
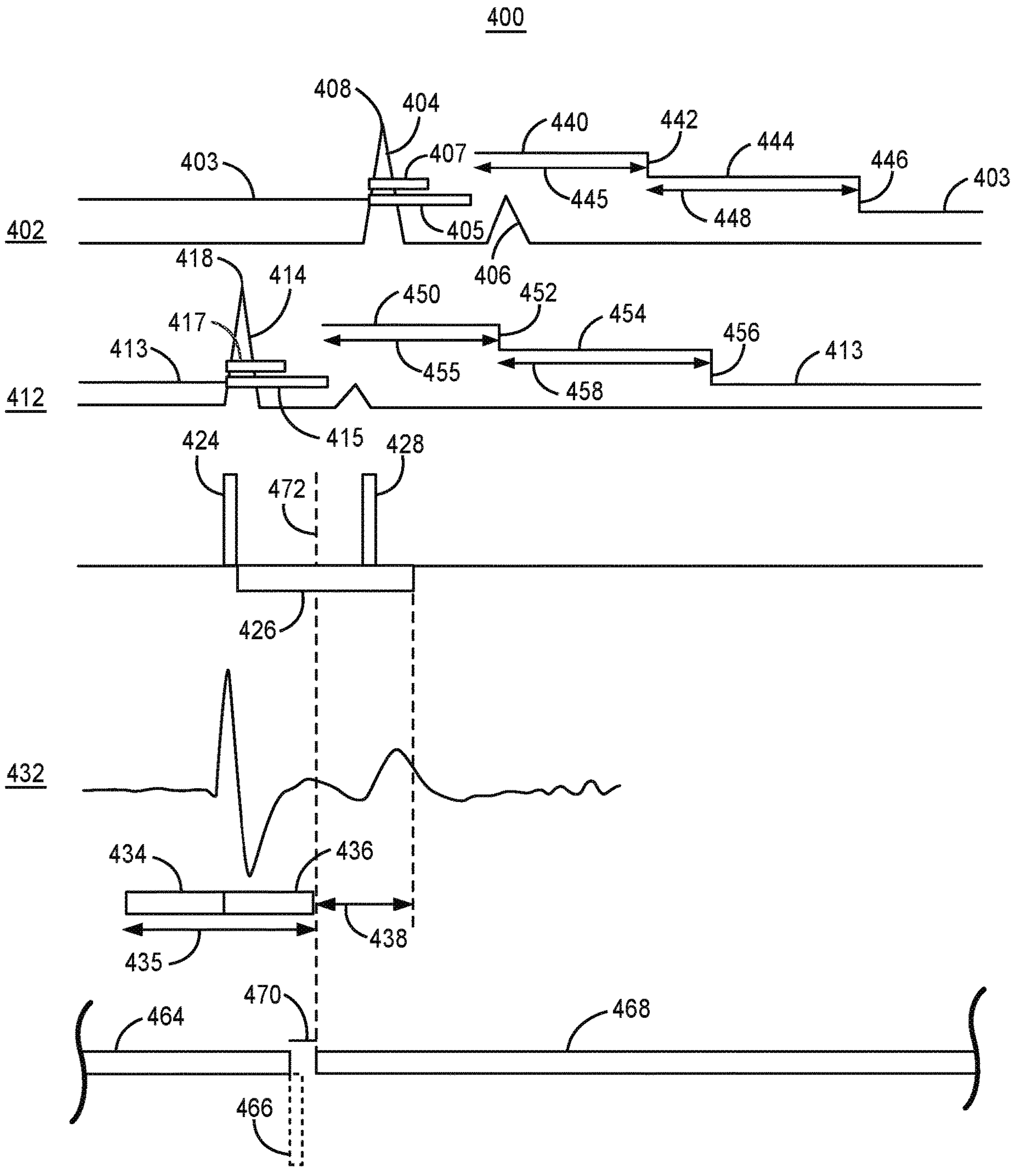
FIG. 9 is a timing diagram depicting time intervals and events associated with a process of validating a ventricular sensed event signal and controlling pacing pulse delivery according to some examples.

FIG. 9 is a timing diagram 400 depicting time intervals and events associated with a process of validating a ventricular sensed event signal and controlling pacing pulse delivery according to some examples. With reference to FIG. 4 and FIG. 9, a first cardiac electrical signal 402 that may be received by R-wave detector **66*a* of the first sensing channel 83 and a second cardiac electrical signal 412 that may be received by R-wave detector 66*b* of the second sensing channel 85 are illustrated. The second sensing channel 85 generates the first, earliest ventricular sensed event signal 424 in response to cardiac electrical signal 412 (R-wave 414) crossing the R-wave sensing threshold 413. The second sensing channel 85 starts a post-sense blanking period 415 in response to the R-wave sensing threshold crossing by cardiac electrical signal 412. During blanking period 415 no additional ventricular sensed event signals are generated by sensing channel 85. R-wave detector 66*b* may determine the maximum peak amplitude 418 during the post-sense blanking period 415. R-wave detector 66*b* may determine the maximum peak amplitude 418 during an R-wave peak tracking period 417 that can be a portion of the post-sense blanking period 415. For instance, the R-wave peak tracking period 417 may be 100 to 140 ms, or between 128 to 130 ms as an example, and the post-sense blanking period 415 may be set to 140 ms or up to 200 ms. The maximum peak amplitude 418 is used to set the auto-adjusting R-wave sensing threshold to a starting threshold amplitude 450 that is a percentage, e.g., between 40 to 75 percent or 53% in one example, of the maximum peak amplitude 418. In the example shown, as long as an R-wave sensing threshold crossing is not detected, R-wave detector 66*b*, under the control of control circuit 80, may adjust the R-wave sensing threshold by a step decrement 452 from the starting threshold amplitude 450 to a second lower threshold amplitude 454 at the expiration of a drop time interval 455. After a second drop time interval 458, R-wave detector 66*b* may decrease the R-wave sensing threshold in a step decrement 456 to the minimum amplitude 413, equal to the programmed sensitivity and also referred to herein as the sensing floor. In other examples, the R-wave sensing threshold may be adjusted according to one or more decay rates over a respective decay interval and/or according to one or more step decrements after a respective drop time interval. The post-sense blanking period 415 and R-wave sensing threshold described in conjunction with FIG. 9** may be different than the post-pace blanking period and post-pace R-wave sensing threshold. For example, the post-pace blanking period may be longer and/or the drop time intervals and/or percentages used to set the starting and second lower threshold amplitudes may be different following a ventricular pacing pulse than following a ventricular sensed event signal.

An ECG signal 432 that may be received by control circuit 80 from morphology signal channel 87 is illustrated. As described above, the ECG signal 432 may be stored over a predetermined storage time interval 434 in a rolling manner in a FIFO buffer in memory 82. In response to receiving the first, earliest ventricular sensed event signal 424 outside of a validation window since a preceding ventricular event (e.g., a preceding valid event signal or delivered pacing pulse, not shown in FIG. 9), control circuit 80 starts a validation window 426. Control circuit 80 may freeze the currently stored ECG signal corresponding to the most recent storage time interval 434 as the first portion of an ECG signal segment. Control circuit 80 may continue to store the ECG signal 432 over the next storage interval 436 to obtain the second portion of the ECG signal segment. In this way, an ECG signal segment of ECG signal 432 is stored over a total morphology analysis time interval 435 that encompasses the time of the first, earliest ventricular sensed event signal 424. At least a portion of the ECG signal segment is received during at least a portion of the validation window 426 and a portion of the ECG signal segment may be received before the validation window 426. In other examples, control circuit 80 may continuously buffer the ECG signal 432 in a FIFO buffer in memory 82. When the next storage interval 436 has elapsed after a ventricular sensed event signal 424, such that sample points spanning the total morphology analysis time interval 435 are buffered in memory 82, the ECG signal segment extending over total morphology analysis time interval 435, including sample points during at least a portion of the validation window 426, may be moved to a temporary buffer in memory 82. Control circuit 80 may analyze the stored ECG signal segment to determine morphology features as described in the examples given above.

Control circuit 80 may be configured to start processing the ECG signal segment acquired over morphology analysis time interval 435 on or before the expiration of the storage interval 436 such that the morphology signal processing time 438 for determining morphology features and applying R-wave criteria for validating the first, earliest ventricular sensed event signal 424 is completed by the expiration of the validation window 426 or within a short time after, e.g., within 20 ms or less after the expiration of the validation window 426. In one example, the first storage time interval 434 is 98 ms and the next storage interval 436 is 90 ms so that the total morphology analysis time interval 435 is 188 ms in duration. If the validation window is 105 ms, as an example, the processing time interval 438 is 15 ms during which the morphology analysis of the ECG signal segment is completed by control circuit 80. It should be noted that the various time intervals illustrated in FIG. 9 are not necessarily drawn to scale for the sake of clarity since some time intervals, such as the processing time interval 438 may be very short compared to validation window 426 and the total morphology analysis time interval 435 over which the ECG signal segment is acquired.

In the example shown, the first sensing channel 83 generates a second, later ventricular sensed event signal 428 in response to cardiac electrical signal 402, in this case R-wave 404 of cardiac electrical signal 402, crossing the R-wave sensing threshold 403 applied by R-wave detector **66*a*. First sensing channel 83 starts a post-sense blanking period 405 in response to detecting an R-wave sensing threshold crossing. R-wave detector 66*a* may apply an auto-adjusting R-wave sensing threshold amplitude as generally described above, which may include a starting threshold amplitude 440 set to a percentage of the maximum peak amplitude 408 determined during an R-wave peak tracking period 407, which may be a portion of the post-sense blanking period 405. The starting threshold amplitude 440 may be decreased by a step decrement 442 at the expiration of drop time interval 445 to a second lower threshold amplitude 444. It is noted that the first drop time interval 445 (and 455) may be set to extend past an expected time of T-wave 406 following R-wave 404 to reduce the likelihood of T-wave oversensing. The R-wave sensing threshold is adjusted to the minimum amplitude 403, which may be equal to the programmed sensitivity, by a step decrement 446 at the expiration of a second drop time interval 448. The second lower threshold amplitude 444 and the second drop time interval 448 may be set to avoid decreasing the R-wave sensing threshold to the minimum amplitude 403 before a P-wave is expected to avoid P-wave oversensing. The programmed sensitivities used to set the minimum amplitudes 403 and 413, first percentages of peak amplitudes 408 and 418 used for setting starting threshold amplitudes 440 and 450 respectively, second percentages of peak amplitudes 408 and 418 used for setting the second lower threshold amplitudes 444 and 454 respectively, and drop time intervals 445, 448, 455 and 458 may be controlled separately by the individual sensing channels 83 and 85 according to unique sensing threshold control parameter values for each sensing channel 83 and 85 under the control of control circuit 80**.

Since ventricular sensed event signal 428 is received by control circuit 80 after morphology analysis time interval 435, control circuit 80 may begin processing and analysis of the ECG signal segment during the validation window 426. If the later sensed event signal 428 is received during morphology analysis time interval 435 (e.g., during the second storage interval 436), control circuit 80 may abort the morphology analysis of the ECG signal segment for the purpose of validating the earlier ventricular sensed event signal 424. However, the ECG signal segment stored over morphology analysis time interval 435 may be analyzed for other purposes, such as tachyarrhythmia detection. When the second, later ventricular sensed event signal 428 is received after morphology analysis time interval 435 but within validation window 426, control circuit 80 determines that the first, earlier ventricular sensed event signal 424 (and second ventricular sensed event signal 428 collectively) is a valid event signal corresponding to a true R-wave 414 (and 404). Morphology analysis of the ECG signal segment for validating the first, earlier ventricular sensed event signal 424 may begin prior to receiving the second, later ventricular sensed event signal 428, but the morphology analysis may be aborted by control circuit 80. The ECG signal segment may be discarded and the temporary FIFO memory buffer may begin storing the ECG signal again on a rolling basis.

In some instances, a previously started pacing escape interval 464 may expire during the validation window 426. Control circuit 80 may control therapy delivery circuit 84 to withhold a pending cardiac pacing pulse 466 (shown by dashed line) scheduled for delivery at the expiration of pacing escape interval 464 when a first, earliest ventricular sensed event signal has been received but not validated and the validation window 426 is not expired. If the first, earlier ventricular sensed event signal 424 is determined to be a valid event signal, based on a second, later ventricular sensed event signal 428 received prior to the expiration of the validation window 426, control circuit 80 cancels the pending pacing pulse 466 and restarts the pacing escape interval 468. While timing circuit 90 of control circuit 80 may not restart the pacing escape interval 468 until the validation window 426 expires, the pacing escape interval 468 may be adjusted to have an effective starting time at a midpoint 472 between the first and second ventricular sensed event signals 424 and 428 as shown in FIG. 9.

In other examples, the pacing escape interval 468 may be restarted to have an effective starting time coinciding with the time of the first ventricular sensed event signal 424 or the second ventricular sensed event signal 428 or the expiration of the validation window 426. Because a pending pacing pulse is not delivered upon expiration of the pacing escape interval 464 and the next pacing escape interval 468 is not necessarily restarted upon the expiration of the preceding pacing escape interval 464, the actual pacing rate when pacing pulses are delivered may have some jitter resulting from variation in the time delay 470 between one pacing escape interval expiration and the start of the next pacing escape interval 468. In some examples, the time delay 470 between expiration of the one pacing escape interval 464 and the time a next pacing escape interval 468 is restarted may be up to the duration of the validation window 426. In the example shown, the pacing escape interval 468 is started a short time delay 470 after the expiration of the preceding pacing escape interval 464 that is within the variability of the timing of ventricular sensed event signals 424 and 428 received from the two sensing channels 83 and 85.

Figure 10:
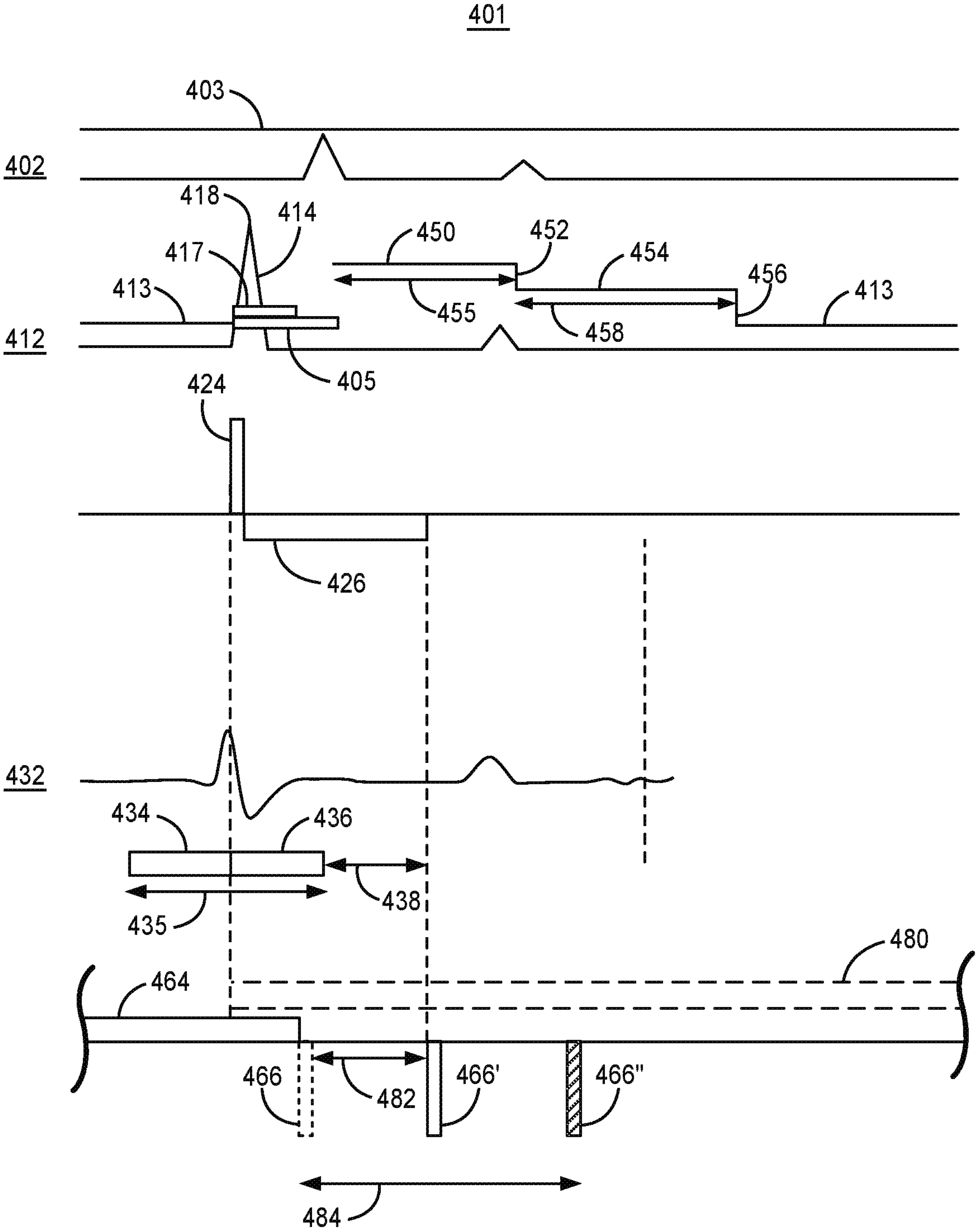
FIG. 10 is a timing diagram depicting time intervals and events associated with a process of validating a ventricular sensed event signal and controlling pacing pulse delivery according to another example.

FIG. 10 is a timing diagram 401 depicting time intervals and events associated with a process of validating a ventricular sensed event signal and controlling pacing pulse delivery according to another example. Identically numbered elements in FIG. 10 correspond to like-numbered elements shown in FIG. 9. In the example of FIG. 10, however, a second ventricular sensed event signal is not received by control circuit 80 from sensing circuit 86 prior to the expiration of the validation window 426 to validate the first ventricular sensed event signal 424. The R-wave may be undersensed by the first sensing channel (as represented by the low amplitude signal 402 in FIG. 10) or the single ventricular sensed event signal 424 may be oversensing of a P-wave, T-wave, skeletal muscle myopotentials or noise in some instances.

When the first ventricular sensed event signal 424 is received (outside a validation window since a preceding ventricular sensed event signal), control circuit 80 freezes the buffered portion of the ECG signal segment in memory 82 stored over the first storage time interval 434 and stores the ECG signal segment over the next storage interval 436 to obtain the ECG signal segment over the total morphology analysis time interval 435 encompassing the ventricular sensed event signal 424. When a second ventricular sensed event signal is not received by the expiration of the next storage interval 436, control circuit 80 begins processing of the ECG signal segment to determine morphology features for validating the ventricular sensed event signal 424. Control circuit 80 may be configured to determine whether the R-wave morphology criteria are met by the expiration of the validation window 426, so that the ventricular sensed event signal 424 can be identified as valid or invalid when validation window 426 expires.

If a previously started pacing escape interval 464 expires during the validation window 426, control circuit 80 controls therapy delivery circuit 84 to withhold the pending cardiac pacing pulse 466. If the R-wave criteria are subsequently met by the ECG signal segment, control circuit 80 determines that the first, earliest ventricular sensed event signal 424 is a valid event signal and restarts a pacing escape interval 480. The pacing escape interval 480 may be started upon expiration of the validation window 426 to have an earlier effective starting time corresponding to the time of the single ventricular sensed event signal 424, e.g., by starting an adjusted pacing escape interval set to the pacing escape interval less the duration of the validation window 426. Alternatively, the pacing escape interval 480 may be adjusted to start at a time coinciding with the expiration of the preceding pacing escape interval 464 when pacing escape interval 464 expires during the validation window 426. In still other examples, control circuit 80 may restart the next pacing escape interval 480 at the expiration of the validation window 426 without adjusting pacing escape interval 480 to have an earlier effective starting time. If the preceding escape interval 464 has expired during the validation window 426, control circuit 80 cancels the pending cardiac pacing pulse 466 in response to determining the first, earliest ventricular sensed event signal to be valid based on R-wave criteria being met by the ECG signal segment. In the example shown in FIG. 10, ventricular sensed event signal 424 is generated in response to sensing a true R-wave 414 such that determination of a valid event signal based on morphology analysis and restarting of the pacing escape interval 480 is appropriate.

For the sake of illustration, the diagram of FIG. 10 also depicts the control of pacing pulse delivery when the ventricular sensed event signal 424 is determined to be invalid, e.g., due to oversensing of a signal that is not a true R-wave. When the R-wave criteria are not met by the ECG signal segment, control circuit 80 determines that the first, earliest ventricular sensed event signal 424 is an invalid event signal. In this case, control circuit 80 controls therapy delivery circuit 84 to withhold the pending cardiac pacing pulse 466 until the validation window 426 expires. In response to control circuit 80 determining an invalid event signal, therapy delivery circuit 84 may deliver the pending cardiac pacing pulse 466' at the expiration of the validation window 426. When control circuit 80 determines that the R-wave morphology criteria are not met based on the ECG signal segment analysis, and the validation window 426 expires without a second ventricular sensed event signal from the other sensing channel, control circuit 80 does not restart the pacing escape interval and controls therapy delivery circuit 84 to deliver the pending cardiac pacing pulse 466' previously scheduled for delivery upon expiration of the pacing escape interval 464. The withheld pending pacing pulse 466 is effectively delayed until the end of the validation window 426. A pacing latency 482 between the time of the expiration of pacing escape interval 464 to the time of the delivered pacing pulse 466' may occur. Pacing latency 482 may be as long as the duration of the validation window 426 in some instances. Control circuit 80 may be configured to process and analyze the ECG signal segment stored over total morphology analysis time interval 435 within a processing time interval 438 that is completed by the expiration of the validation window 426 to avoid excessive latency in delivering a pending pacing pulse that is withheld due to pacing escape interval expiration during the validation window 426.

In some examples, the second portion of the ECG signal segment stored over storage interval 436 after the first, earliest ventricular sensed event signal 424 and the processing time interval 438 combined may be a total of 100 to 110 ms so that pacing pulse 466' is delivered no later than 110 ms after the first, earliest ventricular sensed event signal 424. When storage interval 436 is 90 ms and validation window 426 is 105 ms, processing time interval 438 may be approximately 15 ms or less so that pacing pulse 466' can be delivered within 5 ms from the expiration of validation window 426. In this way, if ventricular sensed event signal 424 is determined to be an invalid event signal but is in fact a true R-wave such that control circuit 80 determines a false invalid event signal, the pacing pulse 466' is delivered before the vulnerable period corresponding to repolarization of the myocardial tissue following the true R-wave. In some patients, pacing during the vulnerable period may induce tachyarrhythmia.

In other examples, when control circuit 80 determines that a first, earliest ventricular sensed event signal 424 is an invalid event signal, control circuit 80 may set a pace delay interval 484 to reschedule the pending pacing pulse 466 for delivery after a vulnerable period if a false invalid event signal determination is made. The pace delay interval 484 may be set by control circuit 80 to be 400 ms, 600 ms, 800 ms, or 1 second after the expiration of the pacing escape interval 464, as examples, to promote delivery of a pacing pulse 466" after the vulnerable period if the first ventricular event signal 424 corresponds to a true R-wave 414. While the pace delay interval 484 is shown to be started upon expiration of the pacing escape interval 464 in FIG. 10, in other examples the pace delay interval 484 may be started upon expiration of the validation window 426. If pacing escape interval 464 expires and the first, earliest ventricular event signal 424 is determined to be an invalid event signal, the pending pacing pulse 466 may be withheld until the pace delay interval 484 expires. A pacing pulse 466" may be delivered at the expiration of the pace delay interval 484. It is to be understood that only one of the pacing pulses 466' or 466" is delivered in response to the expiration of the pacing escape interval 464 during the validation window when an invalid event signal determination is made. Both pacing pulses 466' and 466" are shown for the sake of illustrating different examples of when a pending pacing pulse 466 that is withheld at the expiration of the pacing escape interval 464 can be delivered. A latent pacing pulse, shown as pacing pulse 466' in FIG. 10, may be delivered after expiration of the validation window 426 when a pace delay interval 484 is not set. The latent pacing pulse delivery allows control circuit 80 to complete processing and analysis required to determine an invalid event signal. A delayed pacing pulse shown as pacing pulse 466" may be delivered at the expiration of the pace delay interval 484 when the pace delay interval 484 is set for avoiding pacing into the vulnerable period when an invalid event determination is false.

Figure 11:
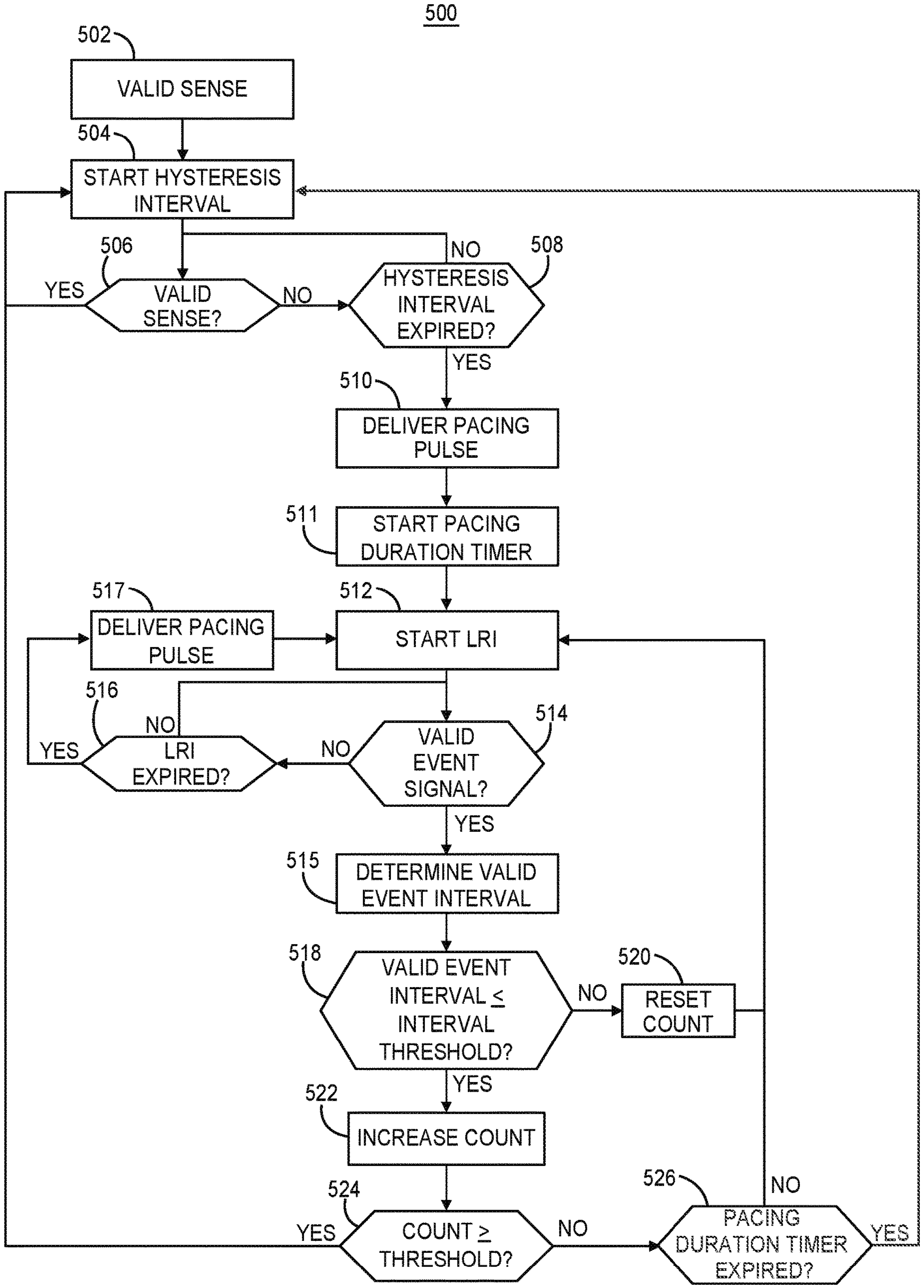
FIG. 11 is a flow chart of a method for controlling cardiac pacing by the ICD of FIG. 3 according to some examples.

FIG. 11 is a flow chart 500 of a method for controlling cardiac pacing by ICD 14 according to some examples. At block 502, control circuit 80 identifies a valid event signal according to any of the examples described herein. In response to the valid event signal, control circuit 80 starts a pacing escape interval at block 504. The pacing escape interval is set to a hysteresis interval at block 504 when no pacing pulses have been delivered over a predetermined number of the most recent preceding ventricular cycles in some examples. As described below, when pacing is inhibited for a series of consecutive ventricular cycles due to ventricular sensed event signals occurring faster than the programmed lower pacing rate, control circuit 80 may set the pacing escape interval to a hysteresis interval so that pacing is not restarted until the heart rate falls below the rate associated with the hysteresis interval. In an example, the programmed lower rate may be 50, 60 or 70 pulses per minute. The hysteresis rate is less than the programmed lower rate and may be 10, 12, 15, 20, 25, 30 or 40 pulses per minute, as examples. The pacing escape interval can be set to a hysteresis interval of 4,000 ms, as an example, at block 504 when pacing pulse delivery has not occurred recently, e.g., within the most recent 20 seconds, 30 seconds, 40 seconds or 60 seconds, as examples, or within the last six, eight, ten or other predetermined number of ventricular cycles. In other examples, as described below, the pacing escape interval may be set to the hysteresis interval at block 504 when pacing at the lower rate for a predetermined time interval, e.g., 30 to 60 seconds, has occurred in order to minimize pacing frequency.

When a valid event signal is identified by control circuit 80 at block 506 before the hysteresis interval expires (as determined at block 508), control circuit 80 restarts the pacing escape interval set to the hysteresis interval at block 504. In some instances, the hysteresis interval may expire during the validation window. As described above, the first, earliest ventricular sensed event signal may be subsequently validated based on a second ventricular sensed event signal within the validation window or based on R-wave criteria being met according to ECG signal segment morphology analysis. In this case, the hysteresis interval may be restarted having an effective starting time coinciding with the single ventricular sensed event signal when validated based on morphology analysis or coinciding with the midpoint between the first, earliest ventricular sensed event signal and the second, later ventricular sensed event signal received within the validation window.

When a valid event signal is not identified by control circuit 80 and the hysteresis interval expires at block 508, therapy delivery circuit 84 generates and delivers a pacing pulse at block 510. In some instances, no ventricular sensed event signal is received during the hysteresis interval, resulting in a pacing pulse generated and delivered at the expiration of the hysteresis interval. In other instances, the hysteresis interval started at block 504 may expire during the validation window following a single ventricular sensed event signal that is not subsequently validated. In this case, control circuit 80 may withhold the pending cardiac pacing pulse scheduled at the expiration of the hysteresis interval and control the therapy delivery circuit 84 to deliver the pending pacing pulse at block 510 at the expiration of the validation window (or after a pace delay interval).

In response to the pacing pulse delivered due to a hysteresis interval expiring, control circuit 80 restarts the pacing escape interval set to the lower rate interval (LRI) at block 512. In some examples, control circuit 80 may start a pacing duration timer at block 511 in response to a hysteresis pacing pulse being delivered and the pacing LRI escape interval being started. Control circuit 80 may limit the duration of pacing at the LRI because pacing pulses delivered from electrodes implanted in an extracardiac location may be perceivable by the patient. As such, pacing frequency, e.g., for treating bradycardia, may be minimized by limiting the duration of episodes of pacing at the LRI to provide sufficient ventricular rate support while minimizing potential patient discomfort.

The LRI is the pacing interval, e.g., 1,500 ms to 1,000 ms, corresponding to the programmed lower rate, e.g., 40 to 60 pulses per minute. The lower rate is the lowest pacing rate at which two consecutive pacing pulses are to be scheduled with the exception of a hysteresis interval. A pacing pulse scheduled at the LRI following a preceding pacing pulse may actually be delivered at a rate that is slightly less than the programmed lower rate due to rate jitter that may occur when the pacing escape interval expires during the validation window as explained above, e.g., in conjunction with FIG. 9. Control circuit 80 adjusts (or changes) the next pacing escape interval from the hysteresis interval to be the LRI when a pacing pulse is delivered in response to a hysteresis interval that expires before or during a validation window without a ventricular sensed event signal being validated. For instance, when the programmed lower rate is set to 60 pulses per minute, control circuit 80 starts the pacing escape interval set to 1,000 ms at block 512 after delivering one pacing pulse at the hysteresis interval at block 510.

If the LRI expires at block 516, before a validation window is started or during a validation window that expires without a validated ventricular sensed event signal (as determined at block 514), therapy delivery circuit 84 generates and delivers a pacing pulse at block 517. The pacing pulse may be withheld and delivered as a latent pacing pulse at the expiration of the validation window or as a delayed pacing pulse after a pace delay interval expires when the LRI expires during the validation window, e.g., as described above in conjunction with FIG. 10. The LRI is restarted at block 512 in response to the delivered pacing pulse.

When control circuit 80 receives a ventricular sensed event signal that is validated during the LRI as determined at block 514, control circuit 80 may determine the valid event interval at block 515. The valid event interval may begin with a most recent preceding ventricular event, either a delivered pacing pulse or a previously validated ventricular sensed event signal. As described above, control circuit 80 may determine a sensed event time of a valid event signal as the time of the first, earliest ventricular event signal (e.g., when verified based on R-wave morphology criteria being met) or as the midpoint between the first earliest ventricular event signal and the second, later ventricular event signal received within the validation window. Other example methods that control circuit 80 may use for determining a sensed event time of a valid event signal that may be used in determining the valid event interval at block 515 are described above. The determined sensed event time may be used in determining the valid event interval at block 515. For example, when two consecutive valid event signals occur, the valid event interval may be determined as the time interval from a sensed event time determined for the first valid event signal to the sensed event time determined for the second valid event signal. In other examples, control circuit 80 may determine the valid event interval between two consecutive valid event signals at block 515 as the time interval from the first, earliest ventricular sensed event signal to the next, first earliest ventricular sensed event signal. Note that when two ventricular sensed event signals are received (one from each sensing channel 83 and 85) within a validation window of each other, the combination of the two ventricular sensed event signals is identified collectively as one valid event signal having a determined sensed event time such that a valid event interval is not determined between the first, earliest ventricular sensed event signal and a second, later ventricular sensed event signal that occur within the validation window from each other.

At block 518, control circuit 80 may compare the valid event interval to a hysteresis reset threshold interval. The hysteresis reset threshold interval may be set equal to or less than the LRI. In an illustrative example, if the LRI is 1,000 ms, the hysteresis reset threshold interval may be set to 970 ms, 960 ms, 950 ms or other interval that is less than the LRI. When the valid event interval is greater than the hysteresis reset threshold interval, a count of valid event intervals that are less than or equal to the hysteresis reset threshold interval may be reset to zero at block 520. Control circuit 80 returns to block 512 to restart the LRI in response to the valid event signal. The current sensed ventricular rate based on the valid event interval being greater than the hysteresis reset threshold interval is near or slower than the programmed lower rate. The LRI remains in effect as the pacing escape interval for scheduling pacing pulses.

When the valid event interval is less than or equal to the hysteresis reset threshold interval at block 518, control circuit 80 increases a count of valid event intervals that are shorter than the LRI at block 522. When the count of valid event intervals less than or equal to the hysteresis reset threshold interval reaches a reset threshold value at block 524, control circuit 80 returns to block 504 to set the pacing escape interval to the hysteresis interval in response to the valid event signal. The hysteresis interval may be set to have an effective starting time coinciding with the determined sensed event time of the current valid event signal. In this way, when a threshold number of valid event signals are occurring at or faster than a threshold rate (corresponding to the hysteresis reset threshold interval) that is faster than the programmed lower rate, control circuit 80 reverts back to setting the pacing escape interval equal to the hysteresis interval.

If the count of valid event intervals that are less than or equal to the hysteresis reset threshold interval has not reached a reset threshold value ("no" branch of block 524), control circuit 80 may restart the pacing escape interval set to the LRI by returning to block 512. The intrinsic ventricular rate has not reached a sustained rate faster than the programmed lower rate that warrants reverting back to the hysteresis pacing rate. In other examples, control circuit 80 may determine a count of valid event intervals that are less than a hysteresis reset threshold interval set equal to the LRI. This, however, may result in switching between the LRI and the hysteresis interval more frequently than when the hysteresis reset threshold interval is set to be less than the LRI. In still other examples, control circuit 80 may count the number of pacing pulses scheduled at the LRI that are inhibited due to a valid event signal and compare the count of inhibited LRI pacing pulse to the threshold value at block 524.

In this way, control circuit 80 may control the pacing escape interval to be set to the hysteresis interval or a LRI based on the rate of validated sensed event signals. Control circuit 80 may revert back to setting the pacing escape interval to the hysteresis interval when the intrinsic heart rate is faster than the programmed lower rate (corresponding to the LRI) for at least a threshold number of ventricular cycles. In other examples, instead of or in addition to counting validated sensed event signals or valid event intervals during lower rate pacing, control circuit 80 may set a pacing duration timer as shown at block 511. Therapy delivery circuit 84 may deliver pacing pulses at the LRI for a predetermined maximum pacing duration, e.g., 30 seconds, one minute, two minutes or other selected time interval. If control circuit 80 determines that the pacing duration timer has expired at block 526, control circuit 80 may revert back to setting the pacing escape interval to the hysteresis interval by returning to block 504. When control circuit 80 determines that the pacing duration timer has not yet expired, control circuit 80 may return to block 512 to restart the pacing escape interval set to the LRI. While block 526 is shown after block 524 in flow chart 500 for the sake of convenience, it is to be understood that control circuit 80 may detect the expiration of the pacing duration timer at any time during the process of determining valid event signals and/or delivering pacing pulses. Whenever the pacing duration timer expires, control circuit 80 may return to block 504.

In some examples, control circuit 80 may control the duration of pacing at the LRI only by setting a pacing duration timer without determining a count of valid event signals or valid event intervals that are less than or equal to an interval threshold. For example, a pacing duration timer may limit the maximum time duration that control circuit 80 sets the pacing escape interval to the LRI (whether pacing pulses are delivered at the LRI or not) until reverting back to setting the pacing escape interval to the hysteresis interval. In other examples, blocks 511 and 526 may be omitted such that control circuit 80 controls the duration of pacing at the lower rate based on a count of valid event signals (or inhibited pacing pulses) and/or by counting the valid event intervals that are shorter than the LRI or shorter than a hysteresis reset interval threshold.

Figure 12:
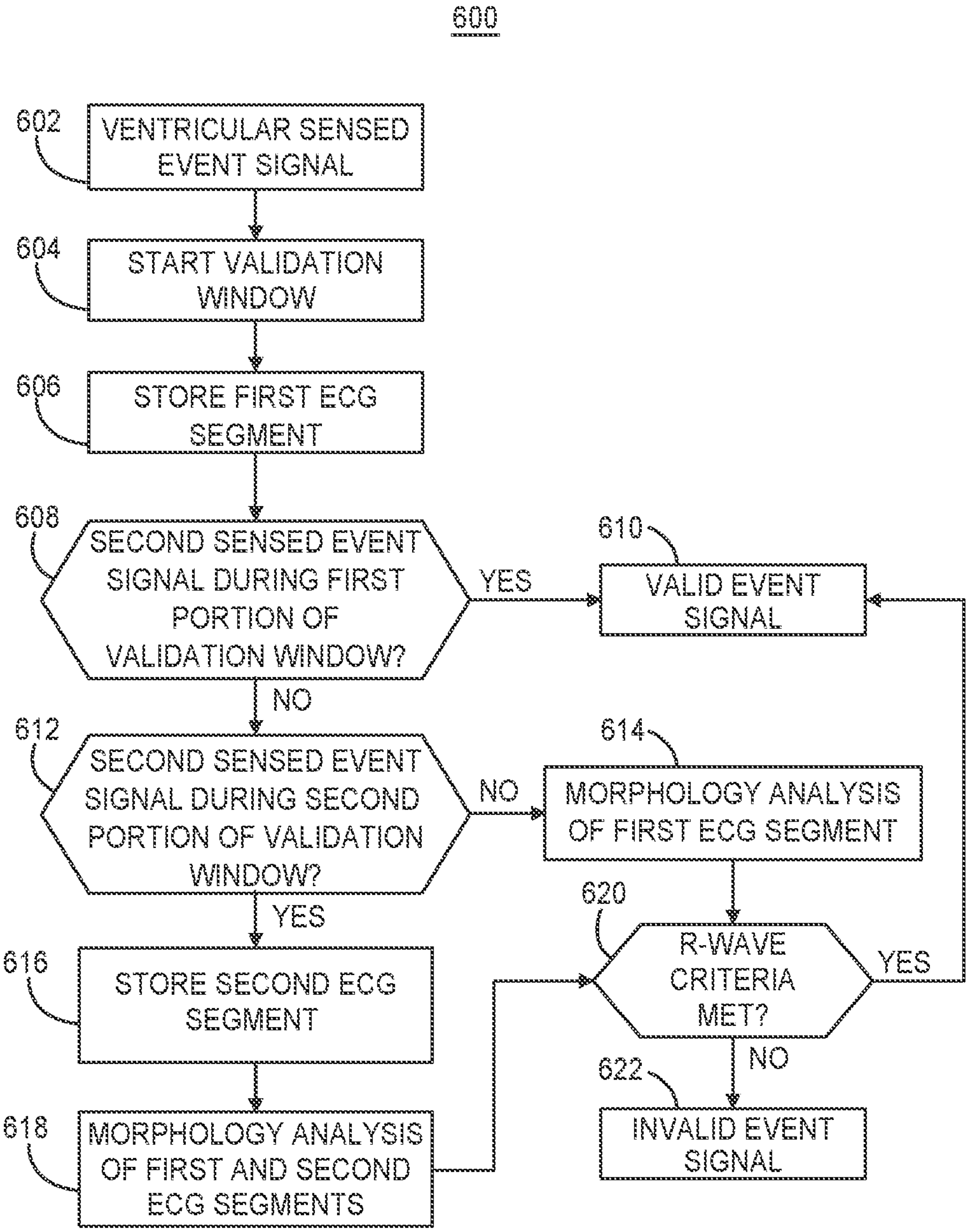
FIG. 12 is a flow chart of a method for validating ventricular sensed event signals according to another example.

FIG. 12 is a flow chart 600 of a method for validating ventricular sensed event signals according to another example. In this example, morphology analysis may be required to be performed depending on when a second, later ventricular sensed event signal is received by control circuit 80 during the validation window. At block 602, control circuit 80 receives a first, earliest ventricular sensed event signal from one of sensing channels 83 or 85 outside of a validation window. As described above, in response to the first, earliest ventricular sensed event signal, control circuit 80 may start the validation window at block 604. Additionally, control circuit 80 may store an ECG signal segment at block 606 by freezing a buffered portion of the ECG signal received from morphology signal channel 87 as a first portion of an ECG signal segment at block 606 and continuing to store the ECG signal for a next storage interval to append the second portion of an ECG signal segment to the first portion.

Control circuit 80 may determine if a second ventricular sensed event signal is received during a first portion of the validation window at block 608. When the second ventricular sensed event signal is received within the first portion of the validation window, control circuit 80 determines that the first, earliest ventricular sensed event signal is a valid event signal at block 610. The first portion of the validation window may be the earliest 20 ms, 30 ms, 40 ms, 50 ms, 60 ms, one fourth, one half, or other specified portion of the validation window. In response to the valid event signal, control circuit 80 may restart a pacing escape interval according to any of the techniques described above.

When control circuit 80 receives a second, later sensed event signal after the first portion of the validation window but within a second portion of the validation window ("yes" branch of block 612), control circuit 80 may perform morphology analysis on the ECG signal segment stored at block 606 in order to validate the first, earliest ventricular sensed event signal. In some examples, control circuit 80 may additionally perform morphology analysis on a second ECG signal segment corresponding to the second, later ventricular sensed event signal. As such, control circuit 80 may store a second ECG signal segment at block 616 in response to the second, later ventricular sensed event signal received at block 612. Memory 82 may include multiple buffers for storing multiple ECG signal segments received from the morphology signal channel 87. The second ECG signal segment may be stored at block 616 to encompass the time of the second ventricular sensed event signal, e.g., according to the techniques described above for storing the first ECG signal segment.

At block 618, control circuit 80 may perform morphology analysis of one or both of the first and the second ECG signal segments in response to the second, later ventricular sensed event signal being received during the later portion of the validation window. The morphology analysis may be performed according to any of the example techniques described above. At block 620, control circuit 80 may determine if R-wave criteria are met based on the morphology analysis. In some examples, only one ECG signal segment may be required to meet the R-wave criteria when two ventricular sensed event signals are received within the second portion of the validation window from each other. In some cases, the first, earliest ventricular sensed event signal may be noise or an oversensed P-wave, and the second, later ventricular sensed event signal may correspond to a true R-wave. In this case, the second, later ventricular sensed event signal may be determined to be a valid event signal. The sensed event time may be determined as the time of the second, later ventricular sensed event signal.

In other examples, when at least one ECG signal segment meets the R-wave criteria, a valid event signal may be determined at block 610. Control circuit 80 may determine that the sensed event time of the valid event signal is the midpoint of the time between the first, earliest ventricular event signal and the second, later ventricular event signal. Alternatively, control circuit 80 may determine that the sensed event time is the time of the ventricular sensed event signal corresponding to the ECG signal segment that met the R-wave criteria. A pacing escape interval may be restarted in response to the valid event signal with an effective starting time corresponding to the determined sensed event time as described above.

The morphology analysis of the second ECG signal segment may be performed over a shorter buffered segment and/or using morphology features and comparisons that minimize processing time required to make a valid or invalid event signal decision. In order to avoid excessive latency in pacing pulse delivery when an invalid event determination is made, the morphology analysis of the second, later ECG signal segment may need to be abbreviated or in some cases abandoned if the analysis cannot be completed within an acceptable time interval, e.g., within 10 to 30 ms, after the expiration of the validation window.

When control circuit 80 determines that R-wave criteria are not met by either of the first or second ECG signal segments at block 620, control circuit 80 determines at block 622 that the first and second ventricular sensed event signals are invalid and unlikely to correspond to a true R-wave. In this case, both sensing channels 83 and 85 may be oversensing myopotential noise, for instance. In response to determining an invalid event signal, a pacing escape interval that is running may continue to run. If a pacing escape interval expired during the validation window, a pending pacing pulse scheduled at the expiration of the pacing escape interval may be delivered upon expiration of the validation window (or after a pace delay interval) in response to determining that the first earliest and second, later ventricular sensed event signals are invalid. The determination that the first, earliest and the second, later ventricular sensed event signals are invalid by control circuit 80 may be delayed when morphology analysis is performed on a second ECG signal segment acquired in response to the second, later ventricular sensed event signal being received in the second, later portion of the validation window. The additional processing time may delay delivery of a withheld, pending cardiac pacing pulse by more than the duration of the validation window after the first, earliest ventricular sensed event signal. In some examples, the morphology analysis performed in response to the second, later ventricular sensed event signal may use a shorter ECG signal segment and/or morphology features that require less processing time to determine and analyze to reduce the processing time required to make a valid or invalid event decision.

In order to avoid delivering a pending pacing pulse during the vulnerable period after a true R-wave that is falsely determined to be an invalid sensed event, control circuit 80 may control the therapy delivery circuit to delay the pending pacing pulse for the pace delay interval after the validation window to ensure that the pacing pulse is delivered after a possible vulnerable period when the invalid sensed event determination is a false determination. For example, control circuit 80 may set a pace delay interval to 500 ms, 600 ms or more following the first, earliest ventricular sensed event signal or following the expiration of the validation window. A pending pacing pulse that is withheld during the validation window may be delivered upon expiration of the pace delay interval.

It is to be understood that if a valid event signal is determined by control circuit 80 during the pace delay interval, the pending pacing pulse scheduled at the expiration of the pace delay interval may be cancelled and a pacing escape interval restarted. If another invalid event signal is determined during the pace delay interval, however, therapy delivery circuit 84 may deliver the pending pacing pulse at the expiration of the pace delay interval, without starting another pace delay interval in response to the second consecutive invalid event signal. In this way, postponing the pending pacing pulse for more than one pace delay interval may be avoided when valid event signals are not determined. Control circuit 80 may start the pace delay interval up to a maximum number of times in response to consecutive invalid event signals in order to avoid a long interval of no valid event signal or pacing pulses.

Referring again to block 612, when a second, later ventricular sensed event signal is not received during the validation window ("no" branch of block 612), control circuit 80 may perform morphology analysis of the first ECG signal segment at block 614. When the first ECG signal segment meets R-wave criteria at block 620, control circuit 80 may determine that the single (first, earliest) ventricular sensed event signal is a valid event signal at block 610. If R-wave criteria are unmet by the first ECG signal segment, the single ventricular sensed event signal is determined to be invalid at block 622.

In some examples, the R-wave criteria applied to the first ECG signal segment at block 620 may be more stringent for determining a valid event signal when a single ventricular sensed event signal is received than when two ventricular sensed event signals are received within the validation window and both the first and second ECG signal segments are analyzed. For instance, more stringent R-wave criteria could require that a greater number of features of the first ECG signal segment are determined. For example, instead of two morphology features being determined such as the morphology matching score and the peak amplitude, three or more features may be determined, e.g., adding QRS width, QRS area, slope and/or other features. The greater number of morphology features may be compared to corresponding R-wave criteria. Additionally or alternatively, more stringent R-wave criteria applied to features of the ECG signal segment may include thresholds, ranges or values of the R-wave criteria that are increased, decreased or narrowed, for example, to be more stringent to increase the confidence or specificity of detecting a true R-wave present in the ECG signal segment when a single ventricular sensed event signal is received.

As an example, if a morphology matching score is determined, a higher morphology matching score threshold may be applied to the morphology matching score determined from the first ECG signal segment when only one ventricular sensed event signal is received than when a second, later ventricular sensed event signal is received during the validation window. Additionally or alternatively, a higher threshold or narrower range may be applied to the maximum amplitude and/or to the slope difference determined from the first ECG signal segment. In other examples, instead of or in addition to using more stringent thresholds, ranges or values applied to the ECG signal segment features, additional ECG signal segment features may be determined and compared to respective criteria. For instance, if the morphology matching score, maximum peak amplitude, and peak-to-peak amplitude of the first order difference signal are determined from each of the first and second ECG signal segments when two ECG signal segments are analyzed, control circuit 80 may additionally determine a noise pulse count, number of zero crossings, signal width of the signal pulse having a maximum peak amplitude in the ECG signal segment or other morphology feature(s) or any combination thereof and compare these additional feature(s) to respective threshold(s), range(s), or value(s) corresponding to a true R-wave, which may be a sinus R-wave or an aberrantly conducted R-wave.

Figure 13:
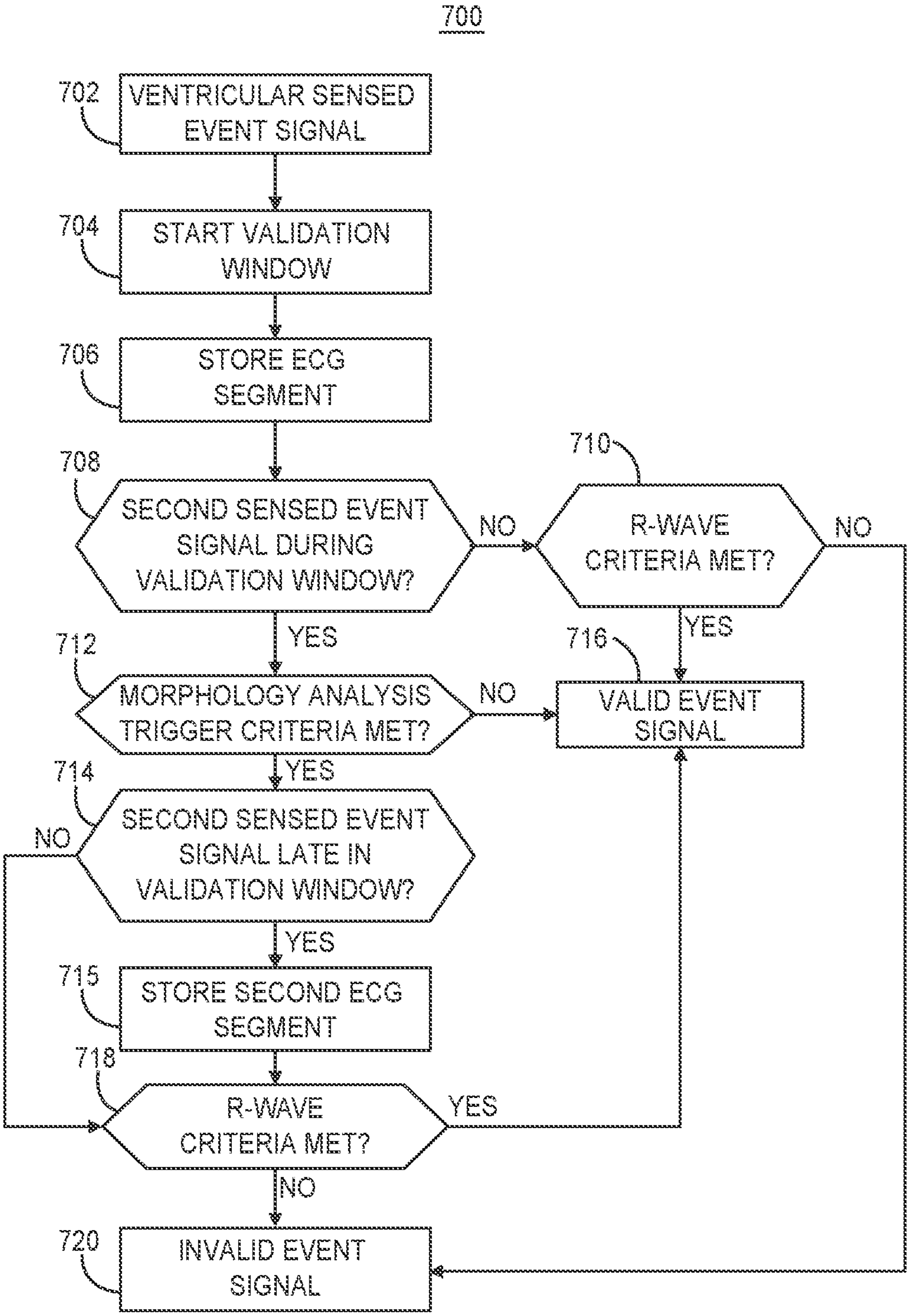
FIG. 13 is a flow chart of a method for validating a ventricular sensed event signal according to yet another example.

FIG. 13 is a flow chart 700 of a method for validating a ventricular sensed event signal according to yet another example. In this example, control circuit 80 may perform morphology analysis depending on the maximum peak amplitude of the sensed signal, the time of an R-wave sensing threshold crossing following a preceding ventricular event, and/or the R-wave sensing threshold amplitude that is crossed resulting in a ventricular sensed event signal produced by sensing circuit 86. When a ventricular sensed event signal is generated by sensing circuit 83 or 85 when the R-wave sensing threshold amplitude is at the sensing floor, for example, there is a greater likelihood that the sensed event is a P-wave, T-wave, myopotential noise or other noise. When the maximum peak amplitude determined during the R-wave peak tracking period is relatively small, the sensed event signal may be noise. Accordingly, morphology analysis may be performed to increase the confidence in a valid event signal determination when relatively small maximum peak amplitude signals are sensed and/or when the event signal is sensed when the R-wave sensing threshold is at the programmed sensitivity.

At block 702, control circuit 80 receives a first, earliest ventricular sensed event signal from one of sensing channels 83 or 85 outside of a validation window. In response to the first, earliest ventricular sensed event signal, control circuit 80 may start a validation window at block 704. Additionally, control circuit 80 may freeze a buffered portion of the ECG signal received from morphology signal channel 87 as a first portion of an ECG signal segment and continue storing the ECG signal for a next storage interval to append a second portion of an ECG signal segment to the first portion at block 706.

Control circuit 80 determines if a second ventricular sensed event signal is received during the validation window at block 708. When a second ventricular sensed event signal is not received before the expiration of the validation window, control circuit 80 determines at block 710 if R-wave criteria are met based on morphology analysis of the stored ECG signal segment as described above. If the R-wave criteria are met, the first ventricular sensed event signal is identified as a valid event signal at block 716. If not, control circuit 80 determines that the single ventricular sensed event signal is an invalid sensed event signal at block 720.

When a second, later ventricular sensed event signal is received within the validation window ("yes" branch of block 708), control circuit 80 may determine at block 712 if morphology analysis trigger criteria are met. In one example, if the maximum peak amplitude of the first, earliest ventricular sensed event signal and/or the maximum peak amplitude of the second, later ventricular sensed event signal is less than a predetermined threshold amplitude, morphology analysis may be triggered by control circuit 80 even though a second, later ventricular sensed event signal is received. The predetermined threshold amplitude may be a specified amplitude that may be programmable, e.g., 0.1 to 1.0 mV. In an example, if both maximum peak amplitudes of the first and the second ventricular sensed event signals received within the validation window are less than 0.5 mV, control circuit 80 may determine that the morphology analysis trigger criteria are met at block 712. In other examples, the predetermined threshold amplitude may be a percentage or multiple of the programmed sensitivity, e.g., 1.25 or 1.5 times the programmed sensitivity of the respective sensing channel.

Additionally or alternatively, if either or both of the first, earliest ventricular sensed event signal or the second, later ventricular sensed event signal was generated when the R-wave sensing threshold of the respective sensing channel 83 or 85 was at the sensing floor, control circuit 80 may determine that the morphology analysis trigger criteria are met at block 712. In some instances, the R-wave sensing threshold may remain at the sensing floor for up to two seconds, three seconds, four seconds or longer e.g., when the pacing escape interval is set to the hysteresis interval. Once the R-wave sensing threshold is adjusted down to the sensing floor, noise or P-waves may cross the sensing threshold on one or both sensing channels. In some instances, the maximum peak amplitude of a sensed event signal that is determined for setting the starting R-wave sensing threshold is low, so that the percentage of the maximum peak amplitude used to set the starting R-wave sensing threshold is near or less than the minimum sensing threshold. In these instances, the R-wave sensing threshold may already be set to the sensing floor during the first drop time interval and/or during the second drop time interval (see FIG. 9). When a second ventricular sensed event signal is received within the validation window after the first ventricular sensed event signal and the sensing threshold is at the sensing floor for one or both sensing channels 83 and/or 85 when the respective ventricular sensed event signal was generated, an oversensed P-wave or noise sensed by one or both sensing channels at the sensing floor could result in a false valid event signal determination and cause a scheduled pacing pulse to be inhibited when it is actually needed.

In still other examples, the morphology analysis trigger criteria applied by control circuit 80 at block 712 may require that one or both of the first, earliest ventricular sensed event signal or the second, later ventricular sensed event signal is received at an in-channel sensed event time interval that is greater than a predetermined time interval threshold. The predetermined time interval threshold may be set based on the second drop time interval (448 or 458 shown in FIG. 9). Upon expiration of the second drop time interval 448 or 458, the R-wave sensing threshold is adjusted to the sensing floor if not already at the sensing floor. In some examples, the morphology analysis trigger criteria are met at block 712 when one or both of the first, earliest ventricular sensed event signal and/or the second, later ventricular sensed event signal is received after the second drop time interval expires for the respective sensing channel 83 or 85. In this case, the morphology analysis trigger criteria may not be met when a given ventricular sensed event signal is received at an in-channel sensed event interval that is less than the second drop time interval, even if the R-wave sensing threshold is already at the sensing floor earlier than the expiration of the second drop time interval due to a relatively low maximum peak amplitude of the preceding sensed event signal used to set the starting R-wave sensing threshold.

Therefore at block 712, control circuit 80 may determine when morphology analysis trigger criteria are met by comparing the maximum peak amplitude determined during the R-wave peak tracking window to an amplitude threshold, comparing the in-channel sensed event interval to a threshold interval (which may be based on the second drop time interval), and/or determining whether the sensing threshold is at the sensing floor when a ventricular sensed event signal is received (independent of the in-channel sensed event interval). Control circuit 80 may analyze the stored ECG signal segment to verify that R-wave criteria are met when the morphology analysis trigger criteria are met even though the second, later ventricular sensed event signal was received during the validation window.

When the morphology analysis trigger criteria are not met for either sensing channel 83 or 85, control circuit 80 may determine that the first, earliest ventricular sensed event signal (and the second, later ventricular sensed event signal, collectively) is a valid event signal at block 716 in response to the second, later ventricular event signal that occurs within the validation window. When the morphology analysis trigger criteria are met by at least one of the sensing channels 83 or 85, however, control circuit 80 may perform morphology analysis on the stored ECG signal segment at block 718 to determine if R-wave criteria are met.

In some examples, as shown in FIG. 13, control circuit 80 may determine if the second ventricular sensed event signal occurs later than a threshold time interval within the validation window at block 714. When the first and second ventricular sensed event signals are more than a threshold time interval apart, the morphology analysis of the ECG signal segment stored at block 706 in response to the first, earliest ventricular sensed event signal may yield a different result than morphology analysis of an ECG signal segment that is stored in response to the second, later ventricular sensed event signal. As such, control circuit 80 may store an ECG signal segment at block 715 in response to the second, later ventricular sensed event signal being more than a threshold time interval after the first, earliest ventricular sensed event signal but within the validation window ("yes" branch of block 714). The threshold time interval may be 30 ms, 40 ms, 50 ms, 60 ms, 70 ms, 80 ms, or 90 ms in various examples. In this case, memory 82 may be configured to store the ECG signal segment at block 706 in response to the first, earliest ventricular sensed event signal outside a validation window and continue buffering the ECG signal received from morphology channel 87. In this way, memory 82 is enabled to store a second ECG signal segment at block 715 encompassing the time of the second, later ventricular sensed event signal. When the second, later ventricular sensed event signal occurs after a threshold time interval within the validation window (as determined at block 714), memory 82 stores the second ECG signal segment at block 715 so that both ECG signal segments, one encompassing the time of at least the first ventricular sensed event signal and one encompassing the time of at least the second ventricular sensed event signal, can be analyzed by control circuit 80. In other examples, a single longer ECG signal segment may be stored when two ventricular sensed event signals occur within the validation window.

When the second, later ventricular sensed event signal is received within a threshold time interval (relatively early) after the first, earliest ventricular sensed event signal ("no" branch of block 714), control circuit 80 analyzes the first ECG signal segment (stored at block 706) to determine if R-wave criteria are met at block 718. A second ECG signal segment may not be stored in response to the second, later ventricular sensed event signal. When both the first and second ventricular sensed event signals are received within the threshold time interval corresponding to an early portion of the validation window, the two ECG signal segments would be largely overlapping. The morphology analysis of the two ECG signal segments would likely yield the same result. Accordingly, at block 718 the R-wave criteria may be applied only to the first ECG signal segment and may include any of the example criteria described above.

When the second sensed event signal is late in the validation window, less overlap between two different ECG signal segments stored in response to the two ventricular sensed event signals separated by at least the time interval threshold may yield different results of the morphology analysis. Control circuit 80 may therefore store a second ECG signal segment at block 715 in response to the second, later ventricular sensed event signal when it is more than a threshold time interval after the first, earlier ventricular sensed event signal. Both the first and the second ECG signal segments may be analyzed at block 718. In some examples, control circuit 80 analyzes the first ECG signal segment as soon as it is available while waiting for the second, later ventricular sensed event signal and second ECG signal segment to be stored. If the first ECG signal segment meets the R-wave criteria at block 718, control circuit 80 determines the first, earliest ventricular sensed event signal to be a valid event signal at block 716. If the first ECG signal segment does not meet the R-wave criteria at block 718, control circuit 80 may analyze the second ECG signal segment. When the second ECG signal segment meets the R-wave criteria, control circuit 80 determines a valid event signal at block 716. The sensed event time may be determined to be the time of the second ventricular sensed event signal because the corresponding ECG signal segment met the R-wave criteria. Alternatively, the sensed event time may be determined as the midpoint between the first and second ventricular sensed event signals. If neither of the first or the second ECG signal segments meet the R-wave criteria at block 718, control circuit 80 determines an invalid event signal at block 720. In various examples, control circuit 80 may analyze one or both ECG signal segments in a sequential or parallel manner and when at least one ECG signal segment meets the R-wave criteria at block 718, a valid event signal is identified. It is to be understood that the R-wave criteria applied at block 718 may include criteria for identifying both normally conducted R-waves and aberrantly conducted R-waves or ectopic beats as generally described above in conjunction with FIG. 6.

In some examples, the R-wave criteria applied at block 718 when one or both of the first and second ventricular event signals were sensed at the sensing floor and separated by a threshold interval may be different than the R-wave criteria applied at block 710. For example, the R-wave criteria applied at block 718 may be more stringent than the R-wave criteria at block 710, by including more restrictive criteria and/or applying criteria to additional morphology features than the criteria applied at block 710. Examples of relatively more stringent R-wave criteria are described above.

When the R-wave criteria are not met at block 718, a pacing escape interval continues to run and is not restarted in response to the first and second ventricular sensed event signals determined collectively as an invalid event signal. If a pacing escape interval expires during the validation window or before the morphology analysis of the two ECG signal segments is complete, therapy delivery circuit 84 may withhold a pending cardiac pacing pulse. In response to an invalid event signal determination, control circuit 80 controls therapy delivery circuit 84 to deliver the withheld, pending pacing pulse upon expiration of the validation window or upon reaching the invalid event signal determination, whichever is later. In some examples, control circuit 80 may control therapy delivery circuit 80 to re-schedule the withheld, pending pacing pulse at a pace delay interval as described above to avoid pacing into the vulnerable period.

When the R-wave criteria are met at block 718, control circuit 80 may restart a pacing escape interval, which may have an effective starting time coinciding with a determined sensed event time. The pacing escape interval may be restarted so that its starting time corresponds to the time of the first ventricular sensed event signal, the midpoint time between the two ventricular sensed event signals, the time of the second ventricular sensed event signal, the time of the ventricular sensed event signal associated with the ECG signal segment found to meet the R-wave criteria at block 718, or the expiration of the validation window. The pacing escape interval may be the LRI or a hysteresis interval.

Figure 14:
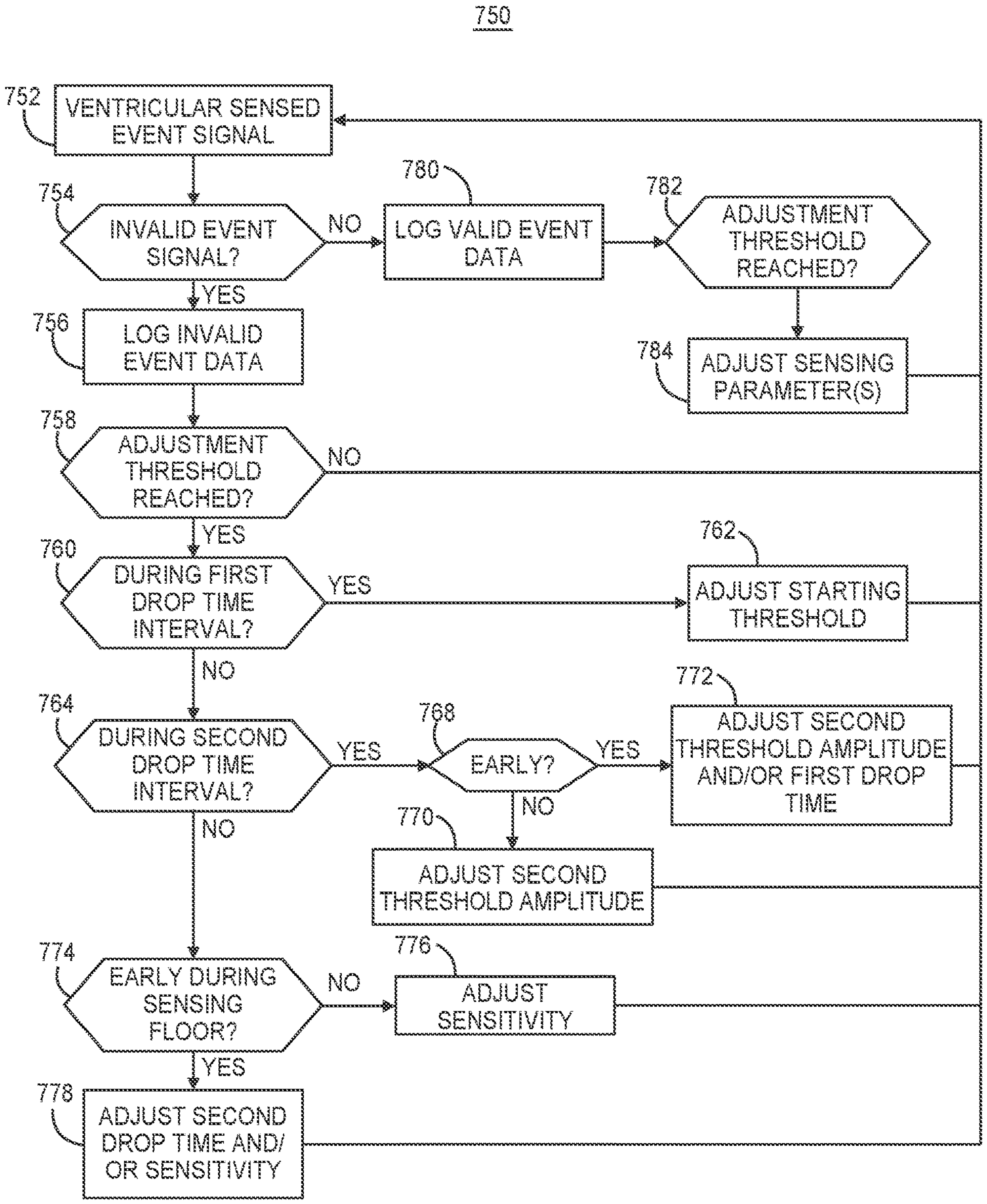
FIG. 14 is a flow chart of a method that may be performed by the ICD of FIG. 3 for adjusting R-wave sensing control parameters in response to the determination of valid and invalid event signals according to some examples.

FIG. 14 is a flow chart 750 of a method that may be performed by control circuit 80 for adjusting R-wave sensing control parameters in response to the determination of valid and invalid event signals according to some examples. R-wave sensing control parameters may include the blanking period and various control parameters used in adjusting the R-wave sensing threshold from a starting amplitude to the minimum amplitude, e.g., one or more drop time intervals, percentages used to set the R-wave sensing threshold amplitude to a percentage of the maximum peak amplitude of a sensed event, and the programmed sensitivity. R-wave sensing control parameters include any of the parameters described in conjunction with FIG. 9 used in adjusting the R-wave sensing threshold amplitude in some examples.

At block 752, control circuit 80 receives a ventricular sensed event signal. Control circuit 80 identifies the sensed event signal as a valid or invalid sensed event signal at block 754 according to any of the techniques disclosed herein. When a ventricular sensed event signal is identified as invalid ("yes" branch of block 754), control circuit 80 may log invalid event signal data in memory 82 at block 756. Control circuit 80 may increment a counter of invalid event signals at block 756 to track the frequency of invalid event signals. The counter may be increased by one in response to each invalid event signal and may be reset to zero when a threshold number of valid event signals occur. The counter may be a first in first out buffer that stores a predetermined number, e.g., 8, 12, 16, 20, 30 or other selected number of sensed event signal classifications. In other examples, the number of invalid event signals that occur over a predetermined time interval, e.g., 30 seconds, one minute, two minutes, five minutes or other time interval, may be counted. When a threshold count of invalid event signals or a threshold frequency of X out of Y invalid event signals is reached, control circuit 80 may determine that an adjustment threshold is reached at block 756. In various examples, the adjustment threshold may be reached when a threshold percentage of a predetermined number of sensed event signals from a given sensing channel reaches a threshold percentage or ratio of invalid to valid (or all) sensed event signals from the sensing channel.

In some examples, in addition to tracking the count or frequency of invalid event signals at block 756, control circuit 80 may log data relating to the invalid event signals for use in determining an R-wave sensing threshold adjustment. Data that may be determined by control circuit 80 and stored in memory 82 in response to each invalid event signal at block 756 may include the maximum peak amplitude of the cardiac electrical signal (of the sensing channel from which the ventricular sensed event signal identified as invalid was received), time of the maximum peak amplitude, the in-channel sensed event time interval, and/or the R-wave sensing threshold amplitude at the time of the sensed event signal, as examples.

When the adjustment threshold is reached at block 758, control circuit 80 may analyze invalid event signal data logged in memory 82 in order to determine an adjustment to an R-wave sensing control parameter. For the sake of illustration, the methods of the flow chart 750 are described assuming that the invalid event signals that reach the adjustment threshold at block 758 are received from one sensing channel, e.g., sensing channel 83 or sensing channel 85. In some cases, ventricular sensed event signals may be received from either or both sensing channels 83 and/or 85 that are identified as invalid signals over a given interval of time. Control circuit 80 may track the number of ventricular sensed event signals received from each sensing channel associated with invalid event signal determinations and log invalid event signal data in memory 82 in separate memory buffers for each sensing channel 83 and 85. In this way, control circuit 80 may perform individual adjustments of R-wave sensing control parameters used by each sensing channel 83 and 85 as needed, e.g., when the adjustment threshold is reached based on invalid event signals produced by a given sensing channel 83 or 85.

At block 760, in response to the adjustment threshold being reached, control circuit 80 may determine if a majority of the invalid event signals have occurred during the first drop time interval (e.g., interval 445 or 455 of FIG. 9) of the R-wave sensing threshold for the respective sensing channel 83 or 85 that produced the invalid sensed event signal. If so, control circuit 80 may adjust the starting sensing threshold at block 762. Control circuit 80 may adjust the starting sensing threshold, e.g., threshold amplitude 440 or 450 in FIG. 9, by adjusting the percentage used to set the starting sensing threshold as a percentage of the maximum peak amplitude (e.g., peak amplitude 408 or 418) of the cardiac electrical signal during an R-wave peak tracking portion of the blanking period (405 or 415). In some examples, control circuit 80 may determine the mean, median or greatest one of the maximum peak amplitudes that may be logged in memory 82 for the invalid event signals. Control circuit 80 may adjust the starting threshold amplitude at block 762 to be greater than the metric of the maximum peak amplitudes of the invalid event signals. The invalid event signals may be oversensed T-waves occurring during the first drop time interval due to too low starting sensing threshold amplitude.

If the invalid event signals are not received during the first drop time interval ("no" branch of block 760) but are received during the second drop time interval, ("yes" branch of block 764), control circuit 80 may determine at block 768 whether the invalid event signals were received early during the second drop time interval, e.g., early during drop time interval 448 or 458 shown in FIG. 9. For instance, control circuit 80 may determine if one or more of the invalid event signals occurred within a threshold time interval, e.g., within 50 ms, 100 ms, or 150 ms, after the expiration of the first drop time interval 445 or 455. When an invalid event signal occurs early during the second drop time interval, the invalid event signal may be an oversensed T-wave that is occurring just after the expiration of the first drop time interval 445 or 455. Control circuit 80 may increase the first drop time interval at block 772 in order to increase the likelihood of the time of the adjustment from the starting sensing threshold amplitude to the second lower sensing threshold amplitude to be later than the T-wave. Control circuit 80 may evaluate the timing of the invalid event signals, e.g., the time of the R-wave sensing threshold crossing or the time of the maximum peak amplitude since a preceding ventricular event, to select an adjusted first drop time interval that is likely to be later than the maximum peak amplitude time.

Additionally or alternatively, control circuit 80 may increase the second sensing threshold amplitude, e.g., second sensing threshold amplitude 444 or 454 in FIG. 9, at block 772 to reduce the likelihood of oversensing event signals early during the second drop time interval. Control circuit 80 may evaluate the invalid event signal data stored in memory 82 to determine a metric of the cardiac electrical signal maximum amplitudes associated with invalid event signals occurring during the second drop time interval. Control circuit 80 may adjust the second sensing threshold amplitude to be greater than a metric of the cardiac electrical signal maximum peak amplitudes associated with the invalid event signals to reduce the likelihood of oversensing T-waves (or other signals) early during the second drop time interval. For example, the percentage used to set the second sensing threshold amplitude to a percentage of the maximum peak amplitude determined during the R-wave peak tracking portion of the blanking period may be increased.

When one or more of the invalid event signals occur during the second drop time interval but later than a threshold time interval since the expiration of the first drop time interval ("no" branch of block 768), P-wave oversensing may be occurring due to the second sensing threshold amplitude being too low. When control circuit 80 determines that one or more invalid event signals occur relatively late during the second drop time interval, control circuit 80 may increase the second sensing threshold amplitude at block 770. The second sensing threshold amplitude may be increased at block 770 by increasing the percentage used for setting the second sensing threshold amplitude as a percentage of the maximum peak amplitude determined during the preceding blanking period.

At block 774, control circuit 80 may determine that one or more invalid event signals occurred early during the sensing floor, e.g., after the second drop time interval expires, when the R-wave sensing threshold is adjusted to the minimum amplitude, which may be equal to the programmed sensitivity. Control circuit 80 may determine that one or more invalid event signals are received early during the sensing floor, e.g., within a threshold time interval of 100 ms, 200 ms, or 300 ms or other threshold time interval of the expiration of the second drop time interval. When one or more invalid event signals are received early after the expiration of the second drop time interval, control circuit 80 may adjust the second drop time interval at block 778. Control circuit 80 may increase the second drop time interval to expire later than a metric of the timing of the invalid event signals that are received early during the sensing floor. For instance, control circuit 80 may determine the mean, median, or longest in-channel sensed event time or maximum peak amplitude time associated with the invalid event signals received early after expiration of the second drop time interval. Control circuit 80 may increase the second drop time interval to expire later than the metric of the time of invalid event signals occurring early after the second drop time interval expiration. Additionally or alternatively, control circuit 80 may adjust the sensitivity setting at block 778. The programmed sensitivity, used to adjust the R-wave sensing threshold to the sensing floor, e.g., minimum amplitude 403 or 413 in FIG. 9, upon expiration of the second drop time interval, may be too low, leading to oversensing of P-waves, skeletal muscle myopotentials, or other noise when the R-wave sensing threshold amplitude is at the sensing floor.

When control circuit 80 determines that at least one invalid event signal occurred relatively late during the sensing floor after the expiration of the second drop time interval ("no" branch at block 774), control circuit 80 may adjust the sensitivity at block 776. Control circuit 80 may increase the sensitivity setting (to decrease the sensitivity of the sensing channel 83 or 85 to sensing low amplitude signals) at either of blocks 776 or 778 when invalid event signals occur after the expiration of the second drop time interval.

Flow chart 750 is described assuming that all or most invalid event signals that caused the adjustment threshold to be reached occur primarily during only one of the first drop time interval, the second drop time interval, early after the second drop time interval, or when the sensing threshold is at the sensing floor. Accordingly, an adjustment may be made based on when the majority of the invalid event signals are occurring. An adjustment to the blanking period, first drop time interval and/or starting sensing threshold amplitude may be made by control circuit 80 when most invalid event signals occur during the first drop time interval. An adjustment may be made to the second drop time interval and/or the second sensing threshold amplitude when most invalid event signals occur during the second drop time interval or early after the second drop time interval. An adjustment to the programmed sensitivity may be made when most of the invalid event signals occur when the sensing threshold is at the sensing floor. In other words, the R-wave sensing control parameter that is adjusted may be based on when during the R-wave sensing threshold profile most of the invalid event signals are occurring. The adjustment may be based on the maximum peak amplitudes of the oversensed signal and/or its relative timing during the ventricular cycle. In other instances, invalid event signals may occur at varying times during the ventricular cycle, e.g., during two or more of the first drop time interval, second drop time interval and/or after the second drop time interval sensing floor. As such, while flow chart 750 indicates that control circuit 80 returns to block 752 after making an adjustment to a sensing control parameter at one of blocks 762, 770, 772, 776 or 778, it is to be understood that multiple adjustments may be made when the adjustment threshold is reached if invalid event signals are occurring at least a threshold number of times during different portions of the R-wave sensing threshold profile, warranting adjustments to two or more R-wave sensing control parameters (e.g., at two or more of blocks 762, 770, 772, 776 and/or 778). Accordingly, after making an adjustment at block 762, control circuit 80 may advance to block 764 to determine if invalid event signals occurred during the second drop time interval. After making an adjustment at block 770 or 772, control circuit 80 may advance to block 774 to determine if invalid event signals occurred while the R-wave sensing threshold was at the sensing floor, which may be after the second drop time interval expires but could be earlier in the ventricular cycle depending on the starting R-wave sensing threshold amplitude.

It is to be understood that some or all adjustments to R-wave sensing control parameters may be made without determining a maximum peak amplitude of the sensed signal or determining metrics of the in-channel sensed event time. In other examples, an R-wave sensing control parameter may be incremented by a predetermined step increase in response to one or more invalid event signals. For instance, control circuit 80 may increase the sensitivity setting to increase the minimum amplitude of the R-wave sensing threshold in response to invalid event signals occurring during the sensing floor without requiring a determination of a metric of the maximum amplitude of the sensed signals. When invalid event signals occur during the second drop time interval, the second threshold amplitude may be increased by increasing the percentage used to set the second threshold amplitude by a predetermined increment, e.g., 3%, 5%, 10% or other increment, without determining a metric of the maximum amplitudes of the sensed signals. One or more R-wave sensing control parameters, used for setting an R-wave sensing threshold amplitude and/or the drop time at which the R-wave sensing threshold amplitude changes, may by increased by a predetermined increment until the number of invalid senses no longer reaches the adjustment threshold (at block 758) or until a maximum limit of a given R-wave sensing control parameter is reached, or a maximum number of adjustments allowed is reached.

In addition or alternatively to adjusting the R-wave sensing threshold parameters when a threshold number or threshold frequency of invalid event signals are identified, control circuit 80 may be configured to adjust R-wave sensing control parameters when a threshold number, frequency, percentage or ratio of sensed event signals are identified as valid event signals. For instance, when 100% (or other relatively high percentage) of ventricular sensed event signals from a given sensing channel 83 or 85 are identified as valid event signals over a predetermined time interval or total number of sensed event signals, settings used to control the R-wave sensing threshold amplitude may be higher than needed and/or the first and/or second drop time intervals may be longer than needed for reliable R-wave sensing. In some cases, relatively lower amplitude R-waves may be undersensed. If R-wave undersensing occurs and the heart rate slows, therapy delivery circuit 84 may deliver pacing pulses when pacing is not actually needed.

As such, at block 780, control circuit 80 may optionally log valid event signal data. Valid event signal data may include a count of valid event signals, the cardiac electrical signal maximum amplitude associated with valid event signals, the maximum amplitude time, and/or the in-channel sensed event interval (the R-wave sensing threshold crossing time). In some examples, control circuit 80 may log valid event signal data after a threshold number or percentage of valid event signals is reached. For example, when 100% of sensed event signals received from a given sensing channel are valid over the most recent one minute, one hour or other threshold time interval, control circuit 80 may determine that an adjustment threshold is reached (block 782) and subsequently determine valid event signal data for a sample of valid event signals, e.g., 3, 5, 8, 12 or other selected number of valid event signals. In this way, control circuit 80 may not determine valid event signal data for each valid event signal as it is received but only when needed for making an R-wave sensing control parameter adjustment to conserve processing power and time.

When an adjustment threshold based on the frequency or count of valid event signals is reached at block 782, control circuit 80 may adjust one or more R-wave sensing control parameters at block 784. When the valid event signals are received from one sensing channel 83 or 85 and are validated based on morphology analysis, control circuit 80 may adjust the R-wave sensing control parameter(s) for that sensing channel. One or more of the starting sensing threshold, second sensing threshold, sensitivity setting, first drop time interval and/or second drop time interval may be decreased at block 784. When control circuit 80 has determined and logged valid sensed event data at block 780, control circuit 80 may evaluate the logged data for determining a sensing control parameter adjustment. For example, a metric of the maximum peak amplitude and/or a metric of the timing during the ventricular cycle may be determined and used to select which sensing control parameter(s) are adjusted and/or by how much.

For example, if all or most valid sensed event signals are sensed after the expiration of the second drop time interval, the sensitivity setting may be decreased. If all or most valid sensed event signals are sensed during the second drop time interval, the second sensing threshold amplitude may be decreased. The R-wave sensing control parameter(s) may be adjusted to a lower value, so that the sensing channel is more sensitive to sensing cardiac electrical signals. R-waves are reliably being sensed based on the valid event signals enabling reliable bradycardia pacing control. However, a lower R-wave sensing threshold amplitude may improve R-wave sensing or fibrillation wave sensing when ventricular tachyarrhythmias occur while maintaining reliable R-wave sensing.

In various examples, control circuit 80 may determine the timing but not the cardiac electrical signal amplitude associated with ventricular sensed event signals determined to be valid event signals for use in determining an adjustment to the sensing threshold amplitude or drop time interval, or control circuit 80 may determine the maximum peak amplitude without determining or using timing data relating to the valid event signals for determining an adjustment to the sensing threshold amplitude and/or drop time intervals. In still other examples, control circuit 80 may not determine any timing or amplitude data relating to the ventricular sensed event signal determined as a valid event signals at block 780. Control circuit 80 may adjust the R-wave sensing control parameters in response to an adjustment threshold being reached at block 782 by decrementing a sensing threshold amplitude (e.g., the sensitivity and/or the percentage(s) of the maximum peak amplitude used to set the starting and/or second sensing threshold amplitudes).

Control circuit 80 may additionally or alternatively adjust the R-wave sensing control parameters at block 784 in response to an adjustment threshold being reached at block 782 by decrementing the first and/or second drop time intervals by a predetermined interval, e.g., 20, 40 or 60 ms. The adjustments may be made to the R-wave sensing control parameter(s) until the adjustment threshold is no longer reached, a minimum limit of a given R-wave sensing control parameter is reached, or a maximum number of adjustments allowed is reached.

Figure 15:
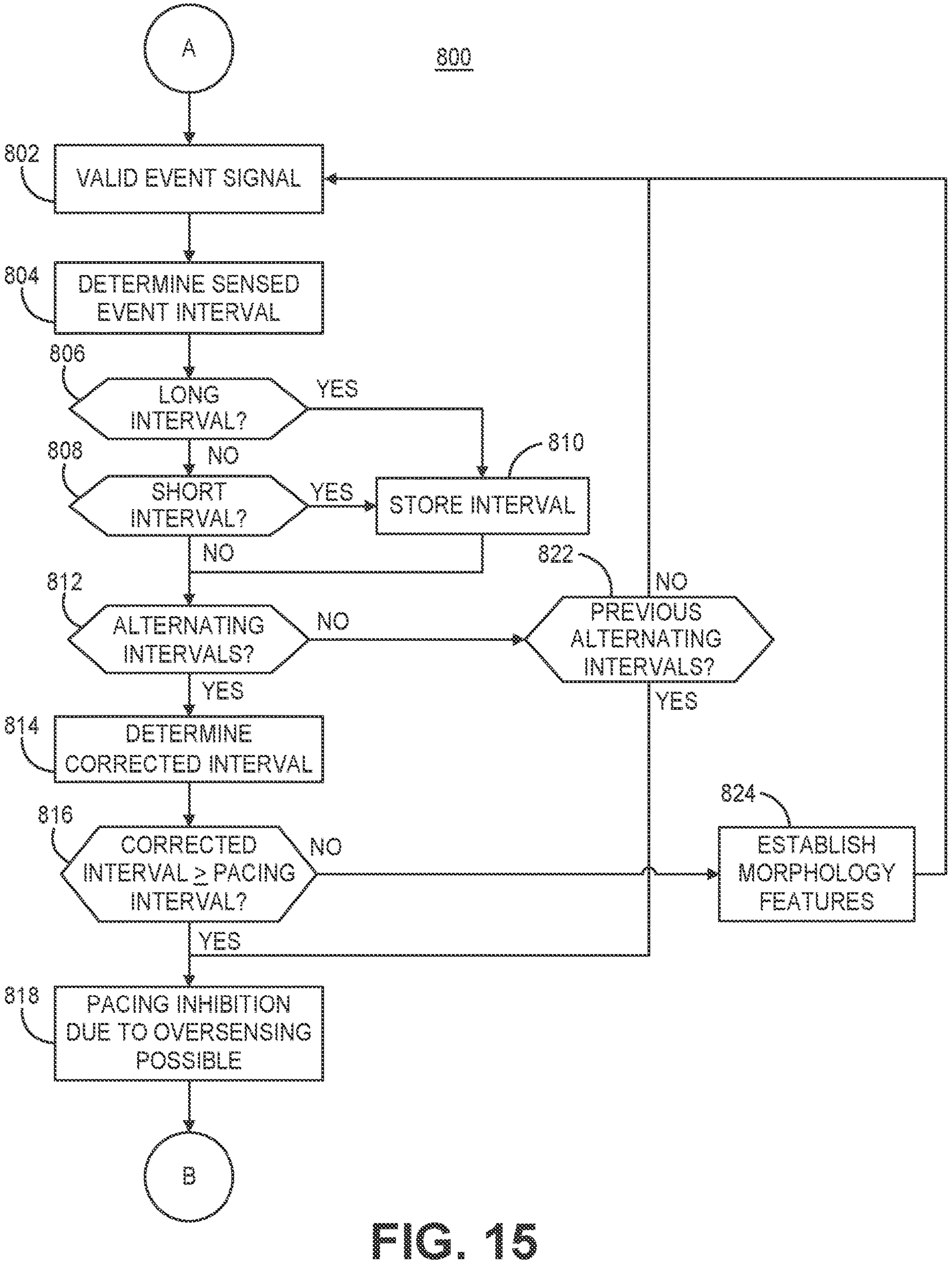
FIG. 15 is a flow chart of a method for establishing morphology features of cardiac electrical signals for use in validating sensed cardiac event signals and controlling cardiac pacing according to another example.

FIG. 15 is a flow chart 800 of a method for establishing morphology features of cardiac electrical signals for use in validating sensed cardiac event signals and controlling cardiac pacing according to another example. In some instances, a P-wave, T-wave or noise may be oversensed by both sensing channels 83 and 85 resulting in a false valid event signal determination. A false valid event signal determination could result in inhibiting a pacing pulse when a pacing pulse is actually needed, e.g., when the true ventricular rate is less than the hysteresis pacing rate or the lower pacing rate. In other instances, a P-wave or T-wave may be oversensed by one sensing channel 83 or 85 and the ECG signal segment from the morphology signal channel 87 may meet the R-wave criteria resulting in a false valid event signal. While such instances would likely be rare, pacing inhibition for more than one or two hysteresis pacing intervals may cause symptoms in some patients. As such, in some examples, control circuit 80 may be configured to determine when P-wave and/or T-wave oversensing is suspected and perform cardiac electrical signal morphology analysis to establish morphology criteria that discriminate between R-waves, P-waves and/or T-waves and use the established morphology criteria for validating ventricular sensed event signals, at least when oversensing is suspected.

At block 802, control circuit 80 identifies a valid event signal. The valid event signal may be validated based on a ventricular sensed event signal received from each of the two sensing channels 83 and 85 within the validation window from each other. At other times, the valid event signal may be validated based on a single ventricular sensed event signal received from one sensing channel 83 or 85 and the R-wave criteria being met based on morphology analysis of the buffered ECG signal segment. A valid event signal may be determined using any of the techniques described herein.

At block 804, control circuit 80 determines the sensed event interval from the most recent preceding ventricular event, e.g., a delivered pacing pulse or a valid sensed event time, to the sensed event time determined for the current valid event signal. In some examples, the process of flow chart 800 determines sensed event intervals that begin and end with a valid ventricular sensed event signal and excludes sensed event intervals that begin with a pacing pulse and end with a valid ventricular sensed event signal. Techniques for determining the sensed event time of a valid event signal that can be used for determining the sensed event interval at block 804 are described above (e.g., the time of the first, earliest ventricular event signal, the midpoint between the first, earliest and the second, later ventricular event signal, etc.).

Control circuit 80 may compare the sensed event interval to a long interval threshold at block 806. The long interval threshold may be set to a predetermined interval, e.g., at least 400 ms, at least 500 ms, or at least 600 ms in various examples. The long interval threshold may be set based on one or more preceding sensed event intervals. For instance, the long interval threshold may be set equal to the most recent preceding sensed event interval that begins and ends with a validated ventricular sensed event signal. In other examples, the long interval threshold may be set to the most recent preceding sensed event interval plus an offset, e.g., plus 100 ms, plus 200 ms or other offset, or as a percentage of the most recent preceding sensed event interval, e.g., 120%, 125%, 130% or other selected percentage. In some examples, more than one threshold or other criteria may be applied at block 806 by control circuit 80 for identifying a long interval. For instance, control circuit 80 may compare the sensed event interval to a predetermined threshold, e.g., 400 ms, and the most recent preceding valid sensed event interval. When the current valid sensed event interval is consecutive with and greater than the most recent preceding valid sensed event interval and greater than 400 ms, the current valid sensed event interval is identified as a long interval at block 806.

When a long interval is identified, control circuit 80 may store the sensed event interval in a long interval buffer and/or an alternating interval buffer in memory 82 at block 810. Control circuit 80 may store additional information regarding the current valid sensed event such as morphology feature values that may have been determined to validate the sensed event signal and/or an associated ECG signal segment received from the morphology signal channel 87 and/or from the sensing channel(s) 83 and/or 85 that produced the sensed event signal(s) determined to be valid.

When the valid sensed event interval is not identified as a long interval, control circuit 80 may determine if short interval criteria are met at block 808. Control circuit 80 may compare the valid sensed event interval to one or more thresholds or criteria for determining a short interval. For example, when the current sensed event interval is consecutive with and less than the most recent preceding valid sensed event interval and less than or equal to a predetermined threshold interval, e.g., 400 ms, the valid sensed event interval may be identified as a short interval at block 808. When a short interval is identified, control circuit 80 may store the interval in a buffer in memory 82 at block 810 and may store additional data relating to the short interval, such as determined morphology features and/or ECG signal segment(s) as generally described above.

At block 812, control circuit 80 may determine if alternating intervals are detected. Control circuit 80 may detect alternating intervals based on at least one sequence of short-long intervals or long-short intervals. Control circuit 80 may detect alternating intervals based on at least one, two or other threshold number of pairs of short-long and/or long-short intervals out of a predetermined number of most recent sensed event intervals. In various examples, alternating intervals may be detected by control circuit 80 based on a threshold number of alternating pairs (short-long or long-short) or alternating triplets (long-short-long or short-long-short) of valid sensed event intervals out of a predetermined number, e.g., up to 20 or more, most recent sensed event intervals. In one example, control circuit 80 detects alternating intervals in response to at least 12 out of 16 most recent sensed event intervals being in an alternating pair including one long and one short interval.

In response to detecting alternating intervals, control circuit 80 may evaluate stored morphology features and/or ECG signal segments corresponding to the valid sensed event signals ending the short intervals and/or the long intervals for establishing morphology features (at block 824) for discriminating oversensed P-waves and/or T-waves from true R-waves. In some examples, before determining morphology features for establishing P-wave and/or T-wave morphology criteria at block 824, control circuit 80 may determine a corrected sensed event interval at block 814. Control circuit 80 may sum pairs of long and short intervals to determine corrected sensed event intervals assuming that for each pair of one long and one short interval, one event is oversensed. Control circuit 80 may determine a mean, median, or longest corrected interval as a metric of the corrected intervals in various examples. In another example, control circuit 80 may determine a mean, median, longest, or trimmed mean of the short intervals stored at block 810 and a mean, median, longest or trimmed mean of the long intervals stored at block 810. Control circuit 80 may sum the metric of short intervals and the metric of long intervals to determine a representative corrected sensed event interval at block 814.

At block 816, control circuit 80 may compare the corrected interval to the current pacing escape interval, e.g., the hysteresis interval or an LRI. In other examples, individual corrected intervals representing the sum of one pair of long and short intervals may be individually compared to the current pacing interval at block 816. Control circuit 80 may determine if the representative corrected interval, or if a threshold number of individual corrected intervals, are greater than or equal to the current pacing interval. If the representative corrected interval is greater than or equal to the current pacing escape interval ("yes" branch of block 816), control circuit 80 may determine that pacing may be inhibited due to suspected oversensing. When suspected pacing inhibition due to oversensing is determined at block 818, control circuit 80 may advance (as indicated by connector "B") to the process of flow chart 870 in FIG. 20 as described below for validating ventricular sensed event signals and controlling pacing pulses during suspected oversensing.

Referring again to block 816, when the corrected interval(s) determined at block 814 are less than the current pacing interval ("no" branch of block 816), the true ventricular rate is likely faster than the rate associated with the current pacing interval such that even if oversensing is occurring, cardiac pacing is not imminently needed. Control circuit 80 may advance to block 824 to establish morphology features for discriminating likely oversensed P-waves and/or T-waves from R-waves. Methods for establishing morphology features at block 824 for discriminating P-waves and T-waves from myocardial depolarizations are described below in conjunction with FIG. 19.

In some cases, P-wave oversensing may occur for a run of sensed event intervals causing possible inhibition of pacing. True atrioventricular conduction block (AV block) may occur during an episode of P-wave oversensing such that R-waves are no longer present to be sensed. Oversensed P-waves may continue to be falsely validated as ventricular sensed events causing pacing inhibition during AV block. This condition is illustrated in FIG. 16.

Figure 16:
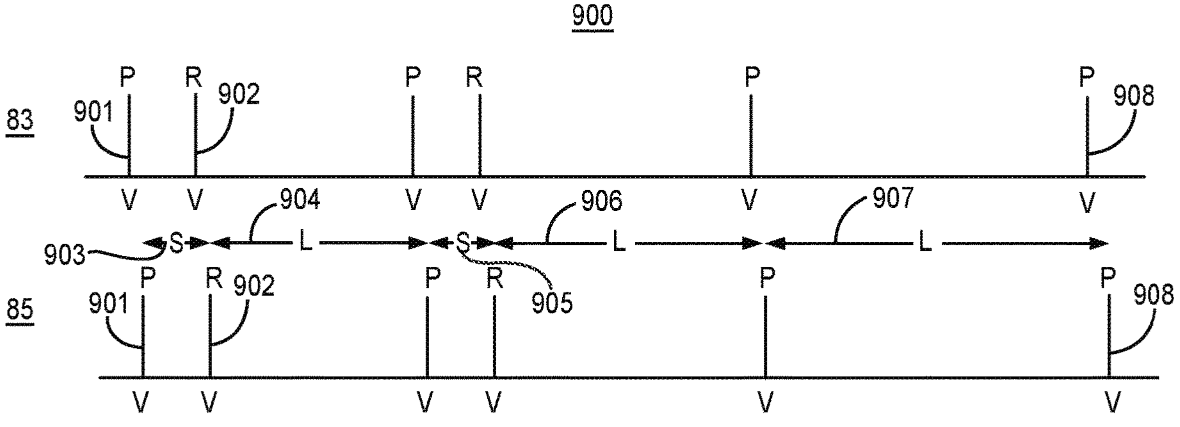
FIG. 16 is a conceptual diagram of ventricular sensed event signals that may be validated during P-wave oversensing.

FIG. 16 is a conceptual diagram 900 of ventricular sensed event signals (V) that may be validated by control circuit 80 during P-wave oversensing by both sensing channels 83 and 85. Ventricular sensed event signals produced by the first sensing channel 83 are shown along the top timeline and ventricular sensed event signals produced by the second sensing channel 85 are shown along the bottom timeline. Each ventricular sensed event signal is labeled "V" and labeled either a "P" indicating when the sensed signal is a true P-wave or an "R" when the sensed signal is a true R-wave. In this example, P-waves are oversensed by both sensing channels 83 and 85.

When ventricular sensed event signals 901 are produced by both channels 83 and 85 within a validation window, the sensed event signals 901 corresponding to true P-waves are falsely identified as valid event signals. A sensed event interval 903 is determined from the midpoint of the time between the two sensed event signals 901, determined as the valid sensed event time by control circuit 80, to the next valid sensed event time. The next valid sensed event time is the midpoint between the two ventricular sensed event signals 902 corresponding to true R-waves, which occur within a validation window of each other. The sensed event interval 903 may be identified as a short interval (labeled "S") by control circuit 80 according to criteria described above in conjunction with FIG. 15. The next sensed event interval 904 extending from the sensed event time corresponding to true R-waves sensed by both sensing channels 83 and 85 to true P-waves that are oversensed by both sensing channels 83 and 85 may be identified as a long, sensed event interval 904 (labeled "L"). The long sensed event interval 904 is followed by another short sensed event interval 905 due to oversensing of P-waves on both sensing channels followed by sensing of true R-waves on both channels. The next sensed event interval 906 is a long interval between a true R-wave and the next oversensed P-wave. Oversensed P-waves end the long intervals 904 and 906, and R-waves end the short intervals 903 and 905 in this situation.

This alternation of long and short intervals 903, 904, 905 and 906 between valid event signals may be detected by control circuit 80 as alternating intervals, e.g., as described above in conjunction with block 812 of FIG. 15. As described above, the sum of the short and long intervals may be determined as a corrected interval and compared to the pacing escape interval. If the sum of the short and long intervals is less than the pacing escape interval, pacing is unlikely to be needed. Control circuit 80 may analyze the ECG signal segments stored in association with valid event signals that occur at long intervals for establishing P-wave morphology criteria. When the sum of the short and long intervals is close to or longer than the pacing escape interval, pacing may be needed. Previously established P-wave morphology criteria may be used to identify ventricular sensed event signals that are likely to be P-wave oversensing, e.g., as described below in conjunction with FIG. 20.

When AV block occurs during P-wave oversensing, the true R-waves disappear and the P-waves may continue to be oversensed as shown in FIG. 16. Subsequent sensed event intervals 906 and 907 are long intervals occurring between a true R-wave and oversensed P-wave and two consecutive oversensed P-waves, respectively. If the sensed event interval 907 is less than the pacing escape interval, a pacing pulse is withheld by therapy delivery circuit 84 due to the sensed event signals 908 being falsely validated when P-waves are oversensed on both sensing channels 83 and 85 within the validation window. In other examples, a single P-wave oversensed on one channel may be validated based on morphology analysis of the stored ECG signal segment. This could occur if values of morphology signal features of relatively large P-waves overlap with values of morphology signal features of relatively small R-waves, for example.

Referring again to FIG. 15, in order to avoid pacing inhibition due to P-wave oversensing during AV block, as generally depicted in FIG. 16, control circuit 80 may be configured to detect a change from alternating intervals to non-alternating intervals at block 822. Control circuit 80 may determine that alternating interval criteria is not met at block 812 but that alternating intervals were detected in a preceding group of sensed event intervals. For example, when 12 out of 16 sensed event intervals are identified as belonging to a pair of alternating intervals and this criteria for detecting alternating intervals is no longer satisfied, dropping out of true R-waves due to AV block with oversensing of P-waves may be present. When alternating interval criteria are no longer satisfied after being previously satisfied, control circuit 80 may detect previous alternating intervals followed by non-alternating intervals at block 822. In some examples, a threshold number of non-alternating intervals, e.g., 2, 3, 4, 6, 8, 10 or 12 non-alternating intervals following a determination of alternating intervals based on the criteria described above in conjunction with block 812 may be detected by control circuit 80 as a change from alternating intervals to non-alternating intervals at block 822.

Additionally or alternatively, a change from alternating to non-alternating intervals may be determined at block 822 based on at least one or a series, e.g., two or more, sensed event intervals being approximately equal to (or within a threshold range of) a corrected interval of the previous alternating intervals. Control circuit 80 may determine a mean, median or most recent corrected interval from the alternating intervals as a representative corrected interval. Control circuit 80 may compare a current sensed event interval to the representative corrected interval to identify sensed event intervals that may represent a change from alternating intervals to non-alternating intervals. When the current sensed event interval is within a threshold range, e.g., within 100 ms, 50 ms, 30 ms, or other selected threshold range, of the representative corrected interval, control circuit 80 may count the current sensed event interval as a non-alternating interval. When a threshold number of non-alternating intervals are counted after detecting alternating intervals, control circuit 80 may detect a change from alternating to non-alternating intervals at block 822.

If alternating intervals are not detected at block 812 and a change from previously alternating to non-alternating intervals is not detected at block 822, control circuit 80 returns to block 802 to wait for the next valid event signal. In response to detecting a change from alternating to non-alternating intervals, however, control circuit 80 may determine possible pacing inhibition due to oversensing (e.g., oversensing of P-waves during AV block) at block 818. Control circuit 80 may advance to the flow chart 870 of FIG. 20 (as indicated by connector "B").

Figure 17:
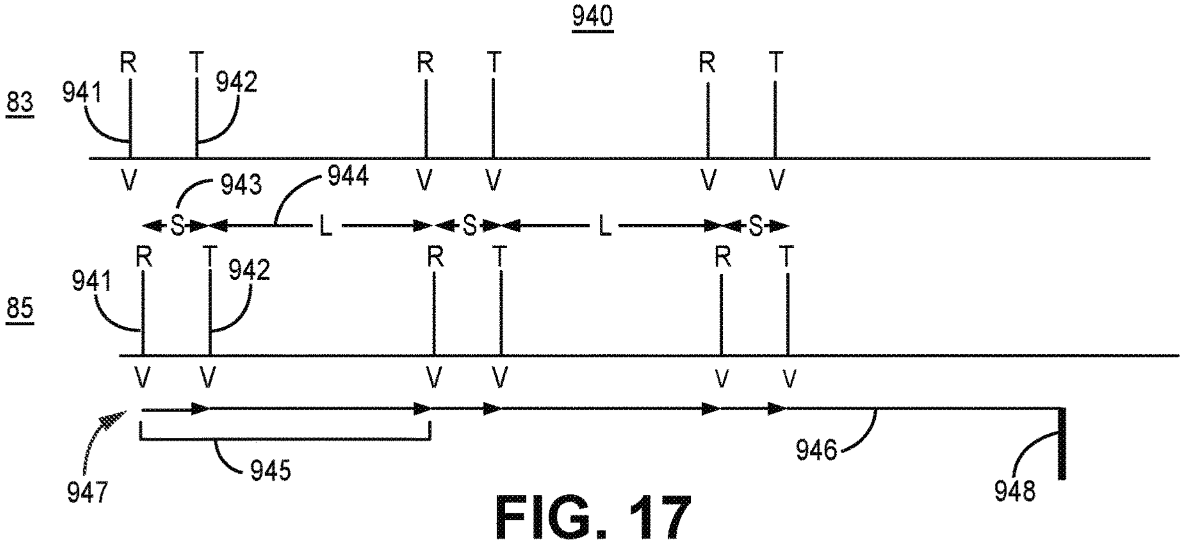
FIG. 17 is a conceptual diagram of ventricular sensed event signals that may be validated during T-wave oversensing.

FIG. 17 is a conceptual diagram 940 of ventricular sensed event signals (V) that may be validated during T-wave oversensing by both sensing channels 83 and 85. Ventricular sensed event signals produced by the first sensing channel 83 are shown along the top timeline and ventricular sensed event signals produced by the second sensing channel 85 are shown along the bottom timeline. Each ventricular sensed event signal is labeled "V" and with either a "T" indicating when the sensed signal is a true T-wave or an "R" indicating when the sensed signal is a true R-wave. When ventricular sensed event signals 941 are produced by both channels 83 and 85 within a validation window, control circuit 80 determines a valid event signal associated with the true R-wave. When ventricular sensed event signals 942 occur within the validation window of each other, the ventricular sensed event signals 942 corresponding to a true T-wave are identified as a false valid event signal. A sensed event interval 943 may be determined using the techniques disclosed herein and may be identified as a short interval (labeled "S") by control circuit 80. In this case, the short interval begins with a true R-wave and ends with a true T-wave.

The next sensed event interval 944 extending from the sensed event time corresponding to the true T-wave oversensed by both sensing channels 83 and 85 to a true R-wave properly sensed by both sensing channels 83 and 85 may be identified as a long sensed event interval 944 (labeled "L"). In this situation, the S-L alternating pattern may continue as long as T-waves are oversensed. Pacing escape intervals 947 are restarted by control circuit 80 in response to each valid event signal. If AV block occurs during the T-wave oversensing, however, both R-waves and T-waves disappear and are not sensed such that a pacing escape interval 946 expires and a pacing pulse 948 is delivered. Alternating S-L intervals having a corrected interval 945 near or longer than the pacing escape interval 946 may lead to pacing inhibition due to T-wave oversensing. By establishing T-wave morphology features from ECG signal segments stored when alternating intervals having a corrected interval that is shorter than the pacing escape interval, e.g., the pacing escape interval less an offset, control circuit 80 may use the T-wave morphology features in validating ventricular sensed event signals to avoid restarting a pacing escape interval and inhibiting pacing due to T-wave oversensing.

Figure 18:
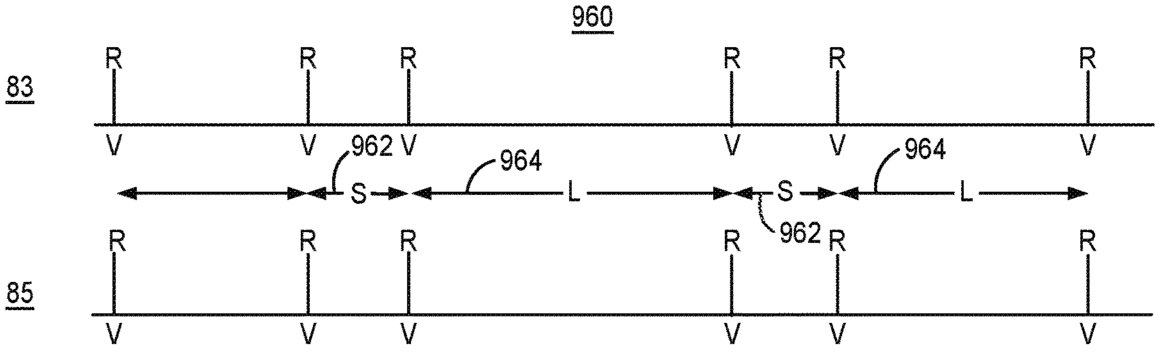
FIG. 18 is a conceptual diagram of ventricular sensed event signals that may be validated during bigeminy.

FIG. 18 is a conceptual diagram 960 of ventricular sensed event signals (V) that may be validated by control circuit 80 during bigeminy. Ventricular sensed event signals produced by the first sensing channel 83 are shown along the top timeline, and ventricular sensed event signals produced by the second sensing channel 85 are shown along the bottom timeline. Each ventricular sensed event signal is labeled "V" and labeled "R" indicating that the sensed signal is a true R-wave. In this example, bigeminy occurs with ectopic beats occurring at short coupling intervals 962 from a normal R-wave and followed by long pauses 964. Each ectopic beat is properly sensed as an R-wave resulting in a valid event signal in the example. When bigeminy occurs, control circuit 80 may detect alternating short and long intervals, but, in this case of alternating intervals, inhibition of pacing pulses is appropriate. The associated ventricular sensed event signals may be properly generated by one or both sensing circuits 83 and 85 and determined as valid event signals by control circuit 80. When an ectopic beat occurs at a short interval 962, the pacing escape interval (not shown in FIG. 18) can be restarted to appropriately inhibit a pacing pulse.

The ECG signal segments that are stored in association with the ventricular sensed event signals during bigeminy may be used to establish ectopic beat criteria that can be used by control circuit 80 when a ventricular sensed event signal is received at a short interval. This ectopic beat criteria may increase the likelihood of properly validating a ventricular sensed event signal that occurs at a short interval due to a PVC, bigeminy, aberrantly conducted ventricular depolarization or other ectopic beat for the purposes of restarting a pacing escape interval. By establishing ectopic beat criteria corresponding to an abnormal R-wave morphology that may be recurring in a given patient, the performance of control circuit 80 in validating ventricular sensed event signals and controlling pacing pulses may be improved.

Figure 19:
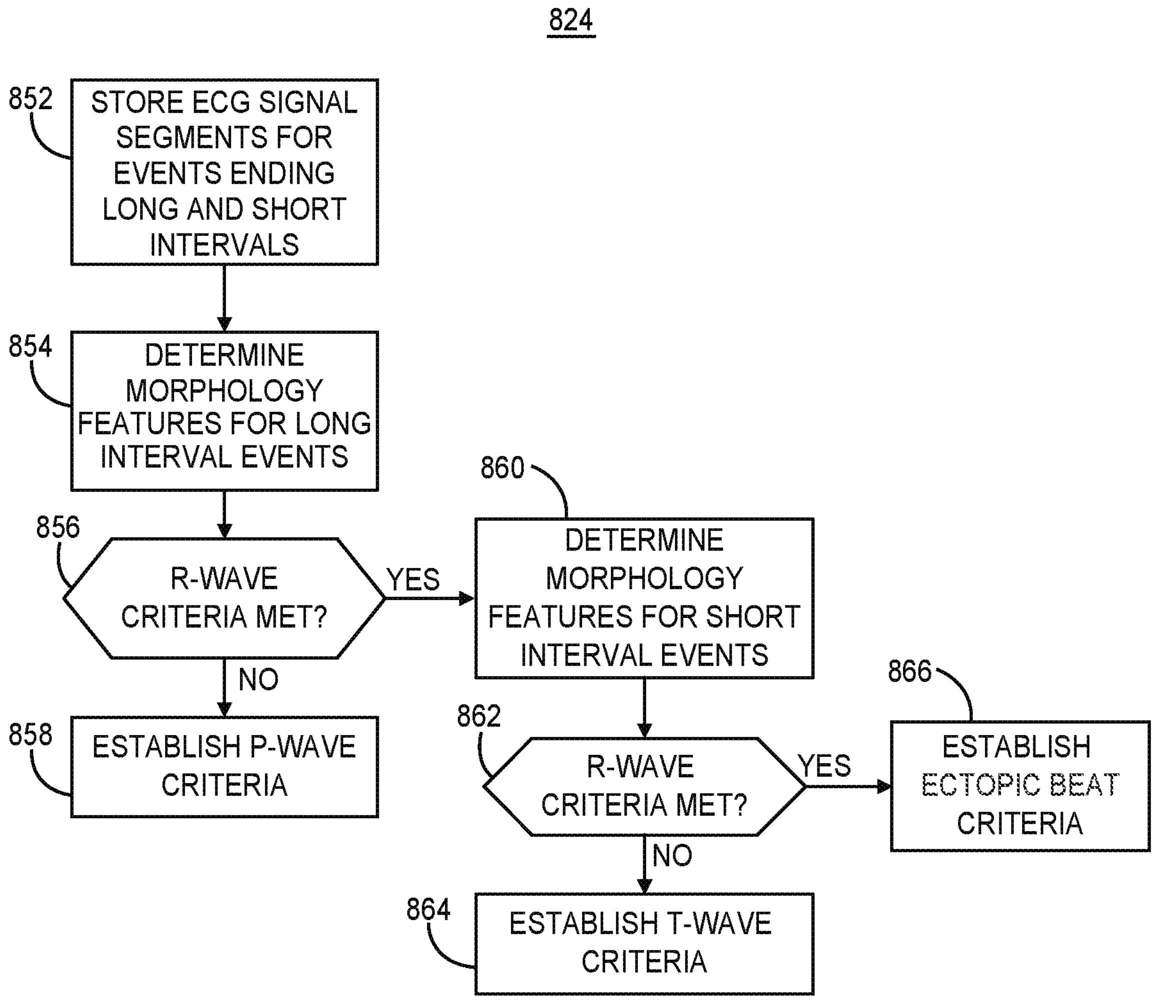
FIG. 19 is a flow chart of a method for determining morphology features of cardiac electrical signals received during alternating sensed event intervals according to one example.

FIG. 19 is a flow chart 824 of a method for determining morphology features of cardiac electrical signals received during alternating intervals according to one example. The process of flow chart 824 may be performed at identically numbered block 824 of FIG. 15 when alternating event intervals are detected. The process may be performed when the alternating event intervals have a corrected interval that is less than, or at least an offset less than, the pacing escape interval in some examples. Oversensed P-waves or T-waves may be falsely validated by control circuit 80 resulting in alternating sensed event intervals that are detected at block 812 of FIG. 15 as described above. The oversensed P-waves and/or T-waves may be validated based on a second sensed event signal within a validation window and/or morphology analysis of the ECG signal segment stored in response to the first, earliest ventricular sensed event signal (and/or the second, later ventricular sensed event signal). In other instances, as described in conjunction with FIG. 18, the valid event signals at alternating intervals may correspond to bigeminy.

At block 852, control circuit 80 stores ECG signal segments associated with valid event signals ending at least one long interval and at least one short interval of the identified alternating intervals. In some examples, the ECG signal segment is stored only in response to the first, earliest ventricular event signal. When alternating intervals are detected and the first, earliest ventricular event signal is validated based on a second, later ventricular event signal, the ECG signal segment may be retained in memory to enable determination of morphology features for establishing criteria for discriminating between P-waves, T-waves and/or ectopic beats. In other examples, a second ECG signal segment may be stored in response to a second sensed event signal received within a validation window. The process of flow chart 824 may be performed using one or both ECG signal segments when two ECG signal segments are stored for each valid event signal. For the sake of illustration, flow chart 824 is described as storing and analyzing the ECG signal segment stored for the first ventricular sensed event signal (which may be the only sensed event signal within a validation window in some instances).

Memory 82 may be configured to save a predetermined number of ECG signal segments to be available for analysis when control circuit 80 detects alternating sensed event intervals. Accordingly, control circuit 80 may store ECG signal segments in memory 82 corresponding to multiple validated sensed event signals. Each ECG signal segment may be labeled or flagged as being an ECG signal segment associated with a validated sensed event signal that ends a long sensed event interval or associated with a validated sensed event signal that ends a short, sensed event interval. Separate memory buffers may be allocated to storing ECG signal segments ending long sensed event intervals and ECG signal segments ending short, sensed event intervals. In various examples, one or more ECG signal segments, e.g., two to twelve ECG signal segments, may be stored in memory 82 for long sensed event intervals and for short, sensed event intervals for establishing morphology criteria for discriminating oversensed P-waves and/or T-waves from true R-waves and/or reliably validating ectopic beats as R-waves.

At block 854, control circuit 80 may determine ECG signal morphology features from the ECG signal segments ending the long sensed event intervals. Control circuit 854 may determine ensemble averaged ECG signal segments from the segments stored in association with the long intervals to obtain one ECG signal segment representative of the morphology associated with the long intervals. Morphology features may be determined from the representative ECG signal segment. In other examples, morphology features may be determined from each signal segment stored in association with a long interval and a representative value of a given feature, e.g., a mean, median, trimmed mean or median, or range may be determined from the features determined from each segment as the representative morphology feature value of the ECG signal segments associated with the long intervals. The morphology features determined at block 854 may include, but are not limited to, a morphology template, wavelet transform coefficients, a maximum peak amplitude, a maximum slope, time of the maximum slope, time of the maximum peak, slope difference, signal width, peak polarity, number of peaks, polarity pattern (e.g., positive peak followed by negative peak or vice versa), number of zero crossings, and time interval between maximum and/or minimum peaks, as examples.

At block 856, control circuit 80 may determine if R-wave criteria are met for confirming that the valid event signals occurring at long intervals are true R-waves. When alternating intervals include oversensed P-waves, the R-waves occur at the short intervals, and the oversensed P-waves occur at the long intervals, as generally shown in FIG. 16. When alternating intervals include oversensed T-waves, the oversensed T-waves occur at short intervals following the true R-waves, and the R-waves occur at the long intervals, as generally shown in FIG. 17. In some cases, bigeminy may occur with short intervals followed by long pauses in which case R-waves occur at both short and long intervals, as generally shown in FIG. 18. Control circuit 80 may analyze the morphology features determined at block 854 and may analyze short and long interval durations and/or their differences in order to determine if the ECG signal segments stored for long intervals are likely to correspond to oversensed P-waves or true R-waves.

For instance, the morphology template for the ECG signal segments associated with long intervals may be compared to a previously established R-wave template to determine a morphology matching score. When the matching score is greater than a confident R-wave threshold, e.g., greater than 55, 60, 65, 70, 75 or other selected threshold (out of a possible matching score of 100), control circuit 80 may confirm that the long event intervals are R-waves. One or more morphology features determined at block 854 may be compared to previously established thresholds or criteria for confirming R-wave morphology with a high degree of confidence, such as a maximum amplitude threshold, peak-to-peak amplitude of the difference signal, signal width, or other examples listed herein.

Additionally or alternatively, control circuit 80 may compare the short and long intervals to criteria for identifying a likely pattern of P-R-P-R sensing. Each individual long interval and/or short interval may be compared to each other and/or respective threshold ranges for determining if the alternating pattern is likely to represent a P-R sensing pattern. Alternatively or additionally, a mean, median, trimmed mean or other metric of the long intervals and/or the short intervals may be compared to respective threshold ranges and/or to each other. For example, a P-R interval may be expected to be in the range of 100 to 250 ms. In some patients having AV conduction delay, the P-R interval may be longer, e.g., up to 350 ms. The short intervals may be compared to an expected P-R interval range and/or to an expected R-T interval range. The R-T interval may generally be 350 ms to 600 ms and may vary between patients. When control circuit 80 determines that the short interval falls into an expected P-R interval range, control circuit 80 may determine that the R-wave criteria are met at block 856. True R-waves are likely being sensed at the short intervals such that the long intervals are likely ending with oversensed P-waves. In this case, the morphology features determined at block 854 for ECG signal segments stored in association with the long intervals likely correspond to oversensed P-waves.

In response to R-wave criteria not being met at block 856, therefore, control circuit 80 may establish P-wave morphology criteria at block 858 based on the morphology features determined at block 854 for the valid event signals ending the long event intervals. In one example, if the morphology matching score between the morphology template determined at block 854 and a previously established R-wave morphology template is less than a threshold matching score and the short interval metric is within a P-R interval threshold range, control circuit 80 establishes P-wave morphology criteria at block 858 based on the morphology features determined at block 854. P-wave morphology criteria may include one or more thresholds, ranges or other values determined based on the morphology features determined at block 854. In one example, a peak amplitude range (which may be a peak rectified amplitude or absolute value) is determined as a P-wave morphology criterion based on the maximum peak amplitudes of the ECG signal segments stored in association with the long intervals. Additionally or alternatively, a range of the slope difference (e.g., the peak to peak amplitude of the first order difference signal) may be determined as a P-wave morphology criteria determined from the long interval ECG signal segments. Control circuit 80 may establish a P-wave morphology template for determining a morphology matching score using wavelet transform or other analysis. The P-wave morphology template may be compared to ECG signal segments for identifying P-waves during validation processes. Alternatively, a morphology matching score between the P-wave morphology template and the previously established R-wave morphology template may be determined to establish a confident R-wave matching score threshold and/or a confident P-wave morphology matching score range for discriminating between P-waves and R-waves.

It is recognized that numerous morphology feature thresholds, ranges or other criteria may be established at block 858 based on the morphology features determined at block 854. Control circuit 80 may verify that the criteria established at block 858 do not overlap with R-wave morphology criteria. For example, control circuit 80 may determine that the maximum rectified amplitude range established for P-wave morphology criteria at block 858 overlaps with the peak amplitude threshold of R-wave criteria used by control circuit 80 to validate sensed event signals. In this case, control circuit 80 may adjust the maximum amplitude range for P-wave criteria and/or the peak amplitude threshold for the R-wave criteria so that the maximum rectified amplitude range for P-waves does not overlap (include) the maximum amplitude threshold of the R-wave criteria. When overlapping P-wave and R-wave morphology criteria are identified for a given morphology feature and cannot be separated or discriminated from each other, control circuit 80 may select a different morphology feature for establishing a P-wave morphology criterion that does not overlap with and is distinct from R-wave morphology criteria that is used by control circuit 80 for validating sensed event signals.

Returning to block 856, when R-wave criteria are met, which may include determining that the short intervals fall within an R-T interval range indicating that R-waves are likely ending the long intervals in the alternating interval pattern, control circuit 80 advances to block 860 to determine morphology features of the ECG signal segments stored in association with the short intervals. Any of the example morphology features listed herein may be determined at block 860 from the ECG signal segments. In this case, T-waves or ectopic beats may be occurring at the short intervals. In order to determine if the morphology features associated with events sensed at short intervals should be used to establish T-wave oversensing criteria, control circuit 80 may determine if R-wave criteria are met at block 862, which could indicate that ectopic beats rather than T-waves are occurring at the short intervals.

Control circuit 80 may determine if R-wave criteria are met at block 862 based on an analysis of the short and/or long interval durations and/or by comparing morphology features determined at block 860 for the short interval events to R-wave morphology criteria. For example, control circuit 80 may determine that R-wave criteria are met when the short intervals (or a metric thereof) do not fall within an R-T interval threshold range and/or a morphology matching score between a morphology template determined at block 860 for events ending the short intervals and a previously established R-wave morphology template is greater than an R-wave matching score threshold. When R-wave criteria are not met by the morphology features determined for events ending short intervals at block 862, control circuit 80 may establish T-wave morphology criteria at block 864 based on the morphology features determined at block 860 for the ECG signal segments stored in association with short intervals. The T-wave morphology criteria may include one or more thresholds, ranges or other values set based on the morphology features determined at block 860.

Control circuit 80 may establish a T-wave morphology template for determining morphology matching scores using wavelet transform or other analysis. The T-wave morphology template may be established for positively identifying oversensed T-waves ending short intervals or for establishing a confident R-wave morphology matching score threshold based on a matching score between the T-wave morphology template and the previously established R-wave morphology template. T-wave morphology criteria may include a maximum rectified amplitude threshold range, a threshold range of the slope difference, signal width threshold, maximum slope threshold range, maximum slope timing range, or other criteria based on any of the example morphology features listed herein. As described above with regard to establishing P-wave morphology criteria, control circuit 80 may determine if T-wave morphology criteria overlaps or includes R-wave morphology criteria. If so, control circuit 80 may adjust the T-wave and/or R-wave morphology criteria or change which morphology features are used for establishing the T-wave morphology criteria. Control circuit 80 may establish the T-wave morphology criteria to be distinct from the R-wave morphology criteria that is used to validate sensed event signals in order to discriminate between ventricular sensed event signals associated with oversensed T-waves from ventricular sensed event signals associated with true R-waves.

When the R-wave criteria are met at block 862, the ECG signal segments stored in response to sensed event signals occurring at short intervals may correspond to ectopic beats. In this case, control circuit 80 may establish ectopic beat morphology criteria at block 866. The short, sensed event interval at which the likely ectopic beat is sensed (sometimes referred to as the "coupling interval") may be used to establish an ectopic beat interval threshold range that is characteristic for the patient. Additionally or alternatively, control circuit 80 may establish ectopic beat morphology feature criteria based on the morphology features determined at block 860. The morphology features for which ectopic beat morphology criteria are established may or may not be the same morphology features used to establish P-wave and/or T-wave morphology criteria. The ectopic beat morphology criteria may include criteria that discriminate between sinus R-waves and ectopic or aberrantly conducted R-waves.

Control circuit 80 may use the P-wave, T-wave and/or ectopic beat morphology criteria established using the methods of flow chart 824 for validating sensed event signals for use in controlling bradycardia pacing by ICD 14. Referring again to FIG. 15, control circuit 80 may be configured to determine when the sum of pairs of alternating intervals (corrected intervals) are greater than or equal to the pacing escape interval ("yes" branch of block 816) and/or when non-alternating intervals are detected after a series of alternating intervals ("yes" branch of block 822). In response to detecting either of these conditions, control circuit 80 may determine that oversensing may be causing pacing inhibition (block 818). Control circuit 80 may advance to the process of flow chart 870 in FIG. 20.

Figure 20:
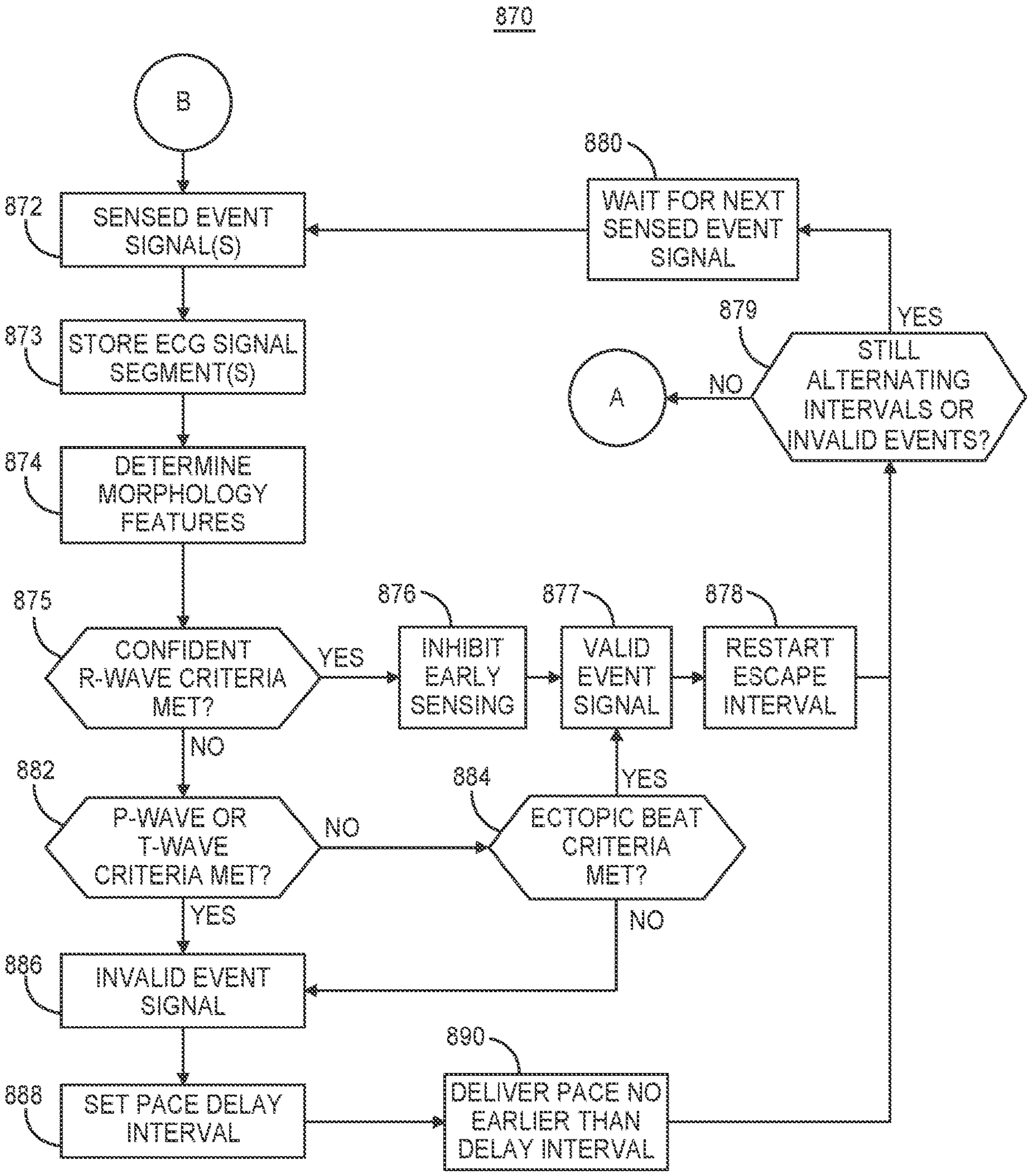
FIG. 20 is a flow chart of a method for controlling cardiac pacing pulse delivery when oversensing is suspected with possible pacing inhibition according to one example.

FIG. 20 is a flow chart 870 of a method for controlling cardiac pacing pulse delivery when oversensing is suspected with possible pacing inhibition according to one example. In response to detecting alternating intervals, or a change from alternating to non-alternating intervals as described above, control circuit 80 may perform morphology analysis that discriminates oversensed events from R-waves in the process of validating sensed event signals. At block 872, control circuit 80 receives a sensed event signal from a sensing channel 83 or 85. A first, earliest sensed event signal outside a previous validation window causes control circuit 80 to start the validation window. An associated ECG signal segment is buffered at block 873. Since oversensing may be occurring on both channels when two sensed event signals are received within a validation window of each other, the morphology analysis of flow chart 870 may be performed for at least one ECG signal segment associated with at least one ventricular sensed event signal regardless of whether a single ventricular sensed event signal is received from one sensing channel 83 or 85 or two ventricular sensed event signals are received, one from each sensing channel 83 and 85, within the validation window of each other.

When a second ventricular sensed event signal is not received, the morphology analysis performed according to the techniques of flow chart 870 may be performed on the ECG signal segment buffered at block 873 in response to the first, earliest sensed event signal received at block 872. When ventricular sensed event signals are received from both sensing channels 83 and 85 within the validation window, both channels may be oversensed P-waves, T-waves or noise resulting in two sensed event signals, one from each sensing channel 83 and 85. In this case, control circuit 80 may store an ECG signal segment associated with each ventricular sensed event signal at block 873, or at least the first, earliest ventricular sensed event signal, and perform morphology analysis on one or both ECG signal segments for discriminating oversensed signals from true R-waves.

In some examples, control circuit 80 may determine whether to analyze one or two ECG signal segments based on the temporal separation of two ventricular sensed event signals occurring within the validation window. When the two ventricular sensed event signals occur within a threshold time interval of each other, e.g., the second ventricular sensed event signal is received early in the validation window such that the two ECG signal segments would be substantially overlapping, a single ECG signal segment may be stored at block 873 and subsequently analyzed by control circuit 80. When the second sensed event signal received at block 872 occurs nearer to the end of the validation window, outside a threshold time interval from the first, earliest ventricular sensed event signal, a second ECG signal segment may be buffered at block 873 in response to the second, later ventricular sensed event signal. Both of the first and second ECG signal segments may be analyzed by control circuit 80 according to the morphology analysis of flow chart 870 for identifying oversensed signals.

At block 874, control circuit 80 determines morphology features of the ECG signal segment(s). Morphology features determined at block 874 may include all morphology features required to determine if confident R-wave criteria are met at block 875 and, if not, whether P-wave and/or T-wave criteria are met at block 882 according to the morphology criteria established using the techniques described in conjunction with FIG. 19.

At block 875, control circuit 80 may determine if the morphology features determined from at least one (or both) ECG signal segment(s) meet confident R-wave criteria. Confident R-wave criteria may be met when the morphology matching score between the buffered ECG signal segment and a previously stored R-wave template is greater than a threshold. When the morphology matching score is greater than a confident R-wave matching score threshold at block 875, control circuit 80 may determine that the associated ventricular sensed event signal is valid at block 877 and restart the pacing escape interval at block 878. The pacing escape interval may be restarted to have an effective starting time according to a determined sensed event time (e.g., at the time of the first, earliest ventricular sensed event signal or a midpoint between two ventricular sensed event signals received within the validation window).

In some examples, when the confident R-wave criteria are met at block 875, control circuit 80 may optionally inhibit early sensing at block 876, e.g., by extending a post-sense blanking period, a post-sense refractory period or increasing the R-wave sensing threshold for an early sensing time period, as generally described above in conjunction with FIG. 6 (block 227). During the post-sense refractory period, ventricular events may be sensed by the sensing channels 83 and 85 for detecting tachyarrhythmia intervals, for example, but may be ignored for the purposes of controlling bradycardia pacing. The post-sense refractory period may be set to an early sensing time period following a ventricular sensed event signal during which another true R-wave is highly unlikely to occur during normal sinus rhythm due to the physiological refractory period of the myocardial tissue. Control circuit 80 may set the post-sense refractory period based on an ectopic beat coupling interval known for the patient in some examples to enable non-refractory sensing of ectopic beats but avoid oversensing of other events. The post-sense refractory period may be set up to 400 ms in some examples. By inhibiting early sensing at block 876 after detecting alternating event intervals, control circuit 80 may break a sequence of alternating event intervals due to oversensing and decrease the likelihood of inhibiting a pacing pulse due to oversensing.

When confident R-wave criteria are not met at block 875, control circuit 80 may apply P-wave and/or T-wave morphology criteria at block 882. If alternating intervals are still occurring and the first earliest sensed event signal is received at a short interval, which may be an in-channel sensed event interval, T-wave morphology criteria may be applied. If alternating intervals are still occurring and the first, earliest sensed event signal is received at a long interval, P-wave morphology criteria may be applied. The morphology criteria established according to the methods of FIG. 19 may be applied to the ECG signal segment (or both a first and second ECG signal segment when two are stored at block 873).

In an illustrative example, control circuit 80 may determine whether the maximum peak amplitude of the rectified ECG signal is within a P-wave amplitude range. Additionally or alternatively, control circuit 80 may determine whether the slope difference of the ECG signal segment is within a P-wave slope range. When the P-wave amplitude and slope criteria are met at block 882, control circuit 80 determines the sensed event signal(s) to be invalid at block 886. In some examples, control circuit 80 may additionally require that the first, earliest ventricular sensed event signal is received within a P-R interval range from a preceding valid event signal or a preceding ventricular sensed event signal produced by the same sensing channel.

Control circuit 80 may additionally or alternatively apply T-wave criteria to the ECG signal segment(s) at block 882. The T-wave criteria may include a T-wave amplitude range and/or a T-wave slope difference range that are compared to the maximum peak amplitude of the rectified signal and the peak-to-peak amplitude of the first order difference signal, respectively. While the maximum rectified peak amplitude and peak-to-peak difference of the first order difference signal are given as examples of morphology features compared to criteria defined as respective ranges of these features, it is to be understood that other morphology features or combinations of morphology features may include any of the examples listed herein, with associated morphology criteria defined by distinct ranges, thresholds or other values for P-waves, T-waves and/or R-waves. In some examples, the T-wave criteria may require that the ventricular sensed event signal occur at an in-channel sensed event interval or at an interval from the most recent valid event signal that falls within a R-T interval range. The T-wave will always occur at a short (R-T) interval during alternating intervals. P-waves may or may not occur at a long (R-P) interval during alternating intervals because, during AV conduction block, R-waves may not be present. Accordingly, interval criteria may be included in the criteria applied at block 882 in conjunction with morphology criteria in some examples, at least for identifying T-wave oversensing.

When P-wave criteria or T-wave criteria are met at block 882, control circuit 80 determines the sensed event signal(s) to be invalid at block 886. If P-wave and T-wave criteria are not met at block 882, the ventricular sensed event signal may correspond to oversensed noise or a sensed ectopic beat. An ectopic beat signal may not meet confident R-wave criteria at block 875 due to the morphology matching score being less than the confident R-wave matching score threshold. Control circuit 80 may apply other ectopic beat morphology criteria at block 884 based on morphology features other than the morphology matching score and/or based on an ectopic beat morphology match score range. Ectopic beat morphology criteria that are applied at block 884 may be established previously according to the techniques described in conjunction with FIG. 19. Ectopic beat morphology criteria may include morphology features corresponding to sensed event signals that are received by control circuit 80 at a characteristic coupling interval from a preceding, valid event signal. For example, when the first, earliest sensed event signal is received at block 872 within an ectopic beat coupling range (from an in-channel ventricular sensed event signal or preceding valid event signal) and one or more morphology features match ectopic beat criteria, the first, earliest ventricular sensed event signal may be identified as a valid event signal at block 877. The morphology features evaluated at block 884 may include a signal width, signal peak amplitude, slope difference, polarity, polarity pattern or other features or combination of features established as ectopic beat morphology criteria. The pacing escape interval is restarted at block 878 in response to the valid event signal.

When control circuit 80 determines that the ectopic beat criteria are not met at block 884, the first, earliest ventricular sensed event signal may be caused by oversensed noise. Control circuit 80 determines the received ventricular sensed event signal(s) to be invalid at block 886.

The process of flow chart 870 addresses the situation that could arise when both sensing channels 83 and 85 are oversensing. In the process described above in conjunction with FIG. 6, sensed event signals could be occurring at alternating intervals due to oversensing and may be validated based on a second oversensed event signal within the validation window of a first, earlier oversensed event signal. In some instances a sensed event signal may be falsely validated. By performing additional analysis, when alternating intervals are detected, inhibition of bradycardia pacing pulses due to false valid event signal determination can be avoided.

In response to an invalid signal determination at block 886, control circuit 80 may allow a pacing escape interval that has not yet expired to continue running. When a pacing escape interval has expired after the first, earliest ventricular sensed event signal received at block 872 but before the determination of an invalid event signal at block 886, control circuit 80 may control the therapy delivery circuit 86 to withhold the pending pacing pulse and subsequently deliver the pending pacing pulse upon determination of the invalid event signal. The pending pacing pulse may be delivered upon expiration of the validation window or as soon as processing for morphology signal analysis is complete and the invalid event signal determination is known In some examples, as shown in FIG. 20, control circuit 80 may set a pace delay interval at block 888 in response to determining an invalid event signal. In some instances, a ventricular sensed event signal may be falsely determined to be invalid. For instance, a first, earliest ventricular sensed event signal received at block 872 may be determined to be invalid when it actually corresponds to a true R-wave or ventricular depolarization signal. As described above in conjunction with FIG. 6, a pace delay interval may be set to 400 to 800 ms, as examples, to avoid pacing until after a vulnerable period when the invalid event signal actually corresponds to a true R-wave. If the pacing escape interval expires before the pace delay interval, control circuit 80 may control therapy delivery circuit 86 to withhold the scheduled pacing pulse until the pace delay interval expires at block 890. A pending pacing pulse scheduled to be delivered at the expiration of a pacing escape interval that occurs during the validation window or before the pace delay interval may be delivered upon expiration of the pace delay interval at block 890. A pending pacing pulse that is scheduled at the expiration of a pacing escape interval that is running at the time of the invalid event signal determination at block 888 and ultimately expires after the pace delay interval (and before a next valid sensed event signal) may be delivered by therapy delivery circuit 86 upon expiration of the escape interval.

If a valid event signal is identified during the pace delay interval, the pacing escape interval may be restarted in response to the valid event signal and the pending cardiac pacing pulse may be cancelled. However, if an invalid event signal is identified during the pace delay interval, the pending pacing pulse may still be delivered upon expiration of the pace delay interval. Control circuit 80 may be configured to allow a previously started pace delay interval to continue running without restarting the pace delay interval in response to a second invalid event signal consecutively following a previous invalid event signal. In this way, when an invalid event signal is identified during episodes of possible oversensing, pacing pulse delivery during a vulnerable period may be avoided if a false invalid event signal determination is made.

After either delivering a pending pacing pulse or restarting the escape interval, control circuit 80 may advance to block 880 to wait for the next, first earliest ventricular sensed event signal. Before returning to block 872, however, control circuit 80 may determine at block 879 if alternating intervals are still being detected and/or invalid event signal determinations are still being made at block 886. The additional analysis for determining if P-wave or T-wave criteria are met according to flow chart 870 may be performed by control circuit 80 only when alternating intervals are or have been recently detected and/or invalid event signal determinations continue to be made at block 886 based on the additional morphology analysis. If so, control circuit 80 may wait for the next sensed event signal at block 880 and continue using the P-wave and T-wave morphology criteria for validating sensed event signals. Once valid event signals are determined at non-alternating intervals, e.g., for a threshold number of event signals or over a predetermined time interval, ("no" branch of block 879) control circuit 80 may return to block 802 of FIG. 15 (as indicated by connector "A") until alternating intervals are again detected.

Figure 21:
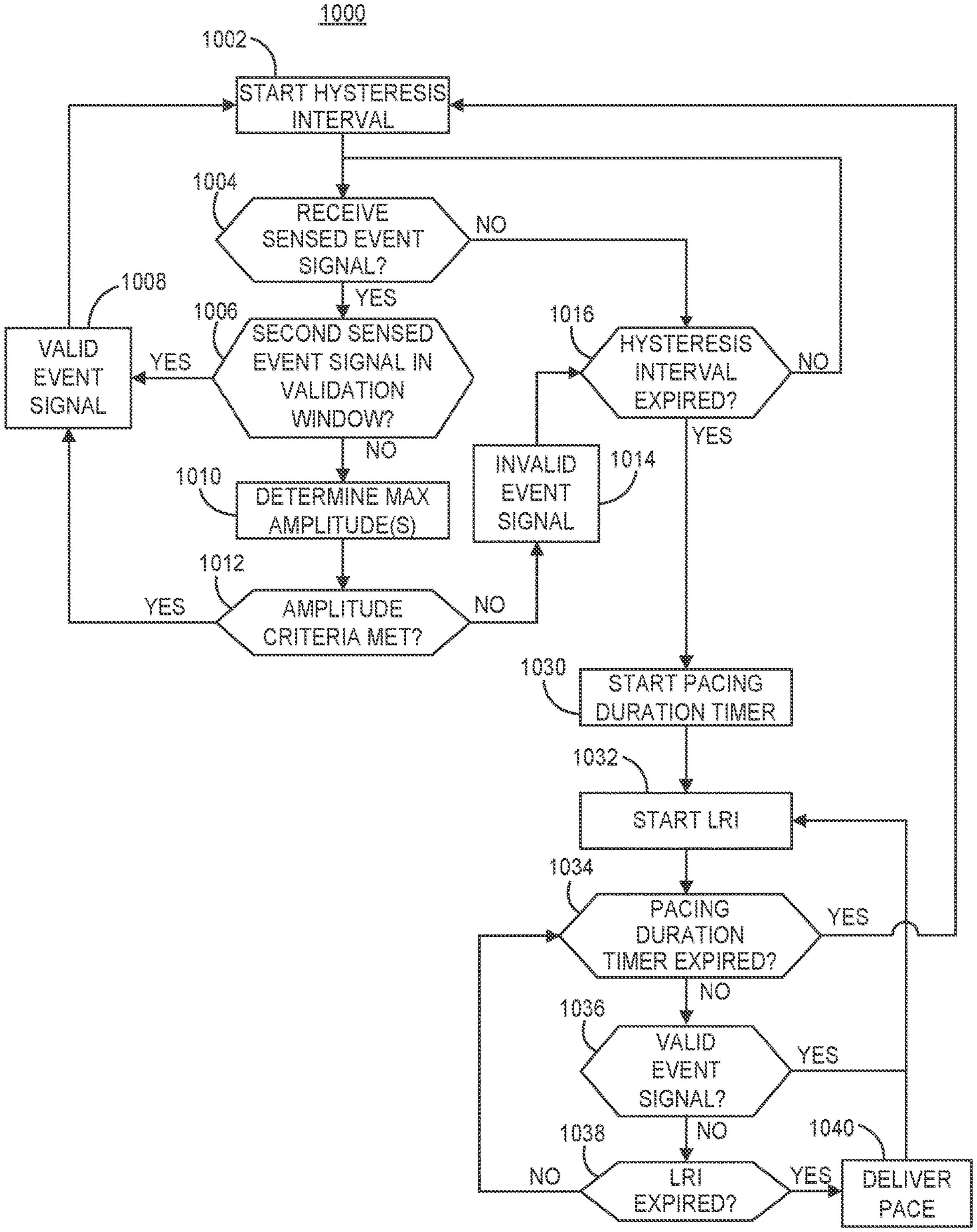
FIG. 21 is a flow chart of a method performed by a medical device for sensing cardiac event signals and controlling cardiac pacing according to another example.

FIG. 21 is a flow chart 1000 of a method for sensing cardiac event signals and controlling cardiac pacing according to another example. In the examples described above, an ECG signal segment received by control circuit 80 from the morphology sensing channel 87 may be buffered in response to a ventricular sensed event signal. The ECG signal segment can be analyzed by control circuit 80 for determining when a ventricular sensed event signal is a valid or an invalid event signal according to the various examples described above. In the example of FIG. 21, control circuit 80 may be configured to identify valid event signals according to one method during a hysteresis interval and according to a different method during an LRI. Buffering and analyzing an ECG signal segment received from the morphology sensing channel 87 for determining valid and invalid event signals each time one of sensing channels 83 or 85 produces a sensed event signal may require considerable processing power. In order to provide bradycardia or asystole pacing when needed without significantly shortening the useful life of power source 98 (FIG. 3) due to high processing burden, a less processing intensive method for validating ventricular sensed event signals may be used during a hysteresis interval than during an LRI that is started in response to delivering a ventricular pacing pulse due to a need for ventricular pacing or in response to an identified valid event signal. The method for validating ventricular sensed event signals during the hysteresis interval may involve analysis of only the ECG signals sensed by the sensing channels 83 and 85 without requiring analysis of an ECG signal sensed by the morphology sensing channel 87. If the hysteresis interval expires, control circuit 80 may switch to a second method for validating ventricular sensed event signals that may involve analysis of a buffered ECG signal segment received from morphology sensing channel 87 to promote reliable sensing of R-waves and delivery of ventricular pacing pulses as needed. During a hysteresis interval, control circuit 80 may identify a valid event signal sensed by the sensing circuit during the hysteresis interval based on a first analysis of a first portion of the multiple cardiac electrical signals sensed by the sensing circuit. During an LRI, control circuit 80 may determine that a ventricular event signal sensed by sensing circuit 86 is one of a valid event signal or an invalid event signal based on a second analysis of a second portion of the multiple cardiac electrical signals sensed by the sensing circuit. The second analysis can be different than the first analysis, and the first portion of the multiple cardiac electrical signals can be different than the second portion of the multiple cardiac electrical signals. For example, the first portion of the multiple cardiac electrical signals may be the signals sensed by sensing channels 83 and 85. The second portion of the multiple cardiac electrical signals may be the signals sensed by sensing channels 83 and 85 and the morphology signal channel 87.

In the example of FIG. 21, control circuit 80 starts a hysteresis interval at block 1002. As generally described above, e.g., in conjunction with FIG. 11, the hysteresis interval may be 2 to 6 seconds long in various examples and is 2.5 seconds in one example. Control circuit 80 may start the hysteresis interval at block 1002 upon initial implantation of ICD 14, after a threshold number of valid event signals that caused the LRI to be restarted without delivery of a pacing pulse, and/or after expiration of a pacing duration timer as generally described above in conjunction with FIG. 11.

Control circuit 80 may start a pacing escape interval timer set equal to the hysteresis interval when the hysteresis interval is started at block 1002. However, in some examples, a pacing escape interval may not be started when the hysteresis interval is started at block 1002. Control circuit 80 may start a hysteresis interval without scheduling a pacing pulse. As described below, when the hysteresis interval expires, control circuit 80 may deliver a pacing pulse or may start a pacing escape interval timer set to the LRI to schedule a pending pacing pulse without delivering a pacing pulse immediately after the hysteresis interval expires.

If control circuit 80 receives a ventricular sensed event signal during the hysteresis interval ("yes" branch of block 1004), control circuit 80 may determine if a second sensed event signal is received within the validation window at block 1006. In some examples, if a ventricular sensed event signal is received from both sensing channels 83 and 85 within the validation window, control circuit 80 may determine a valid event signal at block 1008. As described above, in response to the first, earliest ventricular sensed event signal received outside of any applied refractory periods or a previously started validation window, control circuit 80 may start the validation window. When a second, later ventricular sensed event signal is received from the other sensing channel before the validation window expires, the received ventricular sensed event signals may be identified (collectively) as a valid event signal at block 1008. Control circuit 80 may restart the hysteresis interval at block 1002.

In this case, during the hysteresis interval, control circuit 80 may start the validation window in response to a received ventricular sensed event signal but does not buffer and analyze an ECG signal segment received from the morphology sensing channel 87 for use in validating the received ventricular sensed event signal. Instead, if a ventricular sensed event signal is received at block 1004 and a second sensed event signal is not received during the validation window, control circuit 80 may analyze the amplitude (and/or other features) of one or both of the ECG signals sensed by sensing channels 83 and/or 85. In other examples, when a ventricular sensed event signal is received at block 1004, control circuit 80 may advance to block 1010 to analyze the amplitude of the ECG signals sensed by sensing channels 83 and 85 regardless of whether a second sensed event signal is received during the validation window. In other words, block 1006 may be omitted in some examples such that, when a hysteresis interval is running, control circuit 80 determines a valid event signal based on an analysis of the amplitude of the ECG signals sensed by sensing channels 83 and 85 during the validation window started in response to a ventricular sensed event signal received from either one of sensing channels 83 or 85.

At block 1010, control circuit 80 may determine the maximum peak amplitude of the rectified ECG signal sensed during the validation window by each sensing channel 83 and 85. The validation window may be 50 to 200 ms long and is 105 ms long in some examples. As described above, the validation window can be started by control circuit 80 in response to a ventricular sensed event signal received from either sensing channel 83 or 85 outside of a previously started refractory period and/or outside a previously started validation window. The maximum peak amplitude of the rectified ECG signal sensed by sensing channel 83 during the validation window may be stored in memory 82 as MaxAmp1. The maximum peak amplitude of the rectified ECG signal sensed by sensing channel 85 during the validation window may be stored in memory 82 as MaxAmp2.

At block 1012, control circuit 80 may compare the maximum peak amplitudes, MaxAmp1 and MaxAmp2, to amplitude criteria for determining whether the ventricular sensed event signal received at block 1004 is a valid event signal or an invalid event signal. Control circuit 80 may determine if each of MaxAmp1 and MaxAmp2 are greater than a respective threshold amplitude at block 1012. Control circuit 80 may establish the threshold amplitude as a percentage of a representative amplitude of the respective ECG signal. For example, control circuit 80 may establish the threshold amplitude for each ECG signal as a percentage of a long term average amplitude of the respective ECG signal. A method for establishing the threshold amplitude as a percentage of a long term average of maximum amplitudes of the respective ECG signals is described below in conjunction with FIG. 23. In other examples, the threshold amplitude may be a specified, e.g., programmable, value stored in memory 82 or a percentage of the programmed sensitivity of the respective sensing channel.

When the amplitude criteria are met at block 1012, control circuit 80 determines that the ventricular sensed event signal received at block 1004 during the hysteresis interval is a valid event signal at block 1008. As indicated above, block 1006 may be omitted such that the first, earliest ventricular sensed event signal may be determined to be a valid event signal based on the determined MaxAmp1 and MaxAmp2 regardless of whether a second, later ventricular sensed event signal is received from the other sensing channel during the validation window.

In response to determining a valid event signal, control circuit 80 restarts the hysteresis interval at block 1002. When a ventricular sensed event signal is received during the hysteresis interval and the determined MaxAmp1 and MaxAmp2 do not meet the amplitude criteria at block 1012, control circuit 80 may determine that the received ventricular sensed event signal is an invalid event signal at block 1014. Control circuit 80 may determine that the first, earliest ventricular sensed event signal is an invalid event signal based on the amplitude criteria not being met regardless of whether a second, later ventricular sensed event signal is received during the validation window (block 1006 can be omitted). If the hysteresis interval has not expired ("no" branch of block 1016), control circuit 80 may return to block 1004 to wait for any subsequent ventricular sensed event signals that may be received during the hysteresis interval.

When the hysteresis interval expires without a valid event signal being identified during the hysteresis interval ("yes" branch of block 1016), control circuit 80 may start a pacing duration timer at block 1030. As described above, e.g., in conjunction with FIG. 11, control circuit 80 may set a maximum time period for delivering ventricular pacing at the programmed lower rate. The pacing duration timer may be set to a time interval of 1 minute, 5 minutes, 10 minutes, 15 minutes, 20 minutes, 30 minutes, one hour or other selected time period. It is contemplated that the pacing duration timer may be set to increasingly longer time intervals when the hysteresis interval repeatedly expires without a valid event signal (more pacing needed) and may be set to decreasingly shorter time intervals or reset to a short or minimum time interval when valid event signals are repeatedly identified during hysteresis intervals (less pacing needed). The pacing duration timer may be set to an adjustable time interval by control circuit 80 based on the history of pacing frequency needed by the patient, number of hysteresis intervals that are reset due to a valid event signal, number of hysteresis intervals that expire without valid event signals, number of pacing pulses delivered during the maximum pacing time period (while the pacing duration timer is running), etc.

Upon starting the pacing duration timer, control circuit 80 may start a pacing escape interval timer set to the LRI at block 1032 to schedule a pending cardiac pacing pulse. In the example shown, the first pacing pulse after the hysteresis interval expires is scheduled at the LRI after the hysteresis interval expiration. Control circuit 80 may not schedule delivery of a pacing pulse at the expiration of the hysteresis interval such that therapy delivery circuit 84 does not immediately deliver a pacing pulse in response to the hysteresis interval expiring. In other examples, control circuit 80 may schedule a pacing pulse at the hysteresis interval expiration. Therapy delivery circuit 84 may deliver a pacing pulse when the pacing duration timer is started at block 1030 and the LRI is started at block 1032 in response to the expired hysteresis interval.

During a running LRI, control circuit 80 may identify valid event signals using a different method than during the hysteresis interval(s). When a hysteresis interval has expired and is not restarted, control circuit 80 may identify valid event signals according to any of the example techniques described above in conjunction with FIGS. 5-20. For example, control circuit 80 may buffer an ECG signal segment received from the morphology sensing channel 87 in response to a received ventricular sensed event signal for use in identifying valid event signals according to any of the example techniques described above. The buffered ECG signal segment may be analyzed to determine if R-wave morphology criteria are met when a second ventricular sensed event signal is not received during a validation window started in response to a first, earlier ventricular sensed event signal. As described above, in some examples, the buffered ECG signal is analyzed to determine if R-wave morphology criteria are met even when a ventricular sensed event signal is received from each sensing channel 83 and 85 during a validation window.

When a valid event signal is identified at block 1036 before the LRI expires ("no" branch of block 1038) and before the pacing duration timer is expired ("no" branch of block 1034), control circuit 80 may restart the pacing escape interval timer set to the LRI at block 1032 to schedule the next pending pacing pulse. If the LRI expires at block 1038 without a valid event signal ("no" branch of block 1036) during the LRI, therapy delivery circuit 84 can deliver a pending pacing pulse at block 1040. Control circuit 80 restarts the pacing escape interval timer set to the LRI at block 1032. As described above, the pacing pulse may be delivered at block 1040 after a validation window or after a pace delay interval if the LRI expires during a validation window.

When the pacing duration timer expires ("yes" branch of block 1034), control circuit 80 returns to block 1002 and starts the hysteresis interval. Buffering and analysis of the ECG signal received from the morphology sensing channel 87 may be terminated for the purposes of identifying valid event signals and controlling ventricular pacing (although the ECG signal from the morphology sensing channel 87 may be processed and analyzed for other purposes such as tachyarrhythmia detection). In this way, higher processing burden methods for identifying valid event signals are triggered by the expiration of a hysteresis interval that occurs without a received ventricular event signal that is validated based on lower processing burden methods, e.g., based only on the amplitudes of the ECG signals sensed by the sensing channels 83 and 85 without analyzing the ECG signal sensed by the morphology signal channel 87.

Figure 22:
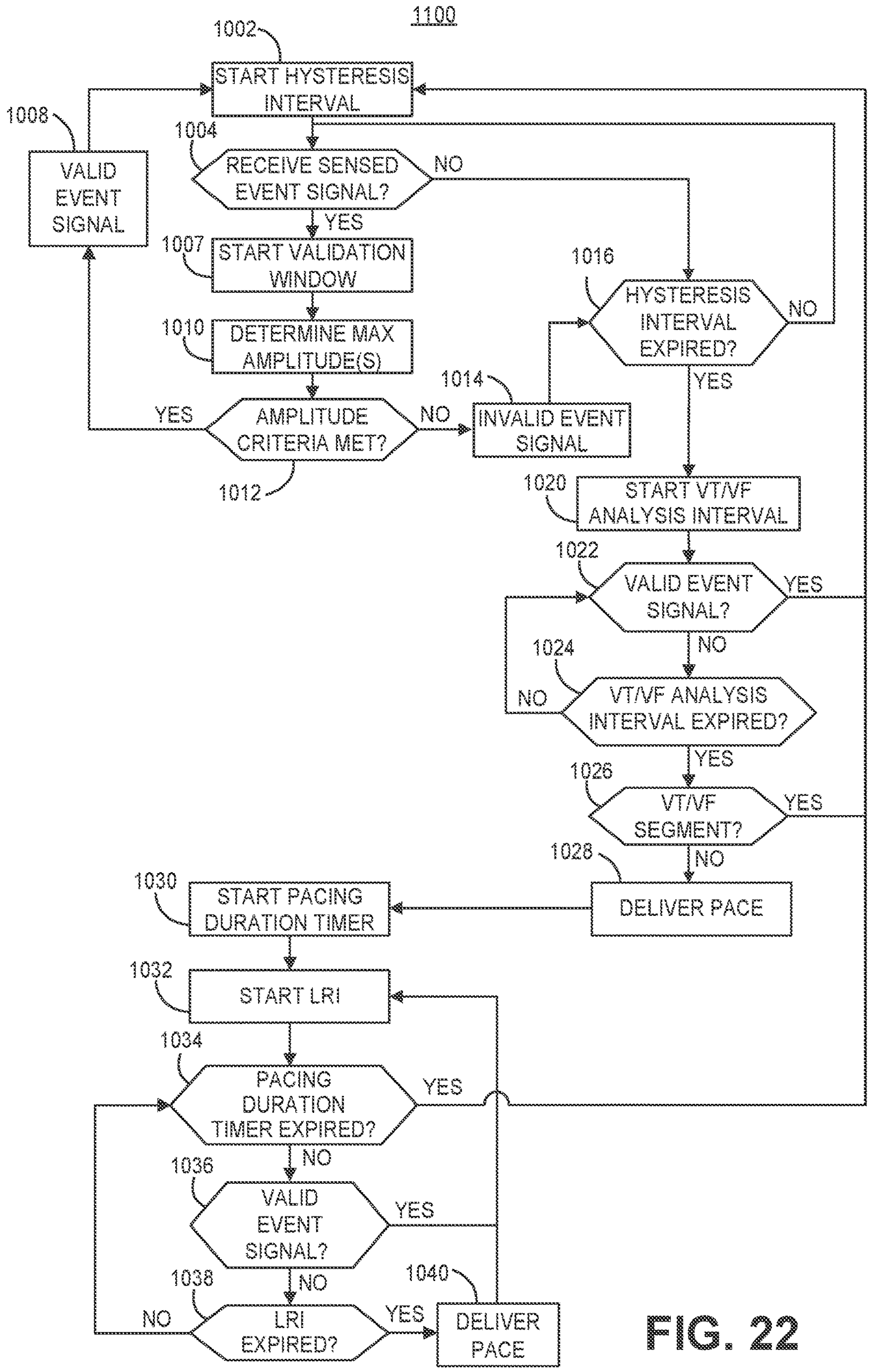
FIG. 22 is a flow chart of a method performed by a medical device for sensing cardiac electrical signals and controlling cardiac pacing according to yet another example.

FIG. 22 is a flow chart 1100 of a method performed by a medical device for sensing cardiac electrical signals and controlling cardiac pacing according to yet another example. Identically numbered blocks in FIG. 22 correspond to like-numbered blocks shown in FIG. 21 and are described above. In the example of FIG. 22, block 1006 is omitted. Control circuit 80 starts a hysteresis interval at block 1002. When a ventricular sensed event signal is received at block 1004 from either sensing channel 83 or 85 outside a validation window, control circuit 80 starts a validation window at block 1007 and determines MaxAmp1 and MaxAmp2 (block 1010) from the respective ECG signals sensed by sensing channel 83 and sensing channel 85 during the validation window. Control circuit 80 compares the MaxAmp1 and MaxAmp2 to amplitude criteria at block 1012 for determining if the received ventricular sensed event signal is valid (at block 1008 leading back to block 1002 for restarting the hysteresis interval) or invalid (at block 1014 leading to block 1016).

In the example of FIG. 22, if the hysteresis interval expires at block 1016 without a valid event signal, control circuit 80 may start a tachyarrhythmia analysis interval (VT/VF analysis interval) at block 1020. Control circuit 80 may verify that VT/VF is unlikely to be present by analyzing at least one ECG signal before scheduling or delivering a ventricular pacing pulse that could create a pacing artifact and interfere with VT/VF detection. Control circuit 80 may analyze one or more of the ECG signals sensed by sensing circuit 86 during the tachyarrhythmia analysis interval for determining evidence of VT/VF. The tachyarrhythmia analysis interval may be 0.3 to 4 seconds long, for instance, and may be 3 seconds long in an example. Control circuit 80 may determine one or more morphology metrics from the ECG signal sensed by morphology signal channel 87 during the tachyarrhythmia analysis interval for classifying an ECG signal segment as a VT/VF signal segment or a non-VT/VF signal segment. Example methods for determining if an ECG signal segment includes morphological evidence of VT/VF that could be performed by control circuit 80 during the process of flow chart 1100 are generally described in U.S. Patent Application No. 63/310,558 and corresponding International PCT Publication No. WO2023/159031 (Heinks, et al), U.S. Pat. No. 7,774,049 (Ghanem, et al.) and in U.S. Pat. No. 10,750,970 (Stadler, et al), each of which is incorporated herein by reference in its entirety.

In an example, a VT/VF signal segment may be identified when the ECG signal sensed during a 3-second tachyarrhythmia analysis interval has a mean period of at least 60 ms, spectral width less than or equal to 10 ms and a low slope content less than or equal to 0.7. The foregoing thresholds are illustrative in nature and not to be considered limiting. The thresholds or other criteria applied to the signal sensed during the tachyarrhythmia analysis interval may vary depending on the time duration of the tachyarrhythmia analysis interval and other factors. Different morphology features may be determined and/or different thresholds applied. The techniques disclosed herein are not limited to a particular method for identifying evidence of VT/VF in the signal sensed during the tachyarrhythmia analysis interval. A variety of methods may be employed for identifying VT/VF evidence in the sensed signal. Control circuit 80 may determine that the ECG signal sensed during the tachyarrhythmia analysis interval is or includes a VT/VF signal segment according to one or a combination of signal morphology parameters meeting respective thresholds. Reference is made, for example, to the foregoing incorporated references and to U.S. Patent Application No. 63/278,955 and corresponding U.S. patent application Ser. No. 18/045,135, published as U.S. Patent Application Publication No. 2023/0148939 (Aranda-Hernandez, et al), incorporated herein by reference in its entirety.

In various examples, control circuit 80 may determine one or more morphology metrics from an ECG signal segment sensed during the tachyarrhythmia analysis interval that discriminate between true VT/VF rhythms and other non-VT/VF conditions, such as asystole or a long pause. In some cases, fibrillation waves may have a low amplitude and may be undersensed during the hysteresis interval. Morphology metrics, therefore, can be determined from sample points spanning an entire ECG signal segment and are not dependent on identifying valid event signals during the tachyarrhythmia analysis interval. In some instances, no ventricular sensed event signals may be received from sensing circuit 86 during the tachyarrhythmia analysis interval. As examples, control circuit 80 may determine a low slope content (LSC), a mean period (MP), a spectral width (SW), a noise pulse count, a mean rectified amplitude (MRA), a normalized mean rectified amplitude (NMRA), and/or other morphology metrics from the ECG signal received from the morphology signal channel 87 during the tachyarrhythmia analysis interval.

During the tachyarrhythmia analysis interval, control circuit 80 may receive a ventricular sensed event signal from sensing circuit 86, from either of sensing channels 83 or 85. Control circuit 80 may buffer an ECG signal segment for use, as needed, in determining if a received ventricular sensed event signal is a valid event signal according to any of the example techniques presented herein at block 1022. If a valid event signal is identified during the tachyarrhythmia analysis interval ("yes" branch of block 1022), control circuit 80 may return to block 1002 to restart the hysteresis interval, without delivering a pacing pulse. Control circuit 80 may switch back to the first method of analysis for identifying valid event signals during the hysteresis interval.

If a valid event signal is not identified during the tachyarrhythmia analysis interval ("no" branch of block 1022), and the tachyarrhythmia analysis interval has expired ("yes" branch of block 1024), control circuit 80 determines if the analyzed ECG signal segment is a VT/VF signal segment based on the signal morphology. If VT/VF morphology criteria are met by the morphology metric(s) determined during the tachyarrhythmia analysis interval, control circuit 80 may avoid pacing into a tachyarrhythmia rhythm by returning to block 1002 ("yes" branch of block 1026) and restarting the hysteresis interval. It is to be understood that an ECG signal segment sensed during the tachyarrhythmia analysis interval by sensing channel 83, sensing channel 85 and/or sensing channel 87 may be analyzed for detecting a VT/VF signal segment at block 1026.

If a VT/VF signal segment is not identified from the ECG signal sensed during the tachyarrhythmia analysis interval ("no" branch of block 1026), therapy delivery circuit 84 may deliver a ventricular pacing pulse at block 1028 in response to the tachyarrhythmia analysis interval expiring without a valid event signal. In other examples, depending on the total time duration of the hysteresis interval and the tachyarrhythmia analysis interval, control circuit 80 may start a LRI for scheduling a pacing pulse in response to the tachyarrhythmia analysis interval expiring without a valid event signal and without detecting a VT/VF signal segment. Control circuit 80 may start the pacing duration timer at block 1030. Control circuit 80 may enable ECG signal segment buffering and the second method of analysis of ECG signals for identifying valid and invalid event signals during LRIs, as generally described above in conjunction with FIG. 21. In this way, the second method of analysis of ECG signals for identifying valid event signals that includes buffering and analysis of ECG signal segments received from the morphology sensing channel 87 may be triggered by an expired hysteresis interval and determination of a non-VT/VF signal segment sensed during the subsequent tachyarrhythmia analysis interval. Control circuit 80 may start a pacing escape interval timer set to the LRI at block 1032. As described above, if a valid event signal is identified during the LRI ("yes" branch of block 1036), and the pacing duration timer has not expired ("no" branch of block 1034), control circuit 80 may restart the LRI at block 1032. As described above, when a LRI is restarted in response to a valid event signal, control circuit 80 may determine a sensed event time and start the pacing escape interval timer so that the LRI has an effective starting time at the determined sensed event time.

If a valid event signal is not identified prior to the expiration of a LRI ("yes" branch of block 1038), therapy delivery circuit 84 may deliver a ventricular pacing pulse at block 1040. Control circuit 80 restarts the LRI at block 1032 to schedule the next ventricular pacing pulse. When the pacing duration timer expires ("yes" branch of block 1034), control circuit 80 may return to block 1002 to start a hysteresis interval. The buffering and analysis of an ECG signal segment for the purposes of identifying valid event signals for controlling cardiac pacing (e.g., bradycardia or asystole pacing) may be disabled when the pacing duration time expires and the hysteresis interval is restarted. Control circuit 80 may switch back to identifying valid event signals based the amplitude (or another feature such as slew rate) of the ECG signals(s) sensed by sensing channel 83 and/or sensing channel 85 according to the first method of analysis of the ECG signals that can be sensed by sensing circuit 86.

Figure 23:
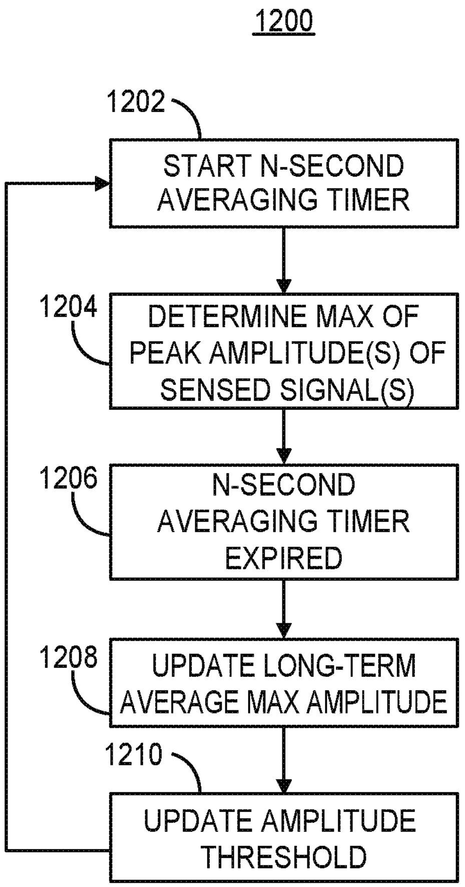
FIG. 23 is a flow chart of a method that may be performed by a medical device for establishing an amplitude threshold used for identifying valid event signals during a hysteresis interval according to some examples.

FIG. 23 is a flow chart 1200 of a method that may be performed by control circuit 80 for establishing an amplitude threshold used for identifying valid event signals during a hysteresis interval according to some examples. The process of flow chart 1200 may be performed on an ongoing basis when hysteresis intervals, tachyarrhythmia analysis intervals and/or LRIs are running to enable control circuit 80 to determine an average of the maximum peak amplitudes of the signals sensed by sensing channel 83 and sensing channel 85. A long-term average maximum amplitude for a given sensing channel is representative of maximum peak amplitudes of signals sensed by the respective sensing channel in response to an R-wave sensing threshold crossing. The process of flow chart 1200 may be performed for each of sensing channels 83 and 85.

At block 1202, control circuit 80 may start an n-second averaging timer. The n-second averaging timer may be set equal to, less than or greater than the hysteresis interval. In an example, the n-second averaging timer is set equal to 2 seconds and the hysteresis interval is set equal to 2.5 seconds. In other examples, an n-second averaging timer need not be set and a long-term average maximum amplitude may be updated in response to each maximum peak amplitude determined following a sensed event signal, which may or may not be a valid event signal sensed by a given sensing channel.

At block 1204, control circuit 80 may determine the peak amplitude of the respective ECG signal (sensed by sensing channel 83 or sensing channel 85) following each sensed event signal identified during the n-second averaging time interval. Control circuit 80 may determine the maximum one of the peak amplitudes of sensed signals upon expiration of the n-second averaging interval. The maximum amplitude can be used by control circuit 80 for determining a long-term average maximum amplitude. If no signals are sensed (e.g., no R-wave sensing threshold crossings) during the n-second averaging time interval, the maximum amplitude may be determined to be zero.

When the n-second averaging timer expires at block 1206, control circuit 80 may update a long-term average maximum amplitude at block 1208 using the maximum amplitude determined during the n-second averaging time interval. The maximum amplitude of the n-second averaging time interval may be averaged with the previously determined long-term average maximum amplitude using weighting coefficients to determine an updated long-term average. In an illustrative example, the long-term average may be determined as $LTA(n)=[(x)*LTA(n-1)+(1-x)*max(n)]$, where $LTA(n)$ is the long-term average of maximum amplitudes, $LTA(n-1)$ is the most recent determined LTA, $max(n)$ is the maximum amplitude of the currently expired n-second averaging time interval, and x and $1-x$ are weighting coefficients (where $0<x<1$). In an example, x is 31/32 though other weighting coefficients may be used. Other recursive filter methods may be used for determining a long term average using the maximum amplitude of the respective ECG signal during the most recent n-second averaging time interval (e.g., 1 to 3 seconds), one or more preceding maximum amplitudes determined from one or more respective preceding n-second averaging time intervals, the most recent LTA and/or one or more preceding LTAs, or any combination thereof, each assigned a respective weighting coefficient. In other examples, the LTA maximum amplitude may be determined as a moving average maximum amplitude that may be the average of the most recent 8, 12, 24, 32, 36, 50, 100 or other specified number of maximum peak amplitudes (determined following each ventricular sensed event signal or following each identified valid event signal).

At block 1210, control circuit 80 may update the amplitude threshold for the given sensing channel 83 or 85 based on the updated LTA maximum amplitude. For example, the amplitude threshold may be determined as 20%, 30%, 40%, 50% or another selected portion of the updated LTA maximum amplitude. In an example, control circuit 80 computes the amplitude threshold as 31.25% of the updated LTA maximum amplitude. Control circuit 80 may return to block 1202 to continue updating the amplitude threshold after every n-second averaging time interval.

Referring to block 1012 of FIG. 21 and FIG. 22, control circuit 80 may determine that the amplitude criteria are met for identifying a valid event signal when MaxAmp1 is greater than the amplitude threshold established for sensing channel 83 based on its LTA maximum amplitude and MaxAmp2 is greater than the amplitude threshold established for sensing channel 85 based on its LTA maximum amplitude. It is recognized, however, that a variety of methods may be conceived for establishing and updating an average maximum amplitude or other representative amplitude of the maximum peaks of signals sensed by each sensing channel 83 and 85. Furthermore, a variety of methods may be conceived for establishing and updating a threshold amplitude based on the representative amplitude. The amplitude criteria can be applied by control circuit 80 at block 1012 to determine when the amplitude of signals sensed by either sensing channel 83 or 85 has decreased from a relatively longer term average of the peak amplitudes of sensed signals suggesting that low amplitude R-waves or fibrillation waves could be present that are being undersensed. When decreased ECG signal amplitude is detected by control circuit 80 during a hysteresis interval, e.g., based on the amplitude criteria applied at block 1012, the tachyarrhythmia analysis interval may be triggered and/or the second method of analysis of ECG signals for identifying valid event signals may be triggered according to the techniques described in conjunction with FIGS. 21 and 22.

It should be understood that, depending on the example, certain acts or events of any of the methods described herein can be performed in a different sequence, may be added, merged, or left out altogether (e.g., not all described acts or events are necessary for the practice of the method). Moreover, in certain examples, acts or events may be performed concurrently, e.g., through multi-threaded processing, interrupt processing, or multiple processors, rather than sequentially. In addition, while certain aspects of this disclosure are described as being performed by a single circuit or unit for purposes of clarity, it should be understood that the techniques of this disclosure may be performed by a combination of units or circuits associated with, for example, a medical device.

In one or more examples, the functions described may be implemented in hardware, software, firmware, or any combination thereof. If implemented in software, the functions may be stored as one or more instructions or code on a computer-readable medium and executed by a hardware-based processing unit. Computer-readable media may include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPLAs), or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

Thus, a medical device has been presented in the foregoing description with reference to specific examples. It is to be understood that various aspects disclosed herein may be combined in different combinations than the specific combinations presented in the accompanying drawings. It is appreciated that various modifications to the referenced examples may be made without departing from the scope of the disclosure and the following claims.

What is claimed is:

1. A medical device comprising:

a therapy delivery circuit configured to generate pacing pulses;

a sensing circuit configured to:

receive a plurality of cardiac electrical signals; and sense a first ventricular event signal from a first cardiac electrical signal of the plurality of cardiac electrical signals; and a control circuit configured to:

start a pacing escape interval to schedule a pending cardiac pacing pulse;

start a validation window in response to the sensing circuit sensing the first ventricular event signal;

determine that the first ventricular event signal is one of a valid event signal or an invalid event signal based on at least a second cardiac electrical signal of the plurality of cardiac electrical signals received during the validation window by:

determining that the second ventricular event signal is sensed during the validation window; and determining that the first ventricular event signal is a valid event signal in response to determining that the second ventricular event signal is sensed by the sensing circuit during the validation window;

cancel the pending cardiac pacing pulse in response to determining that the first ventricular event signal is a valid event signal; and schedule a subsequent pending pacing pulse by restarting the pacing escape interval in response to determining that the first ventricular event signal is a valid event signal.

2. The medical device of claim 1, wherein the control circuit is further configured to:

determine that the pacing escape interval expires during the validation window; and control the therapy delivery circuit to withhold the pending cardiac pacing pulse that is scheduled at the expiration of the pacing escape interval in response to the pacing escape interval expiring during the validation window.

3. The medical device of claim 2, wherein the therapy delivery circuit is further configured to deliver the pending cardiac pacing pulse after the validation window in response to the control circuit determining that the first ventricular event signal is an invalid event signal.

4. The medical device of claim 1, wherein the control circuit is further configured to:

in response to determining that the first ventricular event signal is a valid event signal, determine a sensed event time;

determine an adjusted pacing escape interval having an effective starting time at the sensed event time; and restart the pacing escape interval set to the adjusted pacing escape interval having the effective starting time at the sensed event time.

5. The medical device of claim 1, further comprising a memory;

wherein the control circuit is further configured to determine that the first ventricular event signal is a valid event signal based on at least a third cardiac electrical signal of the plurality of cardiac electrical signals received during the validation window by:

storing a cardiac electrical signal segment from the third cardiac electrical signal in response to the first ventricular event signal being sensed by the sensing circuit, wherein at least a portion of the cardiac electrical signal segment is received during at least a portion of the validation window;

determining at least one morphology feature from the cardiac electrical signal segment;

determining that the at least one morphology feature from the cardiac electrical signal segment meets R-wave criteria; and determining that the first ventricular event signal is a valid event signal in response to the at least one morphology feature meeting the R-wave criteria and the second ventricular event signal being sensed during the validation window.

6. The medical device of claim 5, wherein the control circuit is further configured to: determine the at least one morphology feature by:

determining a peak amplitude of the cardiac electrical signal segment;

determining a difference signal from the cardiac electrical signal segment; and determining a peak-to-peak amplitude of the difference signal; and determine that the at least one morphology feature meets the R-wave morphology criteria in response to the peak amplitude being greater than an amplitude threshold and the peak-to-peak amplitude of the difference signal being greater than a slope threshold.

7. The medical device of claim 6, wherein the control circuit is further configured to determine the peak-to-peak amplitude difference of the difference signal from a portion of the cardiac electrical signal segment that occurs later than the first ventricular event signal.

8. The medical device of claim 1, wherein the control circuit is further configured to determine that the first ventricular event signal is one of a valid event signal or an invalid event signal based on at least the second cardiac electrical signal of the plurality of cardiac electrical signals by:

determining that the second ventricular event signal is not sensed from the second cardiac electrical signal during the validation window;

determining at least one morphology feature from a cardiac electrical signal segment of the plurality of cardiac electrical signals, wherein at least a portion of the cardiac electrical signal segment is received during at least a portion of the validation window;

determining that the at least one morphology feature does not meet R-wave criteria; and determining that the first ventricular event signal is an invalid event signal in response to determining that a second ventricular event signal is not sensed from the second cardiac electrical signal during the validation window and that the at least one morphology feature does not meet the R-wave criteria.

9. The medical device of claim 1, wherein the control circuit is further configured to:

start a hysteresis interval;

identify a valid event signal sensed by the sensing circuit during the hysteresis interval based on a first analysis of a first portion of the plurality of cardiac electrical signals;

restart the hysteresis interval in response to identifying the valid event signal;

detect an expiration of the restarted hysteresis interval without identifying a valid event signal during the restarted hysteresis interval;

start the pacing escape interval to schedule the pending cardiac pacing pulse in response to detecting the expiration of the restarted hysteresis interval, where the sensing circuit senses the first ventricular event signal from the first cardiac electrical signal of the plurality of cardiac electrical signals during the pacing escape interval; and determine that the first ventricular event signal is one of a valid event signal or an invalid event signal based on a second analysis of a second portion of the plurality of cardiac electrical signals including the second cardiac electrical signal, the second analysis different than the first analysis and the first portion of the plurality of cardiac electrical signals different than the second portion of the plurality of cardiac electrical signals.

10. The medical device of claim 1, wherein the control circuit is further configured to:

start a hysteresis interval;

detect an expiration of the hysteresis interval without identifying a valid event signal during the hysteresis interval;

start a tachyarrhythmia analysis interval in response to detecting the expiration of the restarted hysteresis interval before starting the pacing escape interval;

perform a morphology analysis of at least one of the plurality of cardiac electrical signals received by the sensing circuit during the tachyarrhythmia analysis interval;

detect a tachyarrhythmia segment of the at least one of the plurality of cardiac electrical signals based on the morphology analysis; and start a next hysteresis interval in response to detecting the tachyarrhythmia segment without scheduling a pacing pulse.

11. The medical device of claim 1, wherein the control circuit is further configured to:

start a hysteresis interval greater than the pacing escape interval;

detect an expiration of the hysteresis interval without identifying a valid event signal during the hysteresis interval; and start a pacing duration time interval in response to detecting the expiration of the hysteresis interval;

start the pacing escape interval during the pacing duration time interval;

detect an expiration of the pacing duration time interval; and start a next hysteresis interval in response to detecting the expiration of the pacing duration time interval.

12. The medical device of claim 1, further comprising a housing having a connector block configured to receive a medical lead carrying plurality of extra-cardiac electrodes;

wherein the sensing circuit is configured to receive the plurality of cardiac electrical signals via the plurality of the extra-cardiac electrodes; and the therapy delivery circuit is configured to deliver the generated pacing pulses via the plurality of extra-cardiac electrodes.

13. The medical device of claim 1 wherein the control circuit is further configured to:

start a first blanking interval and the validation window in response to the sensing circuit sensing the first ventricular event signal; and start a second blanking interval without starting a validation window in response to the sensing circuit sensing the second ventricular event signal during the validation window started in response to the first ventricular event signal.

14. The medical device of claim 1 wherein the sensing circuit comprises:

a first sensing channel configured to sense the first cardiac electrical signal via a first sensing electrode pair; and a second sensing channel configured to sense the second cardiac electrical signal via a second sensing electrode pair different than the first sensing electrode pair.

15. A method comprising:

starting a pacing escape interval to schedule a pending cardiac pacing pulse;

receiving a plurality of cardiac electrical signals;

sensing a first ventricular event signal from a first cardiac electrical signal of the plurality of cardiac electrical signals;

starting a validation window in response to sensing the first ventricular event signal;

determining that the first ventricular event signal is one of a valid event signal or an invalid event signal based on at least a second cardiac electrical signal of the plurality of cardiac electrical signals received during the validation window by:

sensing a second ventricular event signal from the second cardiac electrical signal;

determining that the second ventricular event signal is sensed during the validation window; and determining that the first ventricular event signal is a valid event signal in response to determining that the second ventricular event signal is sensed during the validation window;

cancelling the pending cardiac pacing pulse in response to determining that the first ventricular event signal is a valid event signal; and scheduling a subsequent pending pacing pulse by restarting the pacing escape interval in response to determining that the first ventricular event signal is a valid event signal.

16. The method of claim 15, further comprising:

determining that the pacing escape interval expires during the validation window; and withholding the pending cardiac pacing pulse that is scheduled at the expiration of the pacing escape interval in response to the pacing escape interval expiring during the validation window.

17. The method of claim 16, further comprising delivering the pending cardiac pacing pulse after the validation window in response to determining that the first ventricular event signal is an invalid event signal.

18. The method of claim 15, further comprising:

in response to determining that the first ventricular event signal is a valid event signal, determining a sensed event time;

determining an adjusted pacing escape interval having an effective starting time at the sensed event time; and restarting the pacing escape interval set to the adjusted pacing escape interval having the effective starting time at the sensed event time.

19. The method of claim 15, wherein determining that the first ventricular event signal is a valid event signal based on at least a third cardiac electrical signal of the plurality of cardiac electrical signals received during the validation window by:

storing a cardiac electrical signal segment from the third cardiac electrical signal in response to sensing the first ventricular event signal, wherein at least a portion of the cardiac electrical signal segment is received during at least a portion of the validation window;

determining at least one morphology feature from the cardiac electrical signal segment;

determining that the at least one morphology feature from the cardiac electrical signal segment meets R-wave criteria; and determining that the first ventricular event signal is a valid event signal in response to the at least one morphology feature meeting the R-wave criteria and the second ventricular event signal being sensed during the validation window.

20. The method of claim 19, further comprising:

determining the at least one morphology feature by:

determining a peak amplitude of the cardiac electrical signal segment;

determining a difference signal from the cardiac electrical signal segment; and determining a peak-to-peak amplitude of the difference signal; and determining that the at least one morphology feature meets the R-wave criteria in response to the peak amplitude being greater than an amplitude threshold and the peak-to-peak amplitude of the difference signal being greater than a slope threshold.

21. The method of claim 20, further comprising determining the peak-to-peak amplitude difference of the difference signal from a portion of the cardiac electrical signal segment that occurs later than the first ventricular event signal.

22. The method of claim 15, wherein determining that the first ventricular event signal is one of a valid event signal or an invalid event signal based on at least the second cardiac electrical signal of the plurality of cardiac electrical signals comprises:

determining that the second ventricular event signal is not sensed from the second cardiac electrical signal during the validation window;

determining at least one morphology feature from a cardiac electrical signal segment of the plurality of cardiac electrical signals, wherein at least a portion of the cardiac electrical signal segment is received during at least a portion of the validation window;

determining that the at least one morphology feature does not meet R-wave criteria; and determining that the first ventricular event signal is an invalid event signal in response to determining that a second ventricular event signal is not sensed from the second cardiac electrical signal during the validation window and that the at least one morphology feature does not meet the R-wave criteria.

23. The method of claim 15, further comprising:

starting a hysteresis interval;

identifying a valid event signal sensed by the sensing circuit during the hysteresis interval based on a first analysis of a first portion of the plurality of cardiac electrical signals;

restarting the hysteresis interval in response to identifying the valid event signal;

detecting an expiration of the restarted hysteresis interval without identifying a valid event signal during the restarted hysteresis interval;

starting the pacing escape interval to schedule the pending cardiac pacing pulse in response to detecting the expiration of the restarted hysteresis interval;

sensing the first ventricular event signal from the first cardiac electrical signal of the plurality of cardiac electrical signals during the pacing escape interval; and determining that the first ventricular event signal is one of a valid event signal or an invalid event signal based on a second analysis of a second portion of the plurality of cardiac electrical signals including the second cardiac electrical signal, the second analysis different than the first analysis and the first portion of the plurality of cardiac electrical signals different than the second portion of the plurality of cardiac electrical signals.

24. The method of claim 15, further comprising:

starting a hysteresis interval;

detecting an expiration of the hysteresis interval without identifying a valid event signal during the hysteresis interval;

starting a tachyarrhythmia analysis interval in response to detecting the expiration of the hysteresis interval before starting the pacing escape interval;

performing a morphology analysis of at least one of the plurality of cardiac electrical signals received by the sensing circuit during the tachyarrhythmia analysis interval;

detecting a tachyarrhythmia segment of the at least one of the plurality of cardiac electrical signals based on the morphology analysis; and starting a next hysteresis interval in response to detecting the tachyarrhythmia segment without scheduling a pacing pulse.

25. The method of claim 15, further comprising:

starting a hysteresis interval greater than the pacing escape interval;

detecting an expiration of the hysteresis interval without identifying a valid event signal during the hysteresis interval;

starting a pacing duration time interval in response to detecting the expiration of the hysteresis interval;

starting the pacing escape interval during the pacing duration time interval;

detecting an expiration of the pacing duration time interval; and starting a next hysteresis interval in response to detecting the expiration of the pacing duration time interval.

26. A non-transitory computer-readable medium storing a set of instructions which, when executed by a control circuit of a medical device, cause the medical device to:

start a pacing escape interval to schedule a pending cardiac pacing pulse;

receive a plurality of cardiac electrical signals;

sense a first ventricular event signal from a first cardiac electrical signal of the plurality of cardiac electrical signals;

sense a second ventricular event signal from a second cardiac electrical signal of the plurality of cardiac electrical signals;

start a validation window in response to sensing the first ventricular event signal;

determine that the first ventricular event signal is one of a valid event signal or an invalid event signal based on at least a second cardiac electrical signal of the plurality of cardiac electrical signals received during the validation window by:

determining that the second ventricular event signal is sensed by the sensing circuit during the validation window; and determining that the first ventricular event signal is a valid event signal in response to determining that the second ventricular event signal is sensed during the validation window;

cancel the pending cardiac pacing pulse in response to determining that the first ventricular event signal is a valid event signal; and schedule a subsequent pending pacing pulse by restarting the pacing escape interval in response to determining that the first ventricular event signal is a valid event signal.

* * * * *